United States Patent
Johnson et al.

(10) Patent No.: US 9,879,317 B2
(45) Date of Patent: Jan. 30, 2018

(54) REAL-TIME PCR POINT MUTATION ASSAYS FOR DETECTING HIV-1 RESISTANCE TO ANTIVIRAL DRUGS

(75) Inventors: Jeffrey A. Johnson, Stone Mountain, GA (US); Walid M. Heneine, Atlanta, GA (US); Jonathan T. Lipscomb, Decatur, GA (US)

(73) Assignee: THE UNITED STATES OF AMERICA, AS REPRESENTED BY THE SECRETARY, DEPARTMENT OF HEALTH AND HUMAN SERVICES, CENTERS FOR DISEASE CONTROL AND PREVENTION, Washington, DC (US)

( * ) Notice: Subject to any disclaimer, the term of this patent is extended or adjusted under 35 U.S.C. 154(b) by 536 days.

(21) Appl. No.: 13/985,499

(22) PCT Filed: Feb. 17, 2012

(86) PCT No.: PCT/US2012/025638
§ 371 (c)(1),
(2), (4) Date: Aug. 14, 2013

(87) PCT Pub. No.: WO2012/112884
PCT Pub. Date: Aug. 23, 2012

(65) Prior Publication Data
US 2013/0330726 A1    Dec. 12, 2013

Related U.S. Application Data

(60) Provisional application No. 61/443,926, filed on Feb. 17, 2011.

(51) Int. Cl.
*C12Q 1/68* (2006.01)
*C12Q 1/70* (2006.01)

(52) U.S. Cl.
CPC .......... *C12Q 1/686* (2013.01); *C12Q 1/6844* (2013.01); *C12Q 1/70* (2013.01); *C12Q 1/703* (2013.01); *C12Q 2600/106* (2013.01)

(58) Field of Classification Search
None
See application file for complete search history.

(56) References Cited

FOREIGN PATENT DOCUMENTS

| WO | WO-2000/000637 A2 | 1/2000 | |
|---|---|---|---|
| WO | WO-2002/055741 A2 | 7/2002 | |
| WO | WO2002055741 A2 * | 7/2002 | ............... C12Q 1/70 |
| WO | WO-2005/121379 A2 | 12/2005 | |
| WO | WO 2005121379 A2 * | 12/2005 | ............. C12Q 1/703 |
| WO | WO-2010000030 A1 | 1/2010 | |

OTHER PUBLICATIONS

Li, J. et al. Detection of low-level K65R variants in nucleoside reverse transcriptase inhibitor-naïve chronic and acute HIV-1 subtype C infections. The Journal of Infectious Diseases, vol. 203, p. 798-802, 2011.*

Li, J. et al., "Detection of Low-Level K65R Variants in Nucleoside Reverse Transcripase Inhibitor-Naive Chronic and Acute HIV-1 Subtype C Infections," *The Journal of Infectious Diseases*, 2011:203: 798-802.

* cited by examiner

*Primary Examiner* — Prabha Chunduru
(74) *Attorney, Agent, or Firm* — Kilpatrick Townsend & Stockton LLP

(57) ABSTRACT

Disclosed are compositions including primers and probes, which are capable of interacting with the disclosed nucleic acids, such as the nucleic acids encoding the reverse transcriptase, protease, or integrase of HIV as disclosed herein. Thus, provided is an oligonucleotide comprising any one of the nucleotide sequences set for in SEQ ID NOS: 1-89, 96-122, and 124-141. Also provided are the oligonucleotides consisting of the nucleotides as set forth in SEQ ID NOS: 1-89, 96-122, and 124-141. Each of the disclosed oligonucleotides is a probe or a primer. Also provided are mixtures of primers and probes and for use in RT-PCR and primary PCR reactions disclosed herein. Provided are methods for the specific detection of several mutations in HIV simultaneously or sequentially. Mutations in the reverse transcriptase, protease, or integrase of HIV can be detected using the methods described herein.

6 Claims, 7 Drawing Sheets

SEQUENCE LISTING

```
<160> NUMBER OF SEQ ID NOS: 141

<210> SEQ ID NO 1
<211> LENGTH: 23
<212> TYPE: DNA
<213> ORGANISM: Artificial Sequence
<220> FEATURE:
<223> OTHER INFORMATION: synthetic construct

<400> SEQUENCE: 1
cctcagatca ctctttggca acg                                              23

<210> SEQ ID NO 2
<211> LENGTH: 25
<212> TYPE: DNA
<213> ORGANISM: Artificial Sequence
<220> FEATURE:
<223> OTHER INFORMATION: synthetic construct

<400> SEQUENCE: 2
aaagttaaac aatggccatt gacag                                            25

<210> SEQ ID NO 3
<211> LENGTH: 23
<212> TYPE: DNA
<213> ORGANISM: Artificial Sequence
<220> FEATURE:
<223> OTHER INFORMATION: synthetic construct

<400> SEQUENCE: 3
atccctgcat aaatctgact tgc                                              23

<210> SEQ ID NO 4
<211> LENGTH: 23
<212> TYPE: DNA
<213> ORGANISM: Artificial Sequence
<220> FEATURE:
<223> OTHER INFORMATION: synthetic construct

<400> SEQUENCE: 4
cctcaaatca ctctttggca gcg                                              23
```

<210> SEQ ID NO 5
<211> LENGTH: 27
<212> TYPE: DNA
<213> ORGANISM: Artificial Sequence
<220> FEATURE:
<223> OTHER INFORMATION: synthetic construct

<400> SEQUENCE: 5
aggttaaaca atggccattg acagaag                                27

<210> SEQ ID NO 6
<211> LENGTH: 22
<212> TYPE: DNA
<213> ORGANISM: Artificial Sequence
<220> FEATURE:
<223> OTHER INFORMATION: synthetic construct

<400> SEQUENCE: 6
ctgggtaaat ctgacttgcc ca                                     22

<210> SEQ ID NO 7
<211> LENGTH: 27
<212> TYPE: DNA
<213> ORGANISM: Artificial Sequence
<220> FEATURE:
<223> OTHER INFORMATION: synthetic construct

<400> SEQUENCE: 7
cttctgggaa gttcaattag gaatacc                                27

<210> SEQ ID NO 8
<211> LENGTH: 27
<212> TYPE: DNA
<213> ORGANISM: Artificial Sequence
<220> FEATURE:
<223> OTHER INFORMATION: synthetic construct

<400> SEQUENCE: 8
cctggtgtct cattgtttat actaggt                                27

<210> SEQ ID NO 9
<211> LENGTH: 35
<212> TYPE: DNA
<213> ORGANISM: Artificial Sequence
<220> FEATURE:
<223> OTHER INFORMATION: synthetic construct

<400> SEQUENCE: 9
tggatgtggg tgatgcatat ttytcarttc cctta                       35

<210> SEQ ID NO 10
<211> LENGTH: 31
<212> TYPE: DNA
<213> ORGANISM: Artificial Sequence
<220> FEATURE:
<223> OTHER INFORMATION: synthetic construct

<400> SEQUENCE: 10
catayaatac yccartattt gycataaaaa g                           31

<210> SEQ ID NO 11
<211> LENGTH: 27
<212> TYPE: DNA
<213> ORGANISM: Artificial Sequence
<220> FEATURE:
<223> OTHER INFORMATION: synthetic construct -continued

<400> SEQUENCE: 11
cctggtgtct cattgtttat actaggt                                    27

<210> SEQ ID NO 12
<211> LENGTH: 29
<212> TYPE: DNA
<213> ORGANISM: Artificial Sequence
<220> FEATURE:
<223> OTHER INFORMATION: synthetic construct

<400> SEQUENCE: 12
rtatttgcca taaagaaraa rrayaatac                                  29

<210> SEQ ID NO 13
<211> LENGTH: 29
<212> TYPE: DNA
<213> ORGANISM: Artificial Sequence
<220> FEATURE:
<223> OTHER INFORMATION: synthetic construct

<400> SEQUENCE: 13
rtatttgcca taaagaaraa rrayaacac                                  29

<210> SEQ ID NO 14
<211> LENGTH: 25
<212> TYPE: DNA
<213> ORGANISM: Artificial Sequence
<220> FEATURE:
<223> OTHER INFORMATION: synthetic construct

<400> SEQUENCE: 14
gtatggtaaa tgcagtatac ttcct                                      25

<210> SEQ ID NO 15
<211> LENGTH: 30
<212> TYPE: DNA
<213> ORGANISM: Artificial Sequence
<220> FEATURE:
<223> OTHER INFORMATION: synthetic construct

<400> SEQUENCE: 15
ccartatttg ccataaagaa raarrayagt                                 30

<210> SEQ ID NO 16
<211> LENGTH: 31
<212> TYPE: DNA
<213> ORGANISM: Artificial Sequence
<220> FEATURE:
<223> OTHER INFORMATION: synthetic construct

<400> SEQUENCE: 16
trtttgccat aaagaaaaaa rayagtamca g                               31

<210> SEQ ID NO 17
<211> LENGTH: 28
<212> TYPE: DNA
<213> ORGANISM: Artificial Sequence
<220> FEATURE:
<223> OTHER INFORMATION: synthetic construct

<400> SEQUENCE: 17
ttgccataaa gaaaaaarac agtgacag                                   28

<210> SEQ ID NO 18
<211> LENGTH: 28

<212> TYPE: DNA
<213> ORGANISM: Artificial Sequence
<220> FEATURE:
<223> OTHER INFORMATION: synthetic construct

<400> SEQUENCE: 18
ttgccataaa gaaaaaarac agyracag					28

<210> SEQ ID NO 19
<211> LENGTH: 26
<212> TYPE: DNA
<213> ORGANISM: Artificial Sequence
<220> FEATURE:
<223> OTHER INFORMATION: synthetic construct

<400> SEQUENCE: 19
gccataaaga aaaaaracrg tracgg					26

<210> SEQ ID NO 20
<211> LENGTH: 25
<212> TYPE: DNA
<213> ORGANISM: Artificial Sequence
<220> FEATURE:
<223> OTHER INFORMATION: synthetic construct

<400> SEQUENCE: 20
gtatggtaaa tgcagtatac ttcct					25

<210> SEQ ID NO 21
<211> LENGTH: 32
<212> TYPE: DNA
<213> ORGANISM: Artificial Sequence
<220> FEATURE:
<223> OTHER INFORMATION: synthetic construct

<400> SEQUENCE: 21
agtatttgcc ataagaaaa aaracagtam ta					32

<210> SEQ ID NO 22
<211> LENGTH: 22
<212> TYPE: DNA
<213> ORGANISM: Artificial Sequence
<220> FEATURE:
<223> OTHER INFORMATION: synthetic construct

<400> SEQUENCE: 22
tcchgcaggg ttaaaraagg ac					22

<210> SEQ ID NO 23
<211> LENGTH: 22
<212> TYPE: DNA
<213> ORGANISM: Artificial Sequence
<220> FEATURE:
<223> OTHER INFORMATION: synthetic construct

<400> SEQUENCE: 23
tccckcwggg ttaaraaggg ac					22

<210> SEQ ID NO 24
<211> LENGTH: 24
<212> TYPE: DNA
<213> ORGANISM: Artificial Sequence
<220> FEATURE:
<223> OTHER INFORMATION: synthetic construct

<400> SEQUENCE: 24

```
catcchgcag grttaaaaaa gggc                                          24

<210> SEQ ID NO 25
<211> LENGTH: 24
<212> TYPE: DNA
<213> ORGANISM: Artificial Sequence
<220> FEATURE:
<223> OTHER INFORMATION: synthetic construct

<400> SEQUENCE: 25
catcccgcag ggttaaaava ggat                                          24

<210> SEQ ID NO 26
<211> LENGTH: 25
<212> TYPE: DNA
<213> ORGANISM: Artificial Sequence
<220> FEATURE:
<223> OTHER INFORMATION: synthetic construct

<400> SEQUENCE: 26
gtatggtaaa tgcagtatac ttcct                                         25

<210> SEQ ID NO 27
<211> LENGTH: 23
<212> TYPE: DNA
<213> ORGANISM: Artificial Sequence
<220> FEATURE:
<223> OTHER INFORMATION: synthetic construct

<400> SEQUENCE: 27
catcchgcag grctaaaaaa gaa                                           23

<210> SEQ ID NO 28
<211> LENGTH: 27
<212> TYPE: DNA
<213> ORGANISM: Artificial Sequence
<220> FEATURE:
<223> OTHER INFORMATION: synthetic construct

<400> SEQUENCE: 28
aaaacaaaay ccagamatgr ttggctg                                       27

<210> SEQ ID NO 29
<211> LENGTH: 28
<212> TYPE: DNA
<213> ORGANISM: Artificial Sequence
<220> FEATURE:
<223> OTHER INFORMATION: synthetic construct

<400> SEQUENCE: 29
gaaaacaaaa yccaramatr gttgghtg                                      28

<210> SEQ ID NO 30
<211> LENGTH: 22
<212> TYPE: DNA
<213> ORGANISM: Artificial Sequence
<220> FEATURE:
<223> OTHER INFORMATION: synthetic construct

<400> SEQUENCE: 30
caggatggag ttcataaccc at                                            22

<210> SEQ ID NO 31
<211> LENGTH: 31
<212> TYPE: DNA
<213> ORGANISM: Artificial Sequence
```

<220> FEATURE:
<223> OTHER INFORMATION: synthetic construct

<400> SEQUENCE: 31
ttyagaaaac aaaayccaga matgrttatm t                                         31

<210> SEQ ID NO 32
<211> LENGTH: 34
<212> TYPE: DNA
<213> ORGANISM: Artificial Sequence
<220> FEATURE:
<223> OTHER INFORMATION: synthetic construct

<400> SEQUENCE: 32
taggatctga cttagaaata ggrcagcata garc                                      34

<210> SEQ ID NO 33
<211> LENGTH: 29
<212> TYPE: DNA
<213> ORGANISM: Artificial Sequence
<220> FEATURE:
<223> OTHER INFORMATION: synthetic construct

<400> SEQUENCE: 33
aaatccaram mtarttatmt rtcagcacg                                            29

<210> SEQ ID NO 34
<211> LENGTH: 29
<212> TYPE: DNA
<213> ORGANISM: Artificial Sequence
<220> FEATURE:
<223> OTHER INFORMATION: synthetic construct

<400> SEQUENCE: 34
aaatccagam atarttatct rtcagcacg                                            29

<210> SEQ ID NO 35
<211> LENGTH: 29
<212> TYPE: DNA
<213> ORGANISM: Artificial Sequence
<220> FEATURE:
<223> OTHER INFORMATION: synthetic construct

<400> SEQUENCE: 35
aaayccaram atarttatct rycagcatg                                            29

<210> SEQ ID NO 36
<211> LENGTH: 22
<212> TYPE: DNA
<213> ORGANISM: Artificial Sequence
<220> FEATURE:
<223> OTHER INFORMATION: synthetic construct

<400> SEQUENCE: 36
caggatggag ttcataaccc at                                                   22

<210> SEQ ID NO 37
<211> LENGTH: 33
<212> TYPE: DNA
<213> ORGANISM: Artificial Sequence
<220> FEATURE:
<223> OTHER INFORMATION: synthetic construct

<400> SEQUENCE: 37
aarcaaaayc caramatart tatctrtcaa tay                                       33

<210> SEQ ID NO 38
<211> LENGTH: 24
<212> TYPE: DNA
<213> ORGANISM: Artificial Sequence
<220> FEATURE:
<223> OTHER INFORMATION: synthetic construct

<400> SEQUENCE: 38
acatctgtkg argtggggry tcac                                            24

<210> SEQ ID NO 39
<211> LENGTH: 27
<212> TYPE: DNA
<213> ORGANISM: Artificial Sequence
<220> FEATURE:
<223> OTHER INFORMATION: synthetic construct

<400> SEQUENCE: 39
asaayatctg ttrargtggg grttcac                                         27

<210> SEQ ID NO 40
<211> LENGTH: 27
<212> TYPE: DNA
<213> ORGANISM: Artificial Sequence
<220> FEATURE:
<223> OTHER INFORMATION: synthetic construct

<400> SEQUENCE: 40
asarcatctg tkgarrtggg grytcta                                         27

<210> SEQ ID NO 41
<211> LENGTH: 27
<212> TYPE: DNA
<213> ORGANISM: Artificial Sequence
<220> FEATURE:
<223> OTHER INFORMATION: synthetic construct

<400> SEQUENCE: 41
asarcatctg tkgarrtggg grytctt                                         27

<210> SEQ ID NO 42
<211> LENGTH: 25
<212> TYPE: DNA
<213> ORGANISM: Artificial Sequence
<220> FEATURE:
<223> OTHER INFORMATION: synthetic construct

<400> SEQUENCE: 42
arcatctgtk gargtggggr ytctc                                           25

<210> SEQ ID NO 43
<211> LENGTH: 25
<212> TYPE: DNA
<213> ORGANISM: Artificial Sequence
<220> FEATURE:
<223> OTHER INFORMATION: synthetic construct

<400> SEQUENCE: 43
arcatctgtk gargtggggr ytctg                                           25

<210> SEQ ID NO 44
<211> LENGTH: 26
<212> TYPE: DNA
<213> ORGANISM: Artificial Sequence
<220> FEATURE:
<223> OTHER INFORMATION: synthetic construct

```
<400> SEQUENCE: 44
sarcatctgt kgarrtgggg rytcga                                    26

<210> SEQ ID NO 45
<211> LENGTH: 23
<212> TYPE: DNA
<213> ORGANISM: Artificial Sequence
<220> FEATURE:
<223> OTHER INFORMATION: synthetic construct

<400> SEQUENCE: 45
cttctgtatg tcattgacag tcc                                       23

<210> SEQ ID NO 46
<211> LENGTH: 24
<212> TYPE: DNA
<213> ORGANISM: Artificial Sequence
<220> FEATURE:
<223> OTHER INFORMATION: synthetic construct

<400> SEQUENCE: 46
saacatctgt tgargtgggg rytt                                      24

<210> SEQ ID NO 47
<211> LENGTH: 29
<212> TYPE: DNA
<213> ORGANISM: Artificial Sequence
<220> FEATURE:
<223> OTHER INFORMATION: synthetic construct

<400> SEQUENCE: 47
tggacagtac agcctatart gctgccaga                                 29

<210> SEQ ID NO 48
<211> LENGTH: 25
<212> TYPE: DNA
<213> ORGANISM: Artificial Sequence
<220> FEATURE:
<223> OTHER INFORMATION: synthetic construct

<400> SEQUENCE: 48
gctytattag ayacaggrgc aggta                                     25

<210> SEQ ID NO 49
<211> LENGTH: 25
<212> TYPE: DNA
<213> ORGANISM: Artificial Sequence
<220> FEATURE:
<223> OTHER INFORMATION: synthetic construct

<400> SEQUENCE: 49
gctctattmg ayacaggagc wggta                                     25

<210> SEQ ID NO 50
<211> LENGTH: 27
<212> TYPE: DNA
<213> ORGANISM: Artificial Sequence
<220> FEATURE:
<223> OTHER INFORMATION: synthetic construct

<400> SEQUENCE: 50
tggtacagtt tcaataggac taatggg                                   27

<210> SEQ ID NO 51
```

<210> SEQ ID NO 51
<211> LENGTH: 24
<212> TYPE: DNA
<213> ORGANISM: Artificial Sequence
<220> FEATURE:
<223> OTHER INFORMATION: synthetic construct

<400> SEQUENCE: 51
ctytattmga yacaggrgca ggta                                          24

<210> SEQ ID NO 52
<211> LENGTH: 39
<212> TYPE: DNA
<213> ORGANISM: Artificial Sequence
<220> FEATURE:
<223> OTHER INFORMATION: synthetic construct

<400> SEQUENCE: 52
taaracagta tgatcagrta cccatagaaa tctgtggac                          39

<210> SEQ ID NO 53
<211> LENGTH: 27
<212> TYPE: DNA
<213> ORGANISM: Artificial Sequence
<220> FEATURE:
<223> OTHER INFORMATION: synthetic construct

<400> SEQUENCE: 53
ctgycaacrt aattggaaga aatccga                                       27

<210> SEQ ID NO 54
<211> LENGTH: 27
<212> TYPE: DNA
<213> ORGANISM: Artificial Sequence
<220> FEATURE:
<223> OTHER INFORMATION: synthetic construct

<400> SEQUENCE: 54
ctrccaacat aattggaaga aayccga                                       27

<210> SEQ ID NO 55
<211> LENGTH: 27
<212> TYPE: DNA
<213> ORGANISM: Artificial Sequence
<220> FEATURE:
<223> OTHER INFORMATION: synthetic construct

<400> SEQUENCE: 55
ctrycaacrt aattggaaga aatccaa                                       27

<210> SEQ ID NO 56
<211> LENGTH: 25
<212> TYPE: DNA
<213> ORGANISM: Artificial Sequence
<220> FEATURE:
<223> OTHER INFORMATION: synthetic construct

<400> SEQUENCE: 56
cttctgtcaa tggccattgt ttaac                                         25

<210> SEQ ID NO 57
<211> LENGTH: 26
<212> TYPE: DNA
<213> ORGANISM: Artificial Sequence
<220> FEATURE:
<223> OTHER INFORMATION: synthetic construct

<400> SEQUENCE: 57
cctgycaacr taattggaag aaayct                                           26

<210> SEQ ID NO 58
<211> LENGTH: 33
<212> TYPE: DNA
<213> ORGANISM: Artificial Sequence
<220> FEATURE:
<223> OTHER INFORMATION: synthetic construct

<400> SEQUENCE: 58
tgtaccagta aaattaaagc caggaatgga tgg                                   33

<210> SEQ ID NO 59
<211> LENGTH: 22
<212> TYPE: DNA
<213> ORGANISM: Artificial Sequence
<220> FEATURE:
<223> OTHER INFORMATION: synthetic construct

<400> SEQUENCE: 59
cccagtaggr ttaaaraagg ac                                               22

<210> SEQ ID NO 60
<211> LENGTH: 22
<212> TYPE: DNA
<213> ORGANISM: Artificial Sequence
<220> FEATURE:
<223> OTHER INFORMATION: synthetic construct

<400> SEQUENCE: 60
cccakcrggg ttraaagagg ac                                               22

<210> SEQ ID NO 61
<211> LENGTH: 22
<212> TYPE: DNA
<213> ORGANISM: Artificial Sequence
<220> FEATURE:
<223> OTHER INFORMATION: synthetic construct

<400> SEQUENCE: 61
cccagcaggr ttaaaavagg at                                               22

<210> SEQ ID NO 62
<211> LENGTH: 29
<212> TYPE: DNA
<213> ORGANISM: Artificial Sequence
<220> FEATURE:
<223> OTHER INFORMATION: synthetic construct

<400> SEQUENCE: 62
aaaagcatta rtrgaaatyt gtrcaggac                                        29

<210> SEQ ID NO 63
<211> LENGTH: 32
<212> TYPE: DNA
<213> ORGANISM: Artificial Sequence
<220> FEATURE:
<223> OTHER INFORMATION: synthetic construct

<400> SEQUENCE: 63
aataaaagca ttartrgaaa tytgtrcagc at                                    32

<210> SEQ ID NO 64
<211> LENGTH: 30
<212> TYPE: DNA

```
<213> ORGANISM: Artificial Sequence
<220> FEATURE:
<223> OTHER INFORMATION: synthetic construct

<400> SEQUENCE: 64
taaaagcatt artrgaaaty tgtrcakgtc                                       30

<210> SEQ ID NO 65
<211> LENGTH: 27
<212> TYPE: DNA
<213> ORGANISM: Artificial Sequence
<220> FEATURE:
<223> OTHER INFORMATION: synthetic construct

<400> SEQUENCE: 65
aagcattart rgaaatytgt rcakggc                                          27

<210> SEQ ID NO 66
<211> LENGTH: 23
<212> TYPE: DNA
<213> ORGANISM: Artificial Sequence
<220> FEATURE:
<223> OTHER INFORMATION: synthetic construct

<400> SEQUENCE: 66
cctaattgaa cttcccagaa gtc                                              23

<210> SEQ ID NO 67
<211> LENGTH: 35
<212> TYPE: DNA
<213> ORGANISM: Artificial Sequence
<220> FEATURE:
<223> OTHER INFORMATION: synthetic construct

<400> SEQUENCE: 67
ttgggcctga aaatccatac aatactccag tattt                                 35

<210> SEQ ID NO 68
<211> LENGTH: 39
<212> TYPE: DNA
<213> ORGANISM: Artificial Sequence
<220> FEATURE:
<223> OTHER INFORMATION: synthetic construct

<400> SEQUENCE: 68
tagtagattt cagagaactt aataagagaa ctcaagact                             39

<210> SEQ ID NO 69
<211> LENGTH: 31
<212> TYPE: DNA
<213> ORGANISM: Artificial Sequence
<220> FEATURE:
<223> OTHER INFORMATION: synthetic construct

<400> SEQUENCE: 69
aatactccar tatttgycat aargaargca a                                     31

<210> SEQ ID NO 70
<211> LENGTH: 30
<212> TYPE: DNA
<213> ORGANISM: Artificial Sequence
<220> FEATURE:
<223> OTHER INFORMATION: synthetic construct

<400> SEQUENCE: 70
atactccart atttgycata aagaargcga                                       30
```

<210> SEQ ID NO 71
<211> LENGTH: 29
<212> TYPE: DNA
<213> ORGANISM: Artificial Sequence
<220> FEATURE:
<223> OTHER INFORMATION: synthetic construct

<400> SEQUENCE: 71
rtatttgcya taaagaaraa rgayagcac                                      29

<210> SEQ ID NO 72
<211> LENGTH: 30
<212> TYPE: DNA
<213> ORGANISM: Artificial Sequence
<220> FEATURE:
<223> OTHER INFORMATION: synthetic construct

<400> SEQUENCE: 72
gttctctraa atctaytawt tttctccctc                                     30

<210> SEQ ID NO 73
<211> LENGTH: 29
<212> TYPE: DNA
<213> ORGANISM: Artificial Sequence
<220> FEATURE:
<223> OTHER INFORMATION: synthetic construct

<400> SEQUENCE: 73
ttctctraaa tctaytawtt ttctccccc                                      29

<210> SEQ ID NO 74
<211> LENGTH: 25
<212> TYPE: DNA
<213> ORGANISM: Artificial Sequence
<220> FEATURE:
<223> OTHER INFORMATION: synthetic construct

<400> SEQUENCE: 74
aacatctgtk gargtggggr ytcac                                          25

<210> SEQ ID NO 75
<211> LENGTH: 25
<212> TYPE: DNA
<213> ORGANISM: Artificial Sequence
<220> FEATURE:
<223> OTHER INFORMATION: synthetic construct

<400> SEQUENCE: 75
aacatytgtt aargtggggr ytcac                                          25

<210> SEQ ID NO 76
<211> LENGTH: 34
<212> TYPE: DNA
<213> ORGANISM: Artificial Sequence
<220> FEATURE:
<223> OTHER INFORMATION: synthetic construct

<400> SEQUENCE: 76
tatgaactcc atcctgataa atggacagta carc                                34

<210> SEQ ID NO 77
<211> LENGTH: 31
<212> TYPE: DNA
<213> ORGANISM: Artificial Sequence
<220> FEATURE:

<223> OTHER INFORMATION: synthetic construct

<400> SEQUENCE: 77
tatgagctcc atcctgataa atggacagtr c                                31

<210> SEQ ID NO 78
<211> LENGTH: 26
<212> TYPE: DNA
<213> ORGANISM: Artificial Sequence
<220> FEATURE:
<223> OTHER INFORMATION: synthetic construct

<400> SEQUENCE: 78
tgycaacrta attggragra aycgga                                      26

<210> SEQ ID NO 79
<211> LENGTH: 27
<212> TYPE: DNA
<213> ORGANISM: Artificial Sequence
<220> FEATURE:
<223> OTHER INFORMATION: synthetic construct

<400> SEQUENCE: 79
ctrycaacrt aattggaagr aatkgga                                     27

<210> SEQ ID NO 80
<211> LENGTH: 25
<212> TYPE: DNA
<213> ORGANISM: Artificial Sequence
<220> FEATURE:
<223> OTHER INFORMATION: synthetic construct

<400> SEQUENCE: 80
rycaacrtaa ttggragaga ycgga                                       25

<210> SEQ ID NO 81
<211> LENGTH: 30
<212> TYPE: DNA
<213> ORGANISM: Artificial Sequence
<220> FEATURE:
<223> OTHER INFORMATION: synthetic construct

<400> SEQUENCE: 81
aatgctttta tttttcttc tgtcaatggc                                   30

<210> SEQ ID NO 82
<211> LENGTH: 37
<212> TYPE: DNA
<213> ORGANISM: Artificial Sequence
<220> FEATURE:
<223> OTHER INFORMATION: synthetic construct

<400> SEQUENCE: 82
taaattttcc cattagtcct attgaaactg taccagt                          37

<210> SEQ ID NO 83
<211> LENGTH: 28
<212> TYPE: DNA
<213> ORGANISM: Artificial Sequence
<220> FEATURE:
<223> OTHER INFORMATION: synthetic construct

<400> SEQUENCE: 83
gracamaaaa tccagaaata gtygcctg                                    28

```
<210> SEQ ID NO 84
<211> LENGTH: 26
<212> TYPE: DNA
<213> ORGANISM: Artificial Sequence
<220> FEATURE:
<223> OTHER INFORMATION: synthetic construct

<400> SEQUENCE: 84
acamraaatc cagaaatagt ygcttg                                          26

<210> SEQ ID NO 85
<211> LENGTH: 22
<212> TYPE: DNA
<213> ORGANISM: Artificial Sequence
<220> FEATURE:
<223> OTHER INFORMATION: synthetic construct

<400> SEQUENCE: 85
caggatggag ttcataaccc at                                              22

<210> SEQ ID NO 86
<211> LENGTH: 34
<212> TYPE: DNA
<213> ORGANISM: Artificial Sequence
<220> FEATURE:
<223> OTHER INFORMATION: synthetic construct

<400> SEQUENCE: 86
taggatctga tttagaaata gggcaacata grac                                 34

<210> SEQ ID NO 87
<211> LENGTH: 34
<212> TYPE: DNA
<213> ORGANISM: Artificial Sequence
<220> FEATURE:
<223> OTHER INFORMATION: synthetic construct

<400> SEQUENCE: 87
taggatctga tttagaaata aagcaacata grac                                 34

<210> SEQ ID NO 88
<211> LENGTH: 30
<212> TYPE: DNA
<213> ORGANISM: Artificial Sequence
<220> FEATURE:
<223> OTHER INFORMATION: synthetic construct

<400> SEQUENCE: 88
aaaayccaga matartyatc trycagcatg                                      30

<210> SEQ ID NO 89
<211> LENGTH: 31
<212> TYPE: DNA
<213> ORGANISM: Artificial Sequence
<220> FEATURE:
<223> OTHER INFORMATION: synthetic construct

<400> SEQUENCE: 89
maaaayccar amatartyat mtrtcagcac g                                    31

<210> SEQ ID NO 90
<211> LENGTH: 297
<212> TYPE: DNA
<213> ORGANISM: HIV

<400> SEQUENCE: 90
```

```
cctcaggtca ctctttggca acgacccctc gtcacaataa agatagggggg gcaactaaag    60 gaagctctat tagatacagg agcagatgat acagtattag aagaaatgag tttgccagga   120
agatggaaac caaaaatgat agggggaatt ggaggtttta tcaaagtaag acagtatgat   180
cagatactca tagaaatctg tggacataaa gctataggta cagtattagt aggacctaca   240
cctgtcaaca taattggaag aaatctgttg actcagattg gttgcacttt aaatttt      297
```

<210> SEQ ID NO 91
<211> LENGTH: 1680
<212> TYPE: DNA
<213> ORGANISM: HIV

<400> SEQUENCE: 91

```
cccattagcc ctattgagac tgtaccagta aaattaaagc caggaatgga tggcccaaaa    60
gttaaacaat ggccattgac agaagaaaaa ataaaagcat tagtagaaat ttgtacagag   120
atggaaaagg aagggaaaat ttcaaaaatt gggcctgaaa atccatacaa tactccagta   180
tttgccataa agaaaaaaga cagtactaaa tggagaaaat tagtagattt cagagaactt   240
aataagagaa ctcaagactt ctggaagtt caattaggaa taccacatcc cgcagggtta   300
aaaaagaaaa aatcagtaac agtactggat gtgggtgatg catatttttc agttccctta   360
gatgaagact tcaggaagta tactgcattt accataccta gtataaacaa tgagacacca   420
gggattagat atcagtacaa tgtgcttcca cagggatgga aaggatcacc agcaatattc   480
caaagtagca tgacaaaaat cttagagcct tttagaaaac aaaatccaga catagttatc   540
tatcaataca tggatgattt gtatgtagga tctgacttag aaatagggca gcatagaaca   600
aaaatagagg agctgagaca acatctgttg aggtggggac ttaccacacc agacaaaaaa   660
catcagaaag aacctccatt cctttggatg ggttatgaac tccatcctga taaatggaca   720
gtacagccta tagtgctgcc agaaaaagac agctggactg tcaatgacat acagaagtta   780
gtggggaaat tgaattgggc aagtcagatt tacccaggga ttaaagtaag gcaattatgt   840
aaactcctta gaggaaccaa agcactaaca gaagtaatac cactaacaga agaagcagag   900
ctagaactgg cagaaaacag agagattcta aaagaaccag tacatggagt gtattatgac   960
ccatcaaaag acttaatagc agaaatacag aagcaggggc aaggccaatg gacatatcaa  1020
atttatcaag agccatttaa aaatctgaaa acaggaaaat atgcaagaat gaggggtgcc  1080
cacactaatg atgtaaaaca attaacagag gcagtgcaaa aaataaccac agaaagcata  1140
gtaatatggg gaaagactcc taaatttaaa ctgcccatac aaaaggaaac atgggaaaca  1200
tggtggacag agtattggca agccacctgg attcctgagt gggagtttgt taatacccct  1260
cccttagtga aattatggta ccagttagag aaagaaccca tagtaggagc agaaaccttc  1320
tatgtagatg gggcagctaa cagggagact aaattaggaa aagcaggata tgttactaat  1380
agaggaagac aaaaagttgt caccctaact gacacaacaa atcagaagac tgagttacaa  1440
gcaatttatc tagctttgca ggattcggga ttagaagtaa acatagtaac agactcacaa  1500
tatgcattag gaatcattca agcacaacca gatcaaagtg aatcagagtt agtcaatcaa  1560
ataatagagc agttaataaa aaaggaaaag gtctatctgg catgggtacc agcacacaaa  1620
ggaattggag gaaatgaaca agtagataaa ttagtcagtg ctggaatcag gaaagtacta  1680
```

<210> SEQ ID NO 92
<211> LENGTH: 297
<212> TYPE: DNA
<213> ORGANISM: HIV

<400> SEQUENCE: 92

```
cctcaaatca ctctttggca gcgacccctt gtcacaataa agtaggggg tcagataaag      60
gaggctctct tagatacagg agcagatgat acagtattag aagacataaa tttgccagga    120
aaatggaaac caaaaatgat aggaggaatt ggaggtttta tcaaagtaag acagtatgat    180
caaatactta tagaaatttg tggaaaaaag gctataggta cagtattagt gggacccaca    240
cctgtcaaca taattggaag aaatatgttg actcagcttg gatgcacact aaatttt       297
```

<210> SEQ ID NO 93
<211> LENGTH: 963
<212> TYPE: DNA
<213> ORGANISM: HIV

<400> SEQUENCE: 93

```
ccaattagtc cyattgaaac tgtaccagta aaattaaagc cagggatgga tggcccaaag     60
gtcaaacaat ggccattgac agaagaaaaa ataaaagcat taatagcaat ttgtgaagag   120
atggagaagg aaggaaaaat tacaaaaatt gggcctgaaa atccatataa cacccagta    180
tttgccataa aaagaaagga cagtactaag tggagaaaat tagtagattt cagggaactc   240
aataaaagaa ctcaagactt tgggaagtt caattaggga taccacaccc agcagggtta    300
aagaaaaaga atcagtaac agtactggat gtggggatg catattttc agttcccttt     360
gataaagact tcagaaaata tactgcattc accataccta gtataaacaa tgagacacca   420
gggattagat atcaatataa tgtgcttcca caggatgga aaggatcacc atcaatattc    480
caaagtagta tgacaaaaat cttagagccc tttagggcac aaaatccaga attggttatt    540
tatcaatata tggatgactt gtatgtagga tccgacttag aaataggca gcatagagca    600
aaaatagagg agttaagaaa acatctattg aggtgggat ttaccacacc agacaagaaa    660
catcagaaag aacctccatt tctttggatg gggtatgaac tccatcctga caaatggaca   720
gtacagccta taaagctgcc agaaaaggat agctggactg ttaatgatat acagaagtta   780
gtgggaaaac taaactgggc aagtcagatt tacaaaggga ttaaagtaag gcagctgtgt   840
agactcctta ggggagccaa agcactaaca gacatagtac cactgactga agaagcagaa   900
ttagaattgg cagagaacag ggaaattcta aaagaaccag tacatggagt atattatgac   960
tca                                                                  963
```

<210> SEQ ID NO 94
<211> LENGTH: 297
<212> TYPE: DNA
<213> ORGANISM: HIV

<400> SEQUENCE: 94

```
cctcaaatca ctctttggca acgacccctt gtcacagtaa rgataggggg acaactaaag     60
gaagctctat tagatacagg agcagatgat acagtattgg aagaaatgaa tttgccagga   120
aaatggaaac caaaaatgat aggggggaatt ggaggcttta tcaaagtaag acagtatgat   180
caaatacttg tagaaatctg tggatataag gctataggta cagtgttagt aggacctaca   240
cctgtcaaca taattggaag aaatttgttg actcagattg gttgcacttt aaatttt       297
```

<210> SEQ ID NO 95
<211> LENGTH: 963
<212> TYPE: DNA
<213> ORGANISM: HIV

<400> SEQUENCE: 95

```
ccaattagtc ctattgaaac tgtaccagta aaattaaagc cagggatgga tggcccaaaa      60
gttaaacaat ggccgttaac agaagaaaaa ataaaagcac taacagaaat ttgtacagaa     120
atggaaaagg aaggaaaaat ttcaagaatt gggcctgaaa atccatacaa tactccaata     180
tttgccataa agaaaaaaga cagtactaar tggagaaaat tagtagattt tagagaactt     240
aataagagaa ctcaagactt ctgggaagtt caactaggaa taccacatcc tgcagggcta     300
aaaagaaaa aatcagtaac agtactggat gtgggwgatg catattttc agttccctta      360
tatgaagact ttagaaaata tactgcattc accataccya gtataaataa tgagacacca     420
ggaattagat atcagtacaa tgtgcttcca caaggatgga aggatcacc ggcaatattt      480
caaagtagca tgacaaaaat cttagaacct tttagaaaac aaaatccaga atggtgatc      540
tatcaataca tggatgattt gtatgtagga tctgacttag aaatagggca gcatagaata     600
aaaatagagg aattaaggga acacttattg aagtggggat ttaccacacc agacaaaaag     660
catcagaaag aacccccatt tctttggatg ggttatgaac tccatccgga taaatggaca     720
gtacagccta taaaactgcc agaaaaagaa agctggactg tcaatgatat acagaagtta     780
gtgggaaaat taaattgggc aagtcagatt tatccaggaa ttaaagtaag acaattatgc     840
aaatgcatta ggggagccaa agcactgaca gaagtagtac cactgacaga agaagcagaa     900
ttagaactgg cagaaaacag agaaattcta aaagaaccag tacatggagt gtattatgat     960
cca                                                                   963
```

<210> SEQ ID NO 96
<211> LENGTH: 32
<212> TYPE: DNA
<213> ORGANISM: Artificial Sequence
<220> FEATURE:
<223> OTHER INFORMATION: synthetic construct

<400> SEQUENCE: 96

```
aatwaaagca ttartrgaaa tytgtrcwgc at                                    32
```

<210> SEQ ID NO 97
<211> LENGTH: 29
<212> TYPE: DNA
<213> ORGANISM: Artificial Sequence
<220> FEATURE:
<223> OTHER INFORMATION: synthetic construct

<400> SEQUENCE: 97

```
aaaagcatta rtrgaaatyt gtrcaggac                                        29
```

<210> SEQ ID NO 98
<211> LENGTH: 28
<212> TYPE: DNA
<213> ORGANISM: Artificial Sequence
<220> FEATURE:
<223> OTHER INFORMATION: synthetic construct

<400> SEQUENCE: 98

```
acaatactcc artatttgcc ataarcag                                         28
```

<210> SEQ ID NO 99
<211> LENGTH: 37
<212> TYPE: DNA
<213> ORGANISM: Artificial Sequence
<220> FEATURE:
<223> OTHER INFORMATION: synthetic construct
```

<400> SEQUENCE: 99
tcagagaact taataaraga actcaagact tctggga         37

<210> SEQ ID NO 100
<211> LENGTH: 29
<212> TYPE: DNA
<213> ORGANISM: Artificial Sequence
<220> FEATURE:
<223> OTHER INFORMATION: synthetic construct

<400> SEQUENCE: 100
agaratttgt acagaratgg aaaaggaag                  29

<210> SEQ ID NO 101
<211> LENGTH: 26
<212> TYPE: DNA
<213> ORGANISM: Artificial Sequence
<220> FEATURE:
<223> OTHER INFORMATION: synthetic construct

<400> SEQUENCE: 101
caacatytgt taargtgggg rgatac                     26

<210> SEQ ID NO 102
<211> LENGTH: 30
<212> TYPE: DNA
<213> ORGANISM: Artificial Sequence
<220> FEATURE:
<223> OTHER INFORMATION: synthetic construct

<400> SEQUENCE: 102
aaaayccagr aatartyatc trtcagcatg                 30

<210> SEQ ID NO 103
<211> LENGTH: 28
<212> TYPE: DNA
<213> ORGANISM: Artificial Sequence
<220> FEATURE:
<223> OTHER INFORMATION: synthetic construct

<400> SEQUENCE: 103
aayccagama tartyatctr tcagcacg                   28

<210> SEQ ID NO 104
<211> LENGTH: 30
<212> TYPE: DNA
<213> ORGANISM: Artificial Sequence
<220> FEATURE:
<223> OTHER INFORMATION: synthetic construct

<400> SEQUENCE: 104
aaaayccaga ratartyaty trtcagcatg                 30

<210> SEQ ID NO 105
<211> LENGTH: 2954
<212> TYPE: DNA
<213> ORGANISM: Simian Immunodeficiency Virus

<400> SEQUENCE: 105
cccatagcta aagtagagcc tgtaaaagtc gccttaaagc caggaaagga tggaccaaaa      60
ttgaagcagt ggccattatc aaagaaaag atagttgcat taagagaaat ctgtgaaaag     120
atggaaaagg atggtcagtt ggaggaagct ccccgacca atccatacaa cacccccaca     180

```
tttgctataa agaaaaagga taagaacaaa tggagaatgc tgatagattt tagggaacta         240
aatagggtca ctcaggactt tacggaagtc caattaggaa taccacaccc tgcaggacta         300
gcaaaaagga aagaattac agtactggat ataggtgatg catatttctc catacctcta          360
gatgaagaat ttaggcagta cactgccttt actttaccat cagtaaataa tgcagagcca         420
ggaaaacgat acatttataa ggttctgcct cagggatgga aggggtcacc agccatcttc         480
caatacacta tgagacatgt gctagaaccc ttcaggaagg caaatccaga tgtgaccttta        540 gtccagtata tggatgacat cttaatagct agtgacagga cagacctgga acatgacagg         600
gtagttttac agtcaaagga actcttgaat agcatagggt tttctacccc agaagagaaa         660
ttccaaaaag atcccccatt tcaatggatg gggtacgaat tgtggccaac aaaatggaag         720
ttgcaaaaga tagagttgcc acaaagagag acctggacag tgaatgatat acagaagtta        780
gtaggagtat taaattgggc agctcaaatt tatccaggta taaaaccaa acatctctgt          840 aggttaatta gaggaaaaat gactctaaca gaggaagttc agtggactga gatggcagaa         900
gcagaatatg aggaaaataa aataattctc agtcaggaac aagaaggatg ttattaccaa         960
gaaggcaagc cattagaagc cacggtaata aagagtcagg acaatcagtg gtcttataaa         1020
attcaccaag aagacaaaat actgaaagta ggaaaatttg caaagataaa gaatacacat         1080
accaatggag tgagactatt agcacatgta atacagaaaa taggaaagga agcaatagtg          1140
atctggggac aggtccccaaa attccactta ccagttgaga aggatgtatg ggaacagtgg         1200
tggacagact attggcaggt aacctggata ccggaatggg attttatctc aacaccaccg         1260
ctagtaagat tagtcttcaa tctagtgaag gaccctatag agggagaaga aacctattat         1320
acagatggat catgtaataa acagtcaaaa gaagggaaag caggatatat cacagatagg         1380
ggcaaagaca agtaaaagt gttagaacag actactaatc aacaagcaga attggaagca          1440
tttctcatgg cattgacaga ctcagggcca aaggcaaata ttatagtaga ttcacaatat         1500
gttatgggaa taataacagg atgccctaca gaatcagaga gcaggctagt taatcaaata        1560
atagaagaaa tgattaaaaa gtcagaaatt tatgtagcat gggtaccagc acacaaaggt         1620
ataggaggaa accaagaaat agaccaccta gttagtcaag ggattagaca agttctcttc         1680
ttggaaaaga tagagccagc acaagaagaa catgataaat accatagtaa tgtaaaagaa         1740
ttggtattca aatttggatt acccagaata gtggccagac agatagtaga cacctgtgat         1800
aaatgtcatc agaaaggaga ggctatacat gggcaggcaa attcagatct agggacttgg         1860
caaatggatt gtacccatct agagggaaaa ataatcatag ttgcagtaca tgtagctagt         1920
ggattcatag aagcagaggt aattccacaa gagacaggaa gacagacagc actatttctg         1980
ttaaaattgg caggcagatg gcctattaca catctacaca cagataatgg tgctaacttt         2040
gcttcgcaag aagtaaagat ggttgcatgg tgggcaggga tagagcacac ctttggggta         2100
ccatacaatc cacagagtca gggagtagtg aagcaatga atcaccaccct gaaaaatcaa         2160 atagatagaa tcagggaaca agcaaattca gtagaaacca tagtattaat ggcagttcat         2220
tgcatgaatt ttaaaagaag gggaggaata ggggatatga ctccagcaga aagattaatt         2280
aacatgatca ctacagaaca agagatacaa tttcaacaat caaaaaactc aaatttaaa         2340 aattttcggg tctattacag agaaggcaga gatcaactgt ggaagggacc cggtgagcta         2400
ttgtggaaag ggaaggagc agtcatctta aaggtaggga cagacattaa ggtagtaccc         2460
agaagaaagg ctaaaattat caaagattat ggaggaggaa aagaggtgga tagcagttcc         2520
cacatggagg ataccggaga ggctagagag gtggcatagc ctcataaaat atctgaaata         2580
```

```
taaaactaaa gatctacaaa aggtttgcta tgtgccccat tttaaggtcg gatgggcatg    2640
gtggacctgc agcagagtaa tcttcccact acaggaagga agccatttag aagtacaagg    2700
gtattggcat ttgacaccag aaaaagggtg gctcagtact tatgcagtga ggataacctg    2760
gtactcaaag aacttttgga cagatgtaac accaaactat gcagacattt tactgcatag    2820
cacttatttc ccttgcttta cagcgggaga agtgagaagg gccatcaggg gagaacaact    2880
gctgtcttgc tgcaggttcc cgagagctca taagtaccag gtaccaagcc tacagtactt    2940
agcactgaaa gtag                                                      2954
```

<210> SEQ ID NO 106
<211> LENGTH: 31
<212> TYPE: DNA
<213> ORGANISM: Artificial Sequence
<220> FEATURE:
<223> OTHER INFORMATION: synthetic construct

<400> SEQUENCE: 106

```
caaaagaaaa gatagttgca ttaagagaaa t                                   31
```

<210> SEQ ID NO 107
<211> LENGTH: 22
<212> TYPE: DNA
<213> ORGANISM: Artificial Sequence
<220> FEATURE:
<223> OTHER INFORMATION: synthetic construct

<400> SEQUENCE: 107

```
gccacaattc gtaccccatc ca                                             22
```

<210> SEQ ID NO 108
<211> LENGTH: 26
<212> TYPE: DNA
<213> ORGANISM: Artificial Sequence
<220> FEATURE:
<223> OTHER INFORMATION: synthetic construct

<400> SEQUENCE: 108

```
catacaacac ccccacattt gctata                                         26
```

<210> SEQ ID NO 109
<211> LENGTH: 22
<212> TYPE: DNA
<213> ORGANISM: Artificial Sequence
<220> FEATURE:
<223> OTHER INFORMATION: synthetic construct

<400> SEQUENCE: 109

```
agtcctgcag ggtgtggtat tc                                             22
```

<210> SEQ ID NO 110
<211> LENGTH: 23
<212> TYPE: DNA
<213> ORGANISM: Artificial Sequence
<220> FEATURE:
<223> OTHER INFORMATION: synthetic construct

<400> SEQUENCE: 110

```
actcccacat ttgcyatagc gag                                            23
```

<210> SEQ ID NO 111
<211> LENGTH: 22
<212> TYPE: DNA

```
<213> ORGANISM: Artificial Sequence
<220> FEATURE:
<223> OTHER INFORMATION: synthetic construct

<400> SEQUENCE: 111
agtcctgcag ggtgtggtat tc                                            22

<210> SEQ ID NO 112
<211> LENGTH: 35
<212> TYPE: DNA
<213> ORGANISM: Artificial Sequence
<220> FEATURE:
<223> OTHER INFORMATION: synthetic construct

<400> SEQUENCE: 112
tagattttag ggaactaaat agggtcactc aggac                              35

<210> SEQ ID NO 113
<211> LENGTH: 30
<212> TYPE: DNA
<213> ORGANISM: Artificial Sequence
<220> FEATURE:
<223> OTHER INFORMATION: synthetic construct

<400> SEQUENCE: 113
atayaatact ccartatttg ctataaacag                                    30

<210> SEQ ID NO 114
<211> LENGTH: 26
<212> TYPE: DNA
<213> ORGANISM: Artificial Sequence
<220> FEATURE:
<223> OTHER INFORMATION: synthetic construct

<400> SEQUENCE: 114
tggtgtctca ttgtttrtac taggta                                        26

<210> SEQ ID NO 115
<211> LENGTH: 33
<212> TYPE: DNA
<213> ORGANISM: Artificial Sequence
<220> FEATURE:
<223> OTHER INFORMATION: synthetic construct

<400> SEQUENCE: 115
tcagtaacag tactagatgt gggagatgca tat                                33

<210> SEQ ID NO 116
<211> LENGTH: 33
<212> TYPE: DNA
<213> ORGANISM: Artificial Sequence
<220> FEATURE:
<223> OTHER INFORMATION: synthetic construct

<400> SEQUENCE: 116
tcagtaacag tactggatgt ggggatgca tat                                 33

<210> SEQ ID NO 117
<211> LENGTH: 27
<212> TYPE: DNA
<213> ORGANISM: Artificial Sequence
<220> FEATURE:
<223> OTHER INFORMATION: synthetic construct

<400> SEQUENCE: 117
caatactcca gtatttgtca taccaag                                       27
```

```
<210> SEQ ID NO 118
<211> LENGTH: 26
<212> TYPE: DNA
<213> ORGANISM: Artificial Sequence
<220> FEATURE:
<223> OTHER INFORMATION: synthetic construct

<400> SEQUENCE: 118
aacactccar tatttgcyat accaag                                          26

<210> SEQ ID NO 119
<211> LENGTH: 25
<212> TYPE: DNA
<213> ORGANISM: Artificial Sequence
<220> FEATURE:
<223> OTHER INFORMATION: synthetic construct

<400> SEQUENCE: 119
tytttaaccc tgmtgggtgt ggtat                                           25

<210> SEQ ID NO 120
<211> LENGTH: 37
<212> TYPE: DNA
<213> ORGANISM: Artificial Sequence
<220> FEATURE:
<223> OTHER INFORMATION: synthetic construct

<400> SEQUENCE: 120
tcagggarct caataaaaga actcaagact tytggga                              37

<210> SEQ ID NO 121
<211> LENGTH: 37
<212> TYPE: DNA
<213> ORGANISM: Artificial Sequence
<220> FEATURE:
<223> OTHER INFORMATION: synthetic construct

<400> SEQUENCE: 121
tcagggaact yaayaaaaga actcaagact tytggga                              37

<210> SEQ ID NO 122
<211> LENGTH: 27
<212> TYPE: DNA
<213> ORGANISM: Artificial Sequence
<220> FEATURE:
<223> OTHER INFORMATION: synthetic construct

<400> SEQUENCE: 122
yaayactcca gtatttgyca taccaag                                         27

<210> SEQ ID NO 123
<211> LENGTH: 288
<212> TYPE: PRT
<213> ORGANISM: HIV-1

<400> SEQUENCE: 123

Phe Leu Asp Gly Ile Asp Lys Ala Gln Glu Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
```

```
            50                  55                  60
Cys Thr His Leu Glu Gly Lys Val Ile Leu Val Ala Val His Val Ala
 65                  70                  75                  80

Ser Gly Tyr Ile Glu Ala Glu Val Ile Pro Ala Glu Thr Gly Gln Glu
                 85                  90                  95

Thr Ala Tyr Phe Leu Leu Lys Leu Ala Gly Arg Trp Pro Val Lys Thr
                100                 105                 110

Ile His Thr Asp Asn Gly Ser Asn Phe Thr Ser Ala Thr Val Lys Ala
                115                 120                 125

Ala Cys Trp Trp Ala Gly Ile Lys Gln Glu Phe Gly Ile Pro Tyr Asn
            130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
                180                 185                 190

Gly Tyr Ser Ala Gly Glu Arg Ile Val Asp Ile Ile Ala Thr Asp Ile
            195                 200                 205

Gln Thr Lys Glu Leu Gln Lys Gln Ile Thr Lys Ile Gln Asn Phe Arg
210                 215                 220

Val Tyr Tyr Arg Asp Ser Arg Asp Pro Leu Trp Lys Gly Pro Ala Lys
225                 230                 235                 240

Leu Leu Trp Lys Gly Glu Gly Ala Val Val Ile Gln Asp Asn Ser Glu
                245                 250                 255

Ile Lys Val Val Pro Arg Arg Lys Val Lys Ile Ile Arg Asp Tyr Gly
                260                 265                 270

Lys Gln Met Ala Gly Asp Asp Cys Val Ala Ser Arg Gln Asp Glu Asp
            275                 280                 285

<210> SEQ ID NO 124
<211> LENGTH: 28
<212> TYPE: DNA
<213> ORGANISM: Artificial Sequence
<220> FEATURE:
<223> OTHER INFORMATION: synthetic construct

<400> SEQUENCE: 124
gtgataaatg tcarytaaaa ggrgaagc                                        28

<210> SEQ ID NO 125
<211> LENGTH: 23
<212> TYPE: DNA
<213> ORGANISM: Artificial Sequence
<220> FEATURE:
<223> OTHER INFORMATION: synthetic construct

<400> SEQUENCE: 125
ctttccaaas tggrtctctg ctg                                             23

<210> SEQ ID NO 126
<211> LENGTH: 24
<212> TYPE: DNA
<213> ORGANISM: Artificial Sequence
<220> FEATURE:
<223> OTHER INFORMATION: synthetic construct

<400> SEQUENCE: 126
catggacaag tagactgtag ycca                                            24
```

<210> SEQ ID NO 127
<211> LENGTH: 27
<212> TYPE: DNA
<213> ORGANISM: Artificial Sequence
<220> FEATURE:
<223> OTHER INFORMATION: synthetic construct

<400> SEQUENCE: 127
gtccctgtaa taaacycgaa aattttg                                       27

<210> SEQ ID NO 128
<211> LENGTH: 29
<212> TYPE: DNA
<213> ORGANISM: Artificial Sequence
<220> FEATURE:
<223> OTHER INFORMATION: synthetic construct

<400> SEQUENCE: 128
ctytrgtytg tatgtctgtt gctatyatg                                     29

<210> SEQ ID NO 129
<211> LENGTH: 24
<212> TYPE: DNA
<213> ORGANISM: Artificial Sequence
<220> FEATURE:
<223> OTHER INFORMATION: synthetic construct

<400> SEQUENCE: 129
cagcytgmtc tcttacytgt ccta                                          24

<210> SEQ ID NO 130
<211> LENGTH: 25
<212> TYPE: DNA
<213> ORGANISM: Artificial Sequence
<220> FEATURE:
<223> OTHER INFORMATION: synthetic construct

<400> SEQUENCE: 130
ctaytattct ttcycctgca ctgta                                         25

<210> SEQ ID NO 131
<211> LENGTH: 36
<212> TYPE: DNA
<213> ORGANISM: Artificial Sequence
<220> FEATURE:
<223> OTHER INFORMATION: synthetic construct

<400> SEQUENCE: 131
tcaagctgaa catctyaara cagcagtaca ratggc                             36

<210> SEQ ID NO 132
<211> LENGTH: 36
<212> TYPE: DNA
<213> ORGANISM: Artificial Sequence
<220> FEATURE:
<223> OTHER INFORMATION: synthetic construct

<400> SEQUENCE: 132
tcaggctgaa catctyaara cagcagtaca ratggc                             36

<210> SEQ ID NO 133
<211> LENGTH: 20
<212> TYPE: DNA
<213> ORGANISM: Artificial Sequence
<220> FEATURE:

<223> OTHER INFORMATION: synthetic construct

<400> SEQUENCE: 133
gtgggcrggr atcaarctga                    20

<210> SEQ ID NO 134
<211> LENGTH: 23
<212> TYPE: DNA
<213> ORGANISM: Artificial Sequence
<220> FEATURE:
<223> OTHER INFORMATION: synthetic construct

<400> SEQUENCE: 134
ggcrggratc aagcagraat cta                23

<210> SEQ ID NO 135
<211> LENGTH: 25
<212> TYPE: DNA
<213> ORGANISM: Artificial Sequence
<220> FEATURE:
<223> OTHER INFORMATION: synthetic construct

<400> SEQUENCE: 135
gtagccagtg gatayataga agcag              25

<210> SEQ ID NO 136
<211> LENGTH: 27
<212> TYPE: DNA
<213> ORGANISM: Artificial Sequence
<220> FEATURE:
<223> OTHER INFORMATION: synthetic construct

<400> SEQUENCE: 136
gtccctgtaa taaacycgaa aattttg             27

<210> SEQ ID NO 137
<211> LENGTH: 32
<212> TYPE: DNA
<213> ORGANISM: Artificial Sequence
<220> FEATURE:
<223> OTHER INFORMATION: synthetic construct

<400> SEQUENCE: 137
acctgtccta taattttctt taattcyttc tg        32

<210> SEQ ID NO 138
<211> LENGTH: 27
<212> TYPE: DNA
<213> ORGANISM: Artificial Sequence
<220> FEATURE:
<223> OTHER INFORMATION: synthetic construct

<400> SEQUENCE: 138
ctttattcat agattctact acycgtc             27

<210> SEQ ID NO 139
<211> LENGTH: 34
<212> TYPE: DNA
<213> ORGANISM: Artificial Sequence
<220> FEATURE:
<223> OTHER INFORMATION: synthetic construct

<400> SEQUENCE: 139
ctttaattct ttattcatag attctactac ycga      34

```
<210> SEQ ID NO 140
<211> LENGTH: 43
<212> TYPE: DNA
<213> ORGANISM: Artificial Sequence
<220> FEATURE:
<223> OTHER INFORMATION: synthetic construct

<400> SEQUENCE: 140
tcttaaaatt agcaggaaga tggccagtra maacaataca tac          43

<210> SEQ ID NO 141
<211> LENGTH: 43
<212> TYPE: DNA
<213> ORGANISM: Artificial Sequence
<220> FEATURE:
<223> OTHER INFORMATION: synthetic construct

<400> SEQUENCE: 141
ttttaaaact agcaggaaga tggccagtra maacaataca tac          43
```

REAL-TIME PCR POINT MUTATION ASSAYS FOR DETECTING HIV-1 RESISTANCE TO ANTIVIRAL DRUGS

CROSS-REFERENCE TO RELATED APPLICATIONS

This application depends from and claims priority to U.S. Provisional Application No. 61/443,926 filed Feb. 17, 2011, the entire contents of which are incorporated herein by reference.

GOVERNMENT INTEREST

The invention described herein may be manufactured, used, and licensed by or for the United States Government.

BACKGROUND OF THE INVENTION

The HIV pandemic now exceeds 40 million persons and its expansion is being met with an increased use of anti-HIV drugs to care for the lives of those affected. Emergence of drug resistance is expected to increase as the use of these drugs for the clinical management of HIV-1 infected persons increases worldwide. Highly active antiretroviral therapy (HAART) containing a combination of three antiretroviral drugs is currently recommended and has been effective in reducing mortality and morbidity. Four classes of drugs are available that inhibit either virion entry (e.g., T-20), nucleotide extension by viral reverse transcriptase (e.g., 3TC, d4T), reverse transcriptase enzymatic activity (e.g., nevirapine, efavirenz), or the viral protease (e.g., nelfinavir, lopinavir). Drug resistance that is conferred by mutations is frequently selected in viruses from patients failing antiretroviral therapy and is considered a major cause of treatment failure.

Current treatment guidelines recommend baseline drug resistance testing for the selection of optimal drug regimens for patients initiating antiretroviral therapy. Accurate identification of any resistant viruses the person carries will help guide the selection of treatment regimens with fully active drugs. Drug resistance testing is performed through the use of phenotypic or genotypic assays. Phenotypic assays measure drug susceptibilities of patient-derived viruses and provide direct evidence of drug resistance. However, phenotypic assays are culture-based, complex, laborious, and costly. Genotypic assays are frequently used to detect mutations associated with drug resistance by sequence analysis of the viral RNA from plasma. These assays are also complex and are insensitive to the detection of low levels of mutants, such as what might be present early in the emergence of resistance or which might persist at low set points in the absence of treatment. Commonly-used sequencing methods do not reliably detect mutants present at levels below 20-30% of the total viral population within a sample. Described in this application are PCR-based drug resistance detection assays that are able to detect drug-resistant viruses present at frequencies as low as 0.5%-0.04% within the plasma of infected persons. These sensitivities are 40-500-times greater than what has been achieved by conventional sequence testing.

Although drug resistance is frequently seen in patients failing antiretroviral therapy, a substantial prevalence (~8-25%) of transmitted drug-resistant HIV-1 is found among drug-naïve populations, supporting the need for baseline drug resistant testing. Because drug-resistant mutants are generally less fit than wild type viruses in the absence of drug, many drug-resistance mutations revert back to wild-type over time and become gradually undetectable in plasma. However, the drug-resistant viruses that become undetectable in plasma remain archived in the patients and are re-selected when drugs are used. Therefore, it is important to have sensitive assays that can accurately detect the presence of low frequency drug-resistant mutants. Data from the use of the sensitive real-time PCR assays described in this patent application demonstrate clearly that conventional sequencing of drug-naïve persons underestimates the prevalence of transmitted drug resistance (Johnson et al., 13th HDR Workshop, Tenerife, Spain, 2004). Testing transmitted drug resistant viruses for additional mutations by the sensitive assays identified new mutants that increased the prevalence of resistance within the population by another 2 to 8%. The increases imply that drug resistance mutations are transmitted at frequencies 20-80% higher than previously reported. Therefore, these data demonstrate the poorer sensitivity of sequencing methods for baseline drug resistance testing.

Drug resistance testing is also indicated for patients receiving HAART to manage treatment failures and to help guide the selection of new HAART regimens with active drugs. Recent data have pointed to the importance of sensitive drug resistance assays for this testing and associate low-frequency drug-resistant viruses that are not detectable by conventional sequencing with poor treatment outcomes (Mellors et al., 11th CROI, 2004; Jourdain et al., JID 2004) (1). These studies reported that persons exposed to a non-nucleoside reverse transcriptase inhibitor (NNRTI) who generated resistance mutations detectable only by sensitive assays, and not by conventional sequencing, respond more poorly to subsequent NNRTI-containing regimens. Data from the subtype C HIV-1 assays reported herein show that more than one-third of the drug-resistant viruses that emerge from intrapartum single-dose nevirapine intervention are not identified by conventional population sequencing (Johnson et al., 12th CROI 2005). The detection of the substantial numbers of low-frequency drug-resistant viruses will be important for selecting a regimen with fully active drugs.

In clinical monitoring of treated persons, the greater sensitivity of the present real-time PCR resistance assays over conventional sequencing may allow earlier detection of resistance mutations that emerge during treatment and provide advance notice of possible declines in response to therapy. Early detection will help guide clinicians in modifying drug regimens in an effort to prevent treatment failure and the emergence of high-level drug resistance. Methods with greater sensitivity in detecting low levels of resistant virus, below what is capable by conventional sequence analysis, are important for improving clinical management of patients under HAART. The substantially higher sensitivity, the simplicity, the high throughput capability, and the low cost of the present real-time PCR drug resistance assays are all advantages over conventional sequence analysis.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Disclosed are compositions including primers and probes, which are capable of interacting with the disclosed nucleic acids, such as the nucleic acids encoding the reverse transcriptase, protease, or integrase of HIV as disclosed herein and methods of highly sensitive mutation specific detection of drug resistant HIV in biological samples. Thus, provided is an oligonucleotide comprising any one of the nucleotide sequences set forth in SEQ ID NOS:1-89, 96-122, and 124-141. Also provided is an oligonucleotide consisting of any of the nucleotide sequences set forth in SEQ ID NOS: 1-89, 96-122, and 124-141. Each of the disclosed oligonucleotides is a probe or a primer. Also provided are mixtures of primers and mixtures of primers and probes and for use in RT-PCR and primary PCR reactions disclosed herein. Kits comprising the primers or probes are provided. Provided are methods for the specific detection of several mutations in HIV. Mutations in the reverse transcriptase, protease, and integrase of HIV can be detected using the methods described herein.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process is described as an order of individual steps or using specific materials, it is appreciated that described steps or materials may be interchangeable such that the description of the invention includes multiple parts or steps arranged in many ways as is readily appreciated by one of skill in the art.

Figure 1:
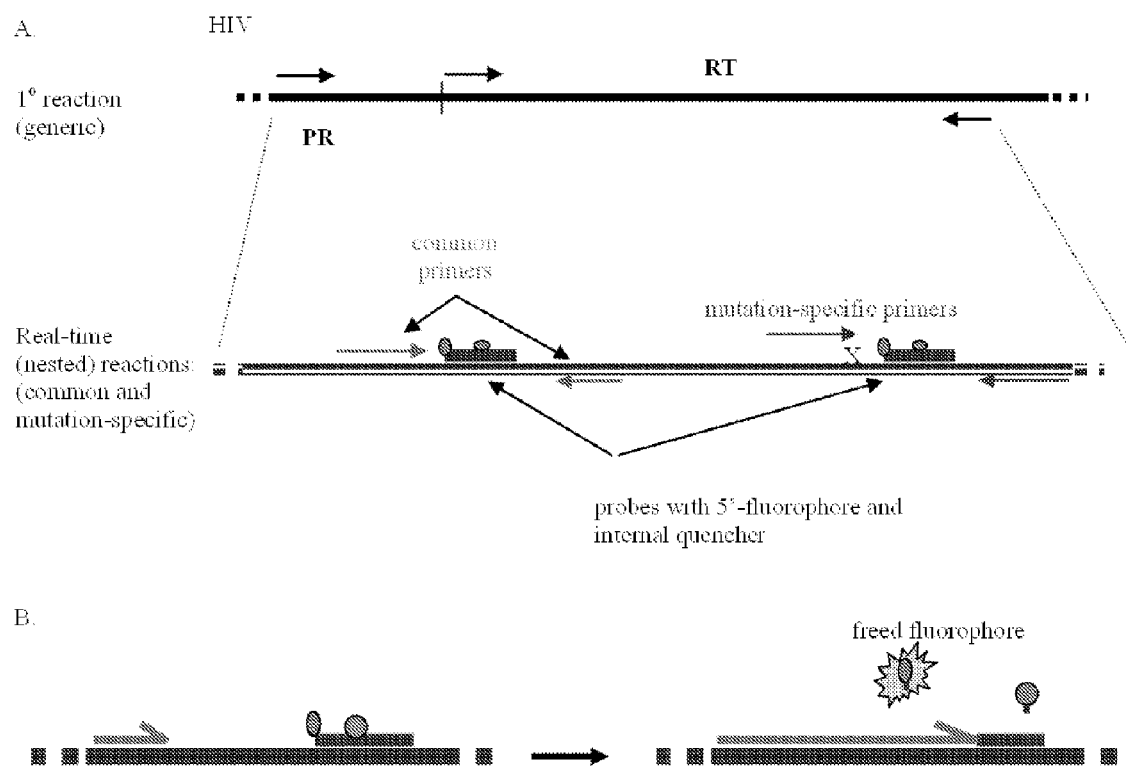
FIGS. 1A and 1B are schematic illustrations of the principle of the present assay.

In an effort to improve the detection of mutations associated with HIV-1 drug resistance, provided are PCR-based point mutation assays. The present methodology allows testing for different point mutations in patient samples at an achievable sensitivity of 1-2 log greater than conventional sequencing. As such, the invention has utility to detect the presence or absence of a drug-resistant strain of HIV. The principle of the present assay is to compare the differential amplifications of a mutation-specific PCR and a total copy (common) PCR, which detects all sequences present. The assay can use template generated from RT-PCR of viral RNA or from PCR of proviral DNA from infected cells (FIG. 1).

Two important HIV-1 reverse transcriptase mutations that significantly compromise the success of treatment with reverse transcriptase inhibitors are 103N and 184V. The 103N mutation is frequently selected in patients failing treatment with non-nucleoside RT inhibitors (e.g., nevirapine, efavirenz). Likewise, the frequent appearance of the 184V mutation following exposure to nucleoside inhibitors lamivudine (3TC), emtricitabine (FTC), and abacavir, and it's seemingly rapid disappearance after discontinuation of therapy, makes accurate measure of rapidly decaying mutations important for surveillance and clinical management.

The simplicity, greater sensitivity, and high-throughput capabilities of the present real-time PCR methodology make it useful for screening large numbers of samples, which allows the implementation of universal resistance testing and protracted surveillance of resistance mutations The methods disclosed herein have multiple applications including (1) resistance testing for clinical management of HIV-infected persons receiving anti-HIV drugs (for detecting emergence of resistant viruses in treated persons, and as a pre-treatment evaluation of patient baseline HIV in order to tailor the most appropriate drug combination), (2) use in blood bank screening as a nucleic acid test (NAT), due to the high sensitivity and high throughput capability of the assays, (3) the ability to measure plasma viral loads, since the assays are inherently quantitative, (4) use as a screening tool for monitoring the spread of resistant HIV, (5) use as a research tool to study the emergence and biology of drug resistance mutations, (6) detection of resistance mutations in both subtype 13 and non-B subtypes of HIV-1, (7) possible detection of resistance mutations in HIV-2, and (8) identification of specific panels of mutations that are designed to address each of the described uses. The reagents and specific usages developed here are unique.

As used in the specification and the appended claims, the singular forms "a," "an" and "the" include plural referents unless the context clearly dictates otherwise. Thus, for example, reference to "a primer" includes mixtures of two or more such primers, and the like.

Compositions

Disclosed are compositions including primers and probes, which are capable of interacting with the disclosed nucleic acids, such as the nucleic acids encoding the reverse transcriptase or protease of HIV as disclosed herein and in the literature.

Thus, provided is an oligonucleotide comprising a nucleotide sequence as set forth in any of SEQ ID NOS:1-89, 96-122, and 124-141. Also provided is an oligonucleotide consisting of any one of the nucleotide sequences set forth in SEQ ID NOS: 1-89, 96-122, and 124-141. Thus, provided is an oligonucleotide comprising the sequence selected from the group consisting of the nucleotides as set forth in the sequence listing as SEQ ID NOS: 1-89, 96-122, and 124-141. Each of the disclosed oligonucleotides is a probe or a primer. Each can be used independently of the others in an amplification method or in a hybridization/probing method. One or more of the probes or primers can be used together in the compositions and methods for detecting mutations. Specific examples of such compositions and methods are described herein.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose.

The phosphate moiety of a nucleotide is pentavalent phosphate. A non-limiting example of a nucleotide would be 3'-AMP (3'-adenosine monophosphate) or 5'-GMP (5'-guanosine monophosphate). The term "nucleotide" includes nucleotides and nucleotide analogs, preferably groups of nucleotides comprising oligonucleotides, and refers to any compound containing a heterocyclic compound bound to a phosphorylated sugar by an N-glycosyl link or any monomer capable of complementary base pairing or any polymer capable of hybridizing to an oligonucleotide.

The term "nucleotide analog" refers to molecules that can be used in place of naturally occurring bases in nucleic acid synthesis and processing, preferably enzymatic as well as chemical synthesis and processing, particularly modified nucleotides capable of base pairing. A nucleotide analog is a nucleotide which contains some type of modification to one of the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and nonnucleotide bridges such as polyethylene glycol, aromatic polyamides and lipids. Optionally, nucleotide analog is a synthetic base that does not comprise adenine, guanine, cytosine, thymidine, uracil or minor bases. These and other nucleotide and nucleoside derivatives, analogs and backbone modifications are known in the art (e.g., Piccirilli J. A. et al. (1990) Nature 343:33-37; Sanghvi et al (1993) In: Nucleosides and Nucleotides as Antitumor and Antiviral Agents, (Eds. C. K. Chu and D. C. Baker) Plenum, New York, pp. 311-323; Goodchild J. (1990) Bioconjugate Chemistry 1:165-187; Beaucage et al. (1993) Tetrahedron 49:1925-1963).

Nucleotide substitutes include molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

There are a variety of molecules disclosed herein that are nucleic acid based. The disclosed nucleic acids are made up of for example, nucleotides, nucleotide analogs, or nucleotide substitutes. Non-limiting examples of these and other molecules are discussed herein.

The term "oligonucleotide" means a naturally occurring or synthetic polymer of nucleotides, preferably a polymer comprising at least three nucleotides and more preferably a polymer capable of hybridization. Oligonucleotides may be single-stranded, double-stranded, partially single-stranded or partially double-stranded ribonucleic or deoxyribonucleic acids, including selected nucleic acid sequences, heteroduplexes, chimeric and hybridized nucleotides and oligonucleotides conjugated to one or more nonoligonucleotide molecules. In general, the nucleotides comprising a oligonucleotide are naturally occurring deoxyribonucleotides, such as adenine, cytosine, guanine or thymine linked to 2'-deoxyribose, or ribonucleotides such as adenine, cytosine, guanine or uracil linked to ribose. However, an oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22:5220-5234 (1994); Jellinek et al., Biochemistry 34:11363-11372 (1995); Pagratis et al., Nature Biotechnol. 15:68-73 (1997), each of which is incorporated herein by reference).

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22:5220-5234 (1994); Jellinek et al., Biochemistry 34:11363-11372 (1995); Pagratis et al., Nature Biotechnol. 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. 22:977-986 (1994); Ecker and Crooke, BioTechnology 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation. Functional analogs of naturally occurring polynucleotides can bind to RNA or DNA, and include peptide nucleic acid (PNA) molecules.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

The oligonucleotides of SEQ ID NOS:1-89, 96-122, and 124-141 can be modified in insubstantial ways and yet retain substantially the same hybridization strength and specificity as described herein. These parameters are easily measured in assays such as those taught herein. Thus, one of skill in the art will be able to envision a number of nucleotide substitutions to the disclosed sequences, so long as they retain 80% sequence similarity with the specifically disclosed sequence. Primers and probes of the invention can include sequences having at least 85%, 90%, 95%, 96%, 97%, 98% or 99% similarity to one of SEQ ID NOS:1-89, 96-122, and 124-141 are envisioned. More specifically, primers and probes with substitutions based on known sequences of the HIV-1 protease, reverse transcriptase, or integrase are envisioned because these alternative sequences are envisioned by the person of skill in this art.

In certain embodiments the primers are used to support DNA amplification reactions. Typically the primers are capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The disclosed primers and or probes are suitable to hybridize to a target nucleic acid sequence under conditions suitable for a polymerase chain reaction. Such conditions are considered herein to hybridize under stringent conditions. As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, 95%, or more, base pair matches to each other typically remain hybridized to each other. Illustrative hybridization conditions are described in, for example but not limited to, Current Protocols in Molecular Biology, John Wiley & Sons, N.Y. (1989), 6.3.1 6.3.6.; Basic Methods in Molecular Biology, Elsevier Science Publishing Co., Inc., N.Y. (1986), pp. 75 78, and 84 87; and Molecular Cloning, Cold Spring Harbor Laboratory, N.Y. (1982), pp. 387 389, and are well known to those skilled in the art. A non-limiting example of stringent hybridization conditions is hybridization in 6× sodium chloride/sodium citrate (SSC), 0.5% SDS at about 60° C. followed by one or more washes in 2×SSC, 0.5% SDS at room temperature. Another non-limiting example of stringent hybridization conditions is hybridization in 6×SSC at about 45° C. followed by one or more washes in 0.2×SSC, 0.1% SDS at 50 to 65° C. Other stringent hybridization conditions will be evident to one of ordinary skill in the art based on general knowledge in the art as well as this specification.

An "isolated" or "purified" nucleotide or oligonucleotide is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1%, (by dry weight) of contaminating material. When nucleotide/oligonucleotide is produced by chemical synthesis, it is optionally substantially free of chemical precursors or other chemicals, i.e., it is separated from chemical precursors or other chemicals which are involved in the synthesis of the molecule. Accordingly, such preparations of the nucleotide/oligonucleotide have less than about 30%, 20%, 10%, 5% (by dry weight) of chemical precursors or compounds other than the nucleotide/oligonucleotide of interest. In some embodiments of the present invention, a nucleotide/oligonucleotide is isolated or purified.

As used herein, the term "sample" is a portion of a larger source. A sample is optionally a solid, gaseous, or fluidic sample. A sample is illustratively an environmental or biological sample. An environmental sample is illustratively, but not limited to, water, sewage, soil, or air. A "biological sample" is as sample obtained from a biological organism, a tissue, cell, cell culture medium, or any medium suitable for mimicking biological conditions. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions, throat or nasal materials. In some embodiments, target agents are contained in: CSF; serum; whole blood; throat fluid; nasopharyngeal fluid; or other respiratory fluid.

As used herein, the term "medium" refers to any liquid or fluid sample in the presence or absence of a bacterium. A medium is illustratively a solid sample that has been suspended, solubilized, or otherwise combined with fluid to form a fluidic sample. Non-limiting examples include buffered saline solution, cell culture medium, acetonitrile, trifluoroacetic acid, combinations thereof, or any other fluid recognized in the art as suitable for combination with bacteria or other cells, or for dilution of a biological sample or amplification product for analysis.

The oligonucleotides described herein include primers and probes optionally effective for cross subtype reactive PCR, as such, they are capable of detecting mutations in a variety of HIV subtypes. The following primers and probes can also include additions known to those skilled in the art.

Examples of such additions include, but are not limited to, molecules for linking the primer to a substrate, and the like. Furthermore, if desired, a nucleic acid molecule of the invention can incorporate a detectable moiety. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to a molecular probe. Common fluorescent moieties include: fluorescein, cyanine dyes, coumarins, phycoerythrin, phycobiliproteins, dansyl chloride, Texas Red, and lanthanide complexes.

Provided are the following: An oligonucleotide comprising the nucleotides as set forth in SEQ ID NO: 1; An oligonucleotide comprising the nucleotides as set forth in SEQ ID NO:2. An oligonucleotide comprising the nucleotides as set forth in SEQ ID NO: 3; An oligonucleotide comprising the nucleotides as set forth in SEQ ID NO: 4; An oligonucleotide comprising the nucleotides as set forth in SEQ ID NO: 5; An oligonucleotide comprising the nucleotides as set forth in SEQ ID NO: 6; An oligonucleotide comprising the nucleotides as set forth in SEQ ID NO: 7; An oligonucleotide comprising the nucleotides as set forth in SEQ ID NO: 8; An oligonucleotide comprising the nucleotides as set forth in SEQ ID NO: 9; An oligonucleotide comprising the nucleotides as set forth in SEQ ID NO:10. An oligonucleotide comprising the nucleotides as set forth in SEQ ID NO:11; An oligonucleotide comprising the nucleotides as set forth in SEQ ID NO:12; An oligonucleotide comprising the nucleotides as set forth in SEQ ID NO:13; An oligonucleotide comprising the nucleotides as set forth in SEQ ID NO:14; An oligonucleotide comprising the nucleotides as set forth in SEQ ID NO:15; An oligonucleotide comprising the nucleotides as set forth in SEQ ID NO:16; An oligonucleotide comprising the nucleotides as set forth in SEQ ID NO:17; An oligonucleotide comprising the nucleotides as set forth in SEQ ID NO:18; An oligonucleotide comprising the nucleotides as set forth in SEQ ID NO:19; An oligonucleotide comprising the nucleotides as set forth in SEQ ID NO:20; An oligonucleotide comprising the nucleotides as set forth in SEQ ID NO:21; An oligonucleotide comprising the nucleotides as set forth in SEQ ID NO:22; An oligonucleotide comprising the nucleotides as set forth in SEQ ID NO:23; An oligonucleotide comprising the nucleotides as set forth in SEQ ID NO: 24; An oligonucleotide comprising the nucleotides as set forth in SEQ ID NO: 25; An oligonucleotide comprising the nucleotides as set forth in SEQ ID NO: 26; An oligonucleotide comprising the nucleotides as set forth in SEQ ID NO: 27; An oligonucleotide comprising the nucleotides as set forth in SEQ ID NO: 28; An oligonucleotide comprising the nucleotides as set forth in SEQ ID NO: 29; An oligonucleotide comprising the nucleotides as set forth in SEQ ID NO: 30; An oligonucleotide comprising the nucleotides as set forth in SEQ ID NO:31; An oligonucleotide comprising the nucleotides as set forth in SEQ ID NO:32; An oligonucleotide comprising the nucleotides as set forth in SEQ ID NO:33; An oligonucleotide comprising the nucleotides as set forth in SEQ ID NO:34; An oligonucleotide comprising the nucleotides as set forth in SEQ ID NO:35; An oligonucleotide comprising the nucleotides as set forth in SEQ ID NO: 36; An oligonucleotide comprising the nucleotides as set forth in SEQ ID NO:37; An oligonucleotide comprising the nucleotides as set forth in SEQ ID NO:38; An oligonucleotide comprising the nucleotides as set forth in SEQ ID NO:39; An oligonucleotide comprising the nucleotides as set forth in SEQ ID NO:40; An oligonucleotide comprising the nucleotides as set forth in SEQ ID NO:41; An oligonucleotide comprising the nucleotides as set forth in SEQ ID NO:42; An oligonucleotide comprising the nucleotides as set forth in SEQ ID NO:43; An oligonucleotide comprising the nucleotides as set forth in SEQ ID NO:44; An oligonucleotide comprising the nucleotides as set forth in SEQ ID NO:45; An oligonucleotide comprising the nucleotides as set forth in SEQ ID NO:46. An oligonucleotide comprising the nucleotides as set forth in SEQ ID NO:47; An oligonucleotide comprising the nucleotides as set forth in SEQ ID NO:48; An oligonucleotide comprising the nucleotides as set forth in SEQ ID NO:49; An oligonucleotide comprising the nucleotides as set forth in SEQ ID NO:50; An oligonucleotide comprising the nucleotides as set forth in SEQ ID NO:51; An oligonucleotide comprising the nucleotides as set forth in SEQ ID NO:52; An oligonucleotide comprising the nucleotides as set forth in SEQ ID NO:53; An oligonucleotide comprising the nucleotides as set forth in SEQ ID NO:54; An oligonucleotide comprising the nucleotides as set forth in SEQ ID NO:55; An oligonucleotide comprising the nucleotides as set forth in SEQ ID NO:56; An oligonucleotide comprising the nucleotides as set forth in SEQ ID NO:57; An oligonucleotide comprising the nucleotides as set forth in SEQ ID NO:58; An oligonucleotide comprising the nucleotides as set forth in SEQ ID NO:59; An oligonucleotide comprising the nucleotides as set forth in SEQ ID NO:60; An oligonucleotide comprising the nucleotides as set forth in SEQ ID NO:61; An oligonucleotide comprising the nucleotides as set forth in SEQ ID NO:62; An oligonucleotide comprising the nucleotides as set forth in SEQ ID NO: 63; An oligonucleotide comprising the nucleotides as set forth in SEQ ID NO: 64; An oligonucleotide comprising the nucleotides as set forth in SEQ ID NO:65; An oligonucleotide comprising the nucleotides as set forth in SEQ ID NO:66; An oligonucleotide comprising the nucleotides as set forth in SEQ ID NO:67; An oligonucleotide comprising the nucleotides as set forth in SEQ ID NO:68; An oligonucleotide comprising the nucleotides as set forth in SEQ ID NO:69; An oligonucleotide comprising the nucleotides as set forth in SEQ ID NO:70; An oligonucleotide comprising the nucleotides as set forth in SEQ ID NO:71; An oligonucleotide comprising the nucleotides as set forth in SEQ ID NO:72; An oligonucleotide comprising the nucleotides as set forth in SEQ ID NO:73; An oligonucleotide comprising the nucleotides as set forth in SEQ ID NO:74; An oligonucleotide comprising the nucleotides as set forth in SEQ ID NO:75; An oligonucleotide comprising the nucleotides as set forth in SEQ ID NO:76; An oligonucleotide comprising the nucleotides as set forth in SEQ ID NO:77; An oligonucleotide comprising the nucleotides as set forth in SEQ ID NO:78; An oligonucleotide comprising the nucleotides as set forth in SEQ ID NO:79; An oligonucleotide comprising the nucleotides as set forth in SEQ ID NO:80; An oligonucleotide comprising the nucleotides as set forth in SEQ ID NO:81; An oligonucleotide comprising the nucleotides as set forth in SEQ ID NO:82; An oligonucleotide comprising the nucleotides as set forth in SEQ ID NO:83; An oligonucleotide comprising the nucleotides as set forth in SEQ ID NO:84; An oligonucleotide comprising the nucleotides as set forth in SEQ ID NO: 85; An oligonucleotide comprising the nucleotides as set forth in SEQ ID NO:86; An oligonucleotide comprising the nucleotides as set forth in SEQ ID NO:87; An oligonucleotide comprising the nucleotides as set forth in SEQ ID NO:88; An oligonucleotide comprising the nucleotides as set forth in SEQ ID NO:89; An oligonucleotide comprising the nucleotides as set forth in SEQ ID NO:96; An oligonucleotide comprising the nucleotides as set forth in SEQ ID NO: 97; An oligonucleotide comprising the nucleotides as set forth in SEQ ID NO:98; An oligonucleotide comprising the nucleotides as set forth in SEQ ID NO:99; An oligonucleotide comprising the nucleotides as set forth in SEQ ID NO:100; An oligonucleotide comprising the nucleotides as set forth in SEQ ID NO:101; An oligonucleotide comprising the nucleotides as set forth in SEQ ID NO:102; An oligonucleotide comprising the nucleotides as set forth in SEQ ID NO:103; An oligonucleotide comprising the nucleotides as set forth in SEQ ID NO:104; An oligonucleotide comprising the nucleotides as set forth in SEQ ID NO:113; An oligonucleotide comprising the nucleotides as set forth in SEQ ID NO:114; An oligonucleotide comprising the nucleotides as set forth in SEQ ID NO:115; An oligonucleotide comprising the nucleotides as set forth in SEQ ID NO:116; An oligonucleotide comprising the nucleotides as set forth in SEQ ID NO:117; An oligonucleotide comprising the nucleotides as set forth in SEQ ID NO:118; An oligonucleotide comprising the nucleotides as set forth in SEQ ID NO:119; An oligonucleotide comprising the nucleotides as set forth in SEQ ID NO:120; An oligonucleotide comprising the nucleotides as set forth in SEQ ID NO:121; An oligonucleotide comprising the nucleotides as set forth in SEQ ID NO:122; An oligonucleotide comprising the nucleotides as set forth in SEQ ID NO:124; An oligonucleotide comprising the nucleotides as set forth in SEQ ID NO:125; An oligonucleotide comprising the nucleotides as set forth in SEQ ID NO:126; An oligonucleotide comprising the nucleotides as set forth in SEQ ID NO:127; An oligonucleotide comprising the nucleotides as set forth in SEQ ID NO:128; An oligonucleotide comprising the nucleotides as set forth in SEQ ID NO:129; An oligonucleotide comprising the nucleotides as set forth in SEQ ID NO:130; An oligonucleotide comprising the nucleotides as set forth in SEQ ID NO:131; An oligonucleotide comprising the nucleotides as set forth in SEQ ID NO:132; An oligonucleotide comprising the nucleotides as set forth in SEQ ID NO:133; An oligonucleotide comprising the nucleotides as set forth in SEQ ID NO:134; An oligonucleotide comprising the nucleotides as set forth in SEQ ID NO:135; An oligonucleotide comprising the nucleotides as set forth in SEQ ID NO:136; An oligonucleotide comprising the nucleotides as set forth in SEQ ID NO:137; An oligonucleotide comprising the nucleotides as set forth in SEQ ID NO:138; An oligonucleotide comprising the nucleotides as set forth in SEQ ID NO:139; An oligonucleotide comprising the nucleotides as set forth in SEQ ID NO:141; and an oligonucleotide comprising the nucleotides as set forth in SEQ ID NO:141. Thus, provided is an oligonucleotide comprising the sequence selected from group consisting of the nucleotides as set forth in the sequence listing as SEQ ID NO:1-89, 96-104, 113-122; and 124-141.

Also provided are mixtures of primers for use in RT-PCR and primary PCR reactions disclosed herein. Thus, a mixture of primers comprising SEQ ID NO:1 and 3 is provided. This mixture can be used for the reverse transcription-PCR (RT-PCR) reaction and the primary PCR reaction for HIV. It reverse transcribes and amplifies the HIV protease region comprising positions 30 and 90 in addition to the region of the reverse transcriptase gene comprising the mutations described herein.

Provided is a mixture of primers comprising SEQ ID NOS: 2 and 3. This mixture does not reverse transcribe or amplify the protease regions of interest, but is useful for the analysis of the reverse transcriptase.

A mixture of primers comprising SEQ ID NOS: 4 and 6 is provided. This mixture is for the RT-PCR and primary PCR reactions for HIV. It also reverse transcribes and amplifies the HIV protease region comprising positions 30 and 90 in addition to the region of the reverse transcriptase gene comprising the mutations described herein.

Also provided is a mixture of primers comprising SEQ ID NOS: 5 and 6. This mixture does not reverse transcribe or amplify the protease regions of interest, but is useful for the analysis of the reverse transcriptase.

A mixture of primers comprising SEQ ID NOS: 124 and 125 is provided. This mixture is for the RT-PCR and primary PCR reactions for HIV. It also reverse transcribes and amplifies the HIV integrase region comprising positions 138, 140, 148, and 155.

Also provided is a mixture of primers comprising SEQ ID NOS: 127 and 128. This mixture does not reverse transcribe or amplify the protease regions of interest, but is useful for the analysis of the reverse transcriptase.

Provided are oligonucleotide mixtures for use in the mutation-specific PCR reactions disclosed herein. Detection can be achieved so long as any of the disclosed forward primers are paired with any of the reverse primers for a given mutation.

Thus, provided is a mixture of primers comprising one or more primers selected from the group consisting of SEQ ID NOS:22, 23, 24 and 25. This is a forward primer mixture for the 103N mutation-specific PCR reaction. The mixture can further include a reverse primer. For example, the reverse primer can be a primer consisting of SEQ ID NO:26.

Also provided is a mixture of primers comprising one or more primers selected from the group consisting of SEQ ID NOS: 59, 60 and 61. This is a forward primer mixture for the 103N mutation-specific PCR reaction. The mixture can further include a reverse primer. For example, the reverse primer can be a primer consisting of SEQ ID NO:26.

A mixture of primers comprising one or more primers selected from the group consisting of SEQ ID NOS:33, 34 and 35 is provided. This is a forward primer mixture for the 184V mutation-specific PCR reaction. The mixture can further include a reverse primer. For example, the reverse primer can be a primer comprising or consisting of SEQ ID NO:36.

A mixture of primers comprising one or more primers selected from the group consisting of SEQ ID NOS:88, 89, 102, 103, and 104 is provided. This is a forward primer mixture for the 184V mutation-specific PCR reaction. The mixture can further include a reverse primer. For example, the reverse primer can be a primer comprising or consisting of SEQ ID NO:85.

A mixture of primers comprising one or more primers selected from the group consisting of SEQ ID NOS:62, 63, 64, 65, 96 and 97 is provided. This is a forward primer mixture for the 41L mutation-specific PCR reaction. The mixture can further include a reverse primer. For example, the reverse primer can be a primer comprising or consisting of SEQ ID NO:66.

A mixture of primers comprising SEQ ID NOS: 10 and 98 and a reverse primer is provided. This mixture includes a forward primer for the 65R mutation-specific PCR reaction.

The reverse primer can, for example, be a primer comprising or consisting of SEQ ID NO:11.

A mixture of primers comprising SEQ ID NOS: 113 and a reverse primer is provided. This mixture includes a forward primer for the 65R mutation-specific PCR reaction. The reverse primer can, for example, be a primer comprising or consisting of SEQ ID NO:114.

A mixture of primers comprising SEQ ID NOS: 117 and 118 and a reverse primer is provided. This mixture includes a forward primer for the 65R mutation-specific PCR reaction. The reverse primer can, for example, be a primer comprising or consisting of SEQ ID NO:119.

A mixture of primers comprising SEQ ID NOS: 117, 118, 122, and a reverse primer is provided. This mixture includes a forward primer for the 65R mutation-specific PCR reaction. The reverse primer can, for example, be a primer comprising or consisting of SEQ ID NO:119.

A mixture of primers comprising SEQ ID NOS: 69 and 70 is provided. This is a forward primer mixture for the 67N mutation-specific PCR reaction. The mixture can further include a reverse primer. For example, the reverse primer can be a primer comprising or consisting of SEQ ID NO:8.

A mixture of primers comprising one or more primers selected from the group consisting of SEQ ID NOS:12, 13, and 71 is provided. This is a forward primer mixture for the 69T specific PCR reaction. The mixture can further include a reverse primer. For example, the reverse primer can be a primer comprising or consisting of SEQ ID NOS:8 and 14.

A mixture of primers comprising one or more primers selected from the group consisting of SEQ ID NOS:2, 16, 17, 18, 19, and 100 is provided. This is a forward primer mixture for the 70R mutation-specific PCR reaction. The mixture can further include a reverse primer. For example, the reverse primer can be a primer comprising or consisting of SEQ ID NOS:20, 72, or 73.

A mixture of primers comprising SEQ ID NOS:28 and 29 is provided. This is a forward primer mixture for the 181C mutation-specific PCR reaction. The mixture can further include a reverse primer. For example, the reverse primer can be a primer comprising or consisting of SEQ ID NO:30.

A mixture of primers comprising SEQ ID NOS:83 and 84 is provided. This is a forward primer mixture for the protease 181C mutation-specific PCR reaction. The mixture can further include a reverse primer. For example, the reverse primer can be a primer comprising or consisting of SEQ ID NO:85.

A mixture of primers comprising one or more primers selected from the group consisting of SEQ ID NOS:38, 39, 74, 75, and 101 is provided. This is a forward primer mixture for the 215T mutation-specific PCR reaction. The mixture can further include a reverse primer. For example, the reverse primer can be a primer comprising or consisting of SEQ ID NO:45.

A mixture of primers comprising SEQ ID NO:40 and a reverse primer is provided. This is a primer mixture for the 215Y mutation-specific PCR reaction. The reverse primer can be, for example, a primer comprising or consisting of SEQ ID NO:45.

A mixture of primers comprising SEQ ID NO:41 and a reverse primer is provided. This is a primer mixture for the 215F mutation-specific PCR reaction. The reverse primer can be, for example, a primer comprising or consisting of SEQ ID NO:45.

A mixture of primers comprising SEQ ID NO:42 and a reverse primer is provided. This is a primer mixture for the 215S mutation-specific PCR reaction. The reverse primer can, for example, be a primer comprising or consisting of SEQ ID NO:45.

A mixture of primers comprising SEQ ID NO:43 and a reverse primer is provided. This is a primer mixture for the 215C mutation-specific PCR reaction. The reverse primer can, for example, be a primer comprising or consisting of SEQ ID NO:45.

A mixture of primers comprising SEQ ID NO:44 and a reverse primer is provided. This is a primer mixture for the 215D mutation-specific PCR reaction. The reverse primer can, for example, be a primer comprising or consisting of SEQ ID NO:45.

A mixture of primers comprising SEQ ID NOS:48 and 49 is provided. This is a forward primer mixture for the protease 30N mutation-specific PCR reaction. The mixture can further include a reverse primer. For example, the reverse primer can be a primer comprising or consisting of SEQ ID NO:50.

A mixture of primers comprising one or more primers selected from the group consisting of SEQ ID NOS:53, 54, 55, 78, 79 and 80 is provided. This is a forward primer mixture for the protease 90M mutation-specific PCR reaction. The mixture can further include a reverse primer. For example, the reverse primer can be a primer comprising or consisting of SEQ ID NOS:56 and 81.

A mixture of primers comprising SEQ ID NO: 133, and a reverse primer is provided. This mixture includes a forward primer for the HIV-1 integrase 138K mutation-specific PCR reaction. The reverse primer can, for example, be a primer comprising or consisting of SEQ ID NO:130.

A mixture of primers comprising SEQ ID NO: 134, and a reverse primer is provided. This mixture includes a forward primer for the HIV-1 integrase 140S mutation-specific PCR reaction. The reverse primer can, for example, be a primer comprising or consisting of SEQ ID NO:130.

A mixture of primers comprising SEQ ID NO: 137, and a forward primer is provided. This mixture includes a reverse primer for the HIV-1 integrase 155H mutation-specific PCR reaction. The forward primer can, for example, be a primer comprising or consisting of SEQ ID NO:126.

A mixture of primers comprising SEQ ID NO: 138, and a forward primer is provided. This mixture includes a reverse primer for the HIV-1 integrase 148R mutation-specific PCR reaction. The forward primer can, for example, be a primer comprising or consisting of SEQ ID NO:126.

A mixture of primers comprising SEQ ID NO: 139, and a forward primer is provided. This mixture includes a reverse primer for the HIV-1 integrase 148H mutation-specific PCR reaction. The forward primer can, for example, be a primer comprising or consisting of SEQ ID NO:126.

Also provided are mixtures of primers for mutation-specific PCR reaction for reverse transcriptase and protease. These mixtures can comprise a forward and reverse primer for a reverse transcriptase mutation and a forward and reverse primer for a protease mutation. The forward primers in the mixture can include any forward primer for the specific RT mutation to be detected and any forward primer for the protease mutation to be detected. These mixtures can be used to simultaneously detect both an RT mutation and a protease mutation. An example of such a mixture of primers comprises or consists of SEQ ID NOS: 113, 117, 118, and 122. This is a forward primer mixture for the reverse transcriptase 65R and the 90M protease mutations. The mixture can further include reverse primers. For example, the reverse primers can comprise or consist of SEQ ID NOS: 114, 119, and 81.

The mixtures (and methods) disclosed herein can utilize forward or reverse primers for other than those exemplified. The exemplified mutation non-specific forward or reverse primers were found to work well. However, the requirements of the mutation non-specific forward or reverse primer in the present method are typical of mutation non-specific forward or reverse primers designed and used routinely, and other mutation non-specific forward or reverse primers can be routinely made and used. It is expected that the mutation non-specific forward or reverse primer will be within about 40 to 250 bases from the mutation specific forward or reverse primer. It is also expected that the mutation non-specific forward or reverse primer will be positioned in a stable location lacking a degree of variability that would impede binding. The mutation non-specific forward or reverse primer is most likely to be located in the RT gene, the protease gene, or the integrase gene, but the exact location is routinely variable based on the usual criteria for mutation non-specific forward or reverse primer positioning.

Amplification mixtures are provided that include a probe for use in a real time PCR reaction. The mixtures can thus include a forward primer, a reverse primer and a probe. For example, an amplification mixture is provided comprising a forward primer or a mixture of forward primers that amplifies the 103N, 65R, and 70R mutations and for 69T, wherein the mixture further comprises an oligonucleotide having the nucleotides as set forth in SEQ ID NO:9, 115, 120, 121, or combinations thereof. This is an example of a probe that can be used in any of these mutation-specific PCR reactions. This probe can also be used in the total copy PCR reaction.

An amplification mixture is provided comprising a forward primer or a mixture of forward primers that amplifies the 41L mutations, wherein the mixture further comprises an oligonucleotide having the nucleotides as set forth in SEQ ID NO:67. This is an example of a probe that can be used in mutation-specific PCR reactions for this mutation.

An amplification mixture is provided comprising a forward primer or a mixture of forward primers that amplifies the 65R, and 67N mutations, and for 69T, wherein the mixture further comprises an oligonucleotide having the nucleotides as set forth in SEQ ID NO:68, 115, 116, 120, 121, or combinations thereof. This is an example of a probe that can be used in any of these mutation-specific PCR reactions.

An amplification mixture is provided comprising a forward primer or a mixture of forward primers that amplifies the 70R mutation, wherein the mixture further comprises an oligonucleotide having the nucleotides as set forth in SEQ ID NOS:9 or 67. This is an example of a probe that can be used in mutation-specific PCR reactions for this mutation.

An amplification mixture is provided comprising a forward primer or mixture of forward primers that amplifies the 181C and 184V mutations, wherein the mixture further comprises an oligonucleotide having the nucleotides as set forth in SEQ ID NO:32. This is an example of a probe that can be used in either of these mutation-specific PCR reactions.

An amplification mixture is provided comprising a forward primer or mixture of forward primers that amplifies the 215 mutations, wherein the mixture further comprises an oligonucleotide having the nucleotides as set forth in SEQ ID NOS:47, 76, or 77. These are examples of probes that can be used in any of these mutation-specific PCR reactions.

An amplification mixture is provided comprising a forward primer or mixture of forward primers that amplifies the protease 30N mutation, wherein the mixture further comprises an oligonucleotide having the nucleotides as set forth in SEQ ID NO:52. This is an example of a probe that can be used in mutation-specific PCR reactions for this mutation.

An amplification mixture is provided comprising a forward primer or mixture of forward primers that amplifies the protease 90M mutation, wherein the mixture further comprises an oligonucleotide having the nucleotides as set forth in SEQ ID NOS:58 or 82. This is an example of a probe that can be used in mutation-specific PCR reactions for this mutation.

An amplification mixture is provided comprising a forward primer or mixture of forward primers that amplifies the 103N mutation, wherein the mixture further comprises an oligonucleotide having the nucleotides as set forth in SEQ ID NO: 9. This is an example of a probe that can be used in mutation-specific PCR reactions for this mutation.

An amplification mixture is provided comprising a forward primer or mixture of forward primers that amplifies the 181C mutation, wherein the mixture further comprises an oligonucleotide having the nucleotides as set forth in SEQ ID NOS:86 or 87. These are examples of probes that can be used in mutation-specific PCR reactions for this mutation.

An amplification mixture is provided comprising a forward primer or mixture of forward primers that amplifies the 184V mutation, wherein the mixture further comprises an oligonucleotide having the nucleotides as set forth in SEQ ID NOS:86, or 87. These are examples of probes that can be used in mutation-specific PCR reactions for this mutation.

An amplification mixture is provided comprising a forward primer or mixture of forward primers that amplifies the integrase 138K mutation, wherein the mixture further comprises an oligonucleotide having the nucleotides as set forth in SEQ ID NO: 131 or 132. The probes of SEQ ID NO: 131 and 132 are optionally used in combination, optionally at a concentration percentage of 20% and 80% respectively. These are examples of probes that can be used in mutation-specific PCR reactions for this mutation.

An amplification mixture is provided comprising a forward primer or mixture of forward primers that amplifies the integrase 140S mutation, wherein the mixture further comprises an oligonucleotide having the nucleotides as set forth in SEQ ID NO: 131 or 132. The probes of SEQ ID NO: 131 and 132 are optionally used in combination, optionally at a concentration percentage of 20% and 80% respectively. These are examples of probes that can be used in mutation-specific PCR reactions for this mutation.

An amplification mixture is provided comprising a forward primer or mixture of forward primers that amplifies the integrase 155H mutation, wherein the mixture further comprises an oligonucleotide having the nucleotides as set forth in SEQ ID NOS:140 or 141. The probes of SEQ ID NO: 140 and 141 are optionally used in combination, optionally at a concentration percentage of 80% and 20% respectively. These are examples of probes that can be used in mutation-specific PCR reactions for this mutation.

The probe can incorporate a detectable moiety. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to a molecular probe. Common fluorescent moieties include: fluorescein, cyanine dyes, coumarins, phycoerythrin, phycobiliproteins, dansyl chloride, Texas Red, and lanthanide complexes.

The size of the primers or probes for interaction with the nucleic acids can be any size that supports the desired enzymatic manipulation of the primer, such as DNA amplification or the simple hybridization of the probe or primer. A typical primer or probe would be at least, less than or equal to 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long. Primers or probes of any length between the specified numbers are specifically contemplated.

The primers for the reverse transcriptase gene, protease gene, or integrase gene typically will be used to produce an amplified DNA product that contains a region of the reverse transcriptase gene, protease gene, or integrase gene containing the relevant site(s) of the mutation(s) of interest. In general, typically the size of the product will be such that the size can be accurately determined to within 3, or 2 or 1 nucleotides. This product can be at least, less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In the mixtures and methods described herein, the specific probes described are merely examples. Applying routine skill to the teaching herein, the person in this field can envision and make additional probes that will function in the PCR compositions and methods described.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995, incorporated herein by reference).

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6, incorporated herein by reference) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods, incorporated herein by reference), and Narang et al., Methods Enzymol., 65:610-620 (1980), incorporated herein by reference, (phosphotriester method). Protein nucleic acid molecules can be made using known methods such as those described by Nielsen et al., Bioconjug. Chem. 5:3-7 (1994), incorporated herein by reference.

Also disclosed herein are kits that are drawn to reagents that can be used in practicing the methods disclosed herein. The kits can include any reagent or combination of reagents discussed herein or that would be understood to be required or beneficial in the practice of the disclosed methods. For example, the kits could include primers to perform the amplification reactions discussed in certain embodiments of the methods, as well as the buffers and enzymes required to use the primers as intended. Specific guidance as to the components of the kits is provided herein, including buffers, primers and probes. For example, disclosed is a kit for detecting a mutation in the reverse transcriptase gene or protease gene of HIV, comprising one or more of the oligonucleotides set forth in SEQ ID Nos:1-92, 114-122, or 124-141, or any portion thereof.

For further general information, an example of coding sequences of an HIV-1 protease and an HIV-1 reverse transcriptase are provided below. Also provided are accession numbers for these and other HIV-1 protease and an HIV-1 reverse transcriptase coding sequences. Accession numbers for amino acid sequences of the HIV-1 reverse transcriptase and the HIV-1 protease are also provided. This information, along with sequence information on many more examples of HIV-1 protease and reverse transcriptase proteins and coding sequences, are in the art. As such, they constitute a part of the disclosure of the present application.

```
HIV-1 Subtype B Genome
Accession Number: NC_001802, K03455
HIV-1 Protease
Exemplary Sequence
                                                          (SEQ ID NO: 90)
  1 cctcaggtca ctctttggca acgacccctc gtcacaataa agatagggggg gcaactaaag 61 gaagctctat tagatacagg agcagatgat acagtattag aagaaatgag tttgccagga 121 agatggaaac caaaaatgat aggggaatt ggaggtttta tcaaagtaag acagtatgat
```

-continued

```
181 cagatactca tagaaatctg tggacataaa gctataggta cagtattagt aggacctaca 241 cctgtcaaca taattggaag aaatctgttg actcagattg gttgcacttt aaatttt
```

Genome Location: 1799 . . . 2095
Additional Similar Nucleotide Examples: Accession Numbers: U31398,
AJ279618, AJ279682, AJ279683, AJ279684
Protein: Accession Number: NP_705926

HIV-1 Reverse Transcriptase
Exemplary Sequence (SEQ ID NO: 91)
```
   1 cccattagcc ctattgagac tgtaccagta aaattaaagc caggaatgga tggcccaaaa 61 gttaaacaat ggccattgac agaagaaaaa ataaaagcat tagtagaaat ttgtacagag 121 atggaaaagg aagggaaaat ttcaaaaatt gggcctgaaa atccatacaa tactccagta 181 tttgccataa agaaaaaaga cagtactaaa tggagaaaat tagtagattt cagagaactt 241 aataagagaa ctcaagactt ctgggaagtt caattaggaa taccacatcc cgcagggtta 301 aaaaagaaaa aatcagtaac agtactggat gtgggtgatg catattttc agttcccttag 361 gatgaagact tcaggaagta tactgcattt accataccta gtataaacaa tgagacacca 421 gggattagat atcagtacaa tgtgcttcca gggatggaa aaggatcacc agcaatattc 481 caaagtagca tgacaaaaat cttagagcct tttagaaaac aaaatccaga catagttatc 541 tatcaataca tggatgattt gtatgtagga tctgacttag aaatagggca gcatagaaca 601 aaaatagagg agctgagaca acatctgttg aggtggggac ttaccacacc agacaaaaaa 661 catcagaaag aacctccatt cctttggatg ggttatgaac tccatcctga taaatggaca 721 gtacagccta tagtgctgcc agaaaaagac agctggactg tcaatgacat acagaagtta 781 gtggggaaat tgaattgggc aagtcagatt tacccaggga ttaaagtaag gcaattatgt 841 aaactcctta gaggaaccaa agcactaaca gaagtaatac cactaacaga agaagcagag 901 ctagaactgg cagaaaacag agagattcta aaagaaccag tacatggagt gtattatgac 961 ccatcaaaag acttaatagc agaaatacag aagcaggggc aaggccaatg gacatatcaa 1021 atttatcaag agccatttaa aaatctgaaa acaggaaaat atgcaagaat gaggggtgcc 1081 cacactaatg atgtaaaaca attaacagag gcagtgcaaa aaataaccac agaaagcata 1141 gtaatatggg gaaagactcc taaatttaaa ctgcccatac aaaaggaaac atgggaaaca 1201 tggtggacag agtattggca agccacctgg attcctgagt gggagtttgt taatacccct 1261 cccttagtga aattatggta ccagttagag aaagaaccca tagtaggagc agaaaccttc 1321 tatgtagatg gggcagctaa cagggagact aaattaggaa aagcaggata tgttactaat 1381 agaggaagac aaaaagttgt caccctaact gacacaacaa atcagaagac tgagttacaa 1441 gcaatttatc tagctttgca ggattcggga ttagaagtaa acatagtaac agactcacaa 1501 tatgcattag gaatcattca agcacaacca gatcaaagtg aatcagagtt agtcaatcaa 1561 ataatagagc agttaataaa aaaggaaaag gtctatctgg catgggtacc agcacacaaa 1621 ggaattggag gaaatgaaca agtagataaa ttagtcagtg ctggaatcag gaaagtacta
```

Genome Location: 2096 . . . 3775
Additional Similar Nucleotide Examples: Accession Numbers: U28646,
U28647, U28648, U28649, U53870, U53871
Protein: Accession Number: NP_705927

HIV-1 Subtype C Genome
Accession Number: AY162225, AY158533, DQ011180, DQ011173, AY049710
HIV-1 Protease
Exemplary Sequence (SEQ ID NO: 92)

```
  1 cctcaaatca ctctttggca gcgacccctt gtcacaataa agtaggggg tcagataaag 61 gaggctctct tagatacagg agcagatgat acagtattag aagacataaa tttgccagga 121 aaatggaaac caaaaatgat aggaggaatt ggaggtttta tcaaagtaag acagtatgat 181 caaatactta tagaaatttg tggaaaaaag gctataggta cagtattagt gggacccaca 241 cctgtcaaca taattggaag aaatatgttg actcagcttg gatgcacact aaatttt
```

Genome Location: 2215 . . . 2511
Additional Similar Nucleotide Examples: Accession Numbers: AY510039,
AY510043, AY589869.
Protein: Accession Number: AAR92431

HIV-1 Integrase
Exemplary Sequence (SEQ ID NO: 123)

```
  1 fldgidkaqe ehekyhsnwr amasdfnlpp vvakeivasc dkcqlkgeam hgqvdcspgi 61 wqldcthleg kvilvavhva sgyieaevip aetgqetayf llklagrwpv ktihtdngsn 121 ftsatvkaac wwagikqefg ipynpqsqgv vesmnkelkk iigqvrdqae hlktavqmav 181 fihnfkrkgg iggysageri vdiiatdiqt kelqkqitki qnfrvyyrds rdplwkgpak 241 llwkgegavv iqdnseikvv prrkvkiird ygkqmagddc vasrqded
```

Protein Accession Number: AAC83493

HIV-1 Reverse Transcriptase
Exemplary Sequence (SEQ ID NO: 93)

```
  1 CCAATTAGTC CYATTGAAAC TGTACCAGTA AAATTAAAGC CAGGGATGGA TGGCCCAAAG

61 GTCAAACAAT GGCCATTGAC AGAAGAAAAA ATAAAAGCAT TAATAGCAAT TTGTGAAGAG

121 ATGGAGAAGG AAGGAAAAAT TACAAAAATT GGGCCTGAAA ATCCATATAA CACCCCAGTA

181 TTTGCCATAA AAAGAAGGA CAGTACTAAG TGGAGAAAAT TAGTAGATTT CAGGGAACTC

241 AATAAAAGAA CTCAAGACTT TTGGGAAGTT CAATTAGGGA TACCACACCC AGCAGGGTTA

301 AAGAAAAAGA AATCAGTAAC AGTACTGGAT GTGGGGGATG CATATTTTTC AGTTCCTTTA

361 GATAAAGACT TCAGAAAATA TACTGCATTC ACCATACCTA GTATAAACAA TGAGACACCA

421 GGGATTAGAT ATCAATATAA TGTGCTTCCA CAGGGATGGA AAGGATCACC ATCAATATTC

481 CAAAGTAGTA TGACAAAAAT CTTAGAGCCC TTTAGGGCAC AAAATCCAGA ATTGGTTATT

541 TATCAATATA TGGATGACTT GTATGTAGGA TCCGACTTAG AAATAGGGCA GCATAGAGCA

601 AAAATAGAGG AGTTAAGAAA ACATCTATTG AGGTGGGGAT TTACCACACC AGACAAGAAA

661 CATCAGAAAG AACCTCCATT TCTTTGGATG GGGTATGAAC TCCATCCTGA CAAATGGACA

721 GTACAGCCTA TAAAGCTGCC AGAAAAGGAT AGCTGGACTG TTAATGATAT ACAGAAGTTA

781 GTGGGAAAAC TAAACTGGGC AAGTCAGATT TACAAAGGGA TTAAAGTAAG GCAGCTGTGT

841 AGACTCCTTA GGGGAGCCAA AGCACTAACA GACATAGTAC CACTGACTGA AGAAGCAGAA

901 TTAGAATTGG CAGAGAACAG GGAAATTCTA AAAGAACCAG TACATGGAGT ATATTATGAC

961 TCA
```

Genome Location: 2512 . . . 3477
Additional Similar Nucleotide Examples: Accession Numbers: AY510056,
AY510047, AY589935, AF468458
Protein: Accession Number: AAR92448

```
HIV-1 Subtype D Genome
Accession Number: AY322189, AY773341, AJ320484
HIV-1 Protease
Exemplary Sequence
                                                              (SEQ ID NO: 94)
  1 CCTCAAATCA CTCTTTGGCA ACGACCCCTT GTCACAGTAA RGATAGGGGG ACAACTAAAG

61 GAAGCTCTAT TAGATACAGG AGCAGATGAT ACAGTATTGG AAGAAATGAA TTTGCCAGGA

121 AAATGGAAAC CAAAAATGAT AGGGGGAATT GGAGGCTTTA TCAAAGTAAG ACAGTATGAT

181 CAAATACTTG TAGAAATCTG TGGATATAAG GCTATAGGTA CAGTGTTAGT AGGACCTACA

241 CCTGTCAACA TAATTGGAAG AAATTTGTTG ACTCAGATTG GTTGCACTTT AAATTTT

Genome Location: 1719 . . . 2015
Additional Similar Nucleotide Examples: Accession Numbers: AJ296664
Protein: Accession Number: CAC03695

HIV-1 Reverse Transcriptase
Exemplary Sequence
                                                              (SEQ ID NO: 95)
  1 CCAATTAGTC CTATTGAAAC TGTACCAGTA AAATTAAAGC CAGGGATGGA TGGCCCAAAA

61 GTTAAACAAT GGCCGTTAAC AGAAGAAAAA ATAAAAGCAC TAACAGAAAT TTGTACAGAA

121 ATGGAAAAGG AAGGAAAAAT TTCAAGAATT GGGCCTGAAA ATCCATACAA TACTCCAATA

181 TTTGCCATAA AGAAAAAAGA CAGTACTAAR TGGAGAAAAT TAGTAGATTT TAGAGAACTT

241 AATAAGAGAA CTCAAGACTT CTGGGAAGTT CAACTAGGAA TACCACATCC TGCAGGGCTA

301 AAAAGAAAA AATCAGTAAC AGTACTGGAT GTGGGWGATG CATATTTTTC AGTTCCCTTA

361 TATGAAGACT TTAGAAAATA TACTGCATTC ACCATACCYA GTATAAATAA TGAGACACCA

421 GGAATTAGAT ATCAGTACAA TGTGCTTCCA CAAGGATGGA AAGGATCACC GGCAATATTT

481 CAAAGTAGCA TGACAAAAAT CTTAGAACCT TTTAGAAAAC AAAATCCAGA AATGGTGATC

541 TATCAATACA TGGATGATTT GTATGTAGGA TCTGACTTAG AAATAGGGCA GCATAGAATA

601 AAAATAGAGG AATTAAGGGA ACACTTATTG AAGTGGGGAT TTACCACACC AGACAAAAAG

661 CATCAGAAAG AACCCCCATT TCTTTGGATG GGTTATGAAC TCCATCCGGA TAAATGGACA

721 GTACAGCCTA TAAAACTGCC AGAAAAAGAA AGCTGGACTG TCAATGATAT ACAGAAGTTA

781 GTGGGAAAAT TAAATTGGGC AAGTCAGATT TATCCAGGAA TTAAAGTAAG ACAATTATGC

841 AAATGCATTA GGGGAGCCAA AGCACTGACA GAAGTAGTAC CACTGACAGAAGAAGCAGAA

901 TTAGAACTGG CAGAAAACAG AGAAATTCTA AAAGAACCAG TACATGGAGT GTATTATGAT

961 CCA

Genome Location: 2016 . . . 2978
Additional Similar Nucleotide Examples: Accession Numbers: AF388101
Protein: Accession Number: AAL84043
```

Methods

Provided are methods for the specific detection of several mutations in HIV individually or simultaneously. Mutations in the reverse transcriptase, protease, or integrase of HIV can be detected using the methods described herein. The methods are highly sensitive and specific. Specific examples of such methods are described. However, it is recognized that modifications of the exemplified methods using the alternative methods disclosed can be routinely accomplished. Any source of viral RNA can be used in the present invention. Such RNA is not limited to that obtained from plasma or serum, but can also be intracellular RNA that has not been packaged. Detection can be achieved so long as any of the disclosed primers are paired with any of the mutation specific forward or reverse primers for a given mutation. The following methods describe specific sets of primers that achieve especially sensitive levels of detection.

A method for detecting the 103N mutation in the reverse transcriptase of HIV-1 is provided, comprising (a) reverse transcribing RNA extracted from HIV-1 with a primer selected from the group consisting of SEQ ID NO:3 and SEQ ID NO:6 to produce a reverse transcription reaction product; (b) contacting the reverse transcription product of step (a) with a primer set selected from the group consisting of SEQ ID NOS:1, 2, 4 and 5 to produce a DNA product; and (c) contacting the DNA product of step (b) with a reverse primer and a primer set selected from the group consisting of SEQ ID NOS:22, 23, 24 and 25 and SEQ ID NOS:59, 60 and 61 to amplify HIV-1 DNA containing the 103N mutation. The reverse primer is routinely selected based on the well-known criteria for such selections, which are described herein and elsewhere. For example, the reverse primer can be a primer comprising or consisting of SEQ ID NO:26. In the methods disclosed, the presence of an amplification signal within a certain number of cycles after signal detection in the total copy PCR reaction indicates the presence of the respective mutation. This method, for use with an RNA template, detects the 103N mutation in either or both of Subtype B and Subtype C. SEQ ID NOS: 4 and 5 are forward RT-PCR (for RNA) and primary PCR (for DNA) primers for Subtype C. SEQ ID NO:4 includes protease sequences while SEQ ID NO:5 is for reverse transcriptase only. SEQ ID NOS: 1 and 2 are forward RT-PCR (for RNA) and primary PCR (for DNA) primers for Subtype B. SEQ ID NO:1 includes protease sequences while SEQ ID NO:2 is for reverse transcriptase only.

Details of the RT-PCR (steps (a) and (b)) and secondary PCR (step (c)) for the detection methods starting with RNA are described in the Examples. In step (c) of these methods, a set of primers is used, including at least a primer pair comprising a reverse primer and one of the disclosed forward primers for the respective mutation. In step (b) of the methods starting with RNA, the choice of amplifying both the reverse transcriptase and the protease are provided by an exemplary primary PCR forward primer that includes protease and an exemplary primary forward primer for reverse transcriptase only.

Each forward primer disclosed for the RT-PCR reaction or the primary PCR reaction in the methods disclosed works independently. If a protease analysis is to be done, then the F1 primers must be used for the RT-PCR or primary PCR steps. Reverse transcriptase analyses can be performed from the F2+reverse primer products alone (the F2 primers are slightly more sensitive than the F1 primers, thus can provide the user with a more sensitive test). In step (b) of the methods starting with RNA, there is reverse primer remaining in the reaction product from step (a).

The RT step of the present methods can utilize RT primers other than those described. The only requirement is that the primers generate a template in the relevant region of the reverse transcriptase gene or in the protease gene or both.

A further method for detecting the 103N mutation in the reverse transcriptase of HIV-1 is provided, comprising (a) contacting DNA with a reverse primer and a primer selected from the group consisting of SEQ ID NOS:1, 2, 4 and 5 to amplify the DNA; and (b) contacting the amplified DNA of step (a) with a reverse primer and a primer set selected from the group consisting of SEQ ID NOS:22, 23, 24 and 25 and SEQ ID NOS:59, 60 and 61 to amplify HIV-1 DNA containing the 103N mutation. The reverse primer is routinely selected based on the well-known criteria for such selections, which are described herein and elsewhere. For example, the reverse primer can be a primer comprising or consisting of SEQ ID NO:26. This method, for use with a DNA template, detects the 103N mutation in either or both of Subtype B and Subtype C.

Details of the primary PCR and secondary PCR steps for the detection methods starting with DNA are described in the Examples. In step (b) of these methods, a set of primers is used, including at least a primer pair comprising a reverse primer and one of the disclosed forward primers for the respective mutation. In step (a) of the methods starting with DNA, the choice of amplifying the reverse transcriptase, the protease, and the integrase are provided by an exemplary primary PCR forward primer that includes protease and an exemplary forward primer for reverse transcriptase, and a forward primer for integrase only. Each forward primer disclosed for the primary PCR reaction in the method beginning with DNA works independently. Thus, the RT-only primer and the protease-included primer can be used independently with a reverse primer. If a protease analysis is to be done, then the F1 primers must be used for the RT-PCR or primary PCR steps. Reverse transcriptase analyses can be performed from the F2+reverse primer products alone (the F2 primers are slightly more sensitive than the F1 primers, thus can provide the user with a more sensitive test).

Amplification methods are provided that include a probe for use in a real time PCR reaction. The methods can thus include the use of a forward primer, a reverse primer and a probe. For example, an amplification method is provided comprising a forward primer or a mixture of forward primers that amplifies the protease 90M, and the reverse transcriptase 103N, 65R, and 70R mutations, wherein the method further comprises using an oligonucleotide having the nucleotides as set forth in SEQ ID NO:9. This is an example of a probe that can be used in any of these mutation-specific PCR reactions. This probe can also be used in the total copy PCR reaction.

A method for detecting a Subtype B 184V mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:33, 34 and 35 and a reverse primer to amplify HIV-1 DNA containing a Subtype B 184V mutation. The reverse primer is routinely selected based on the well-known criteria for such selections, which are described herein and elsewhere. For example, the reverse primer can be a primer comprising or consisting of SEQ ID NO:36.

A method for detecting a Subtype B 184V mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:33, 34 and 35 and a reverse primer to amplify HIV-1 DNA containing a Subtype B 184V mutation. The reverse primer is routinely selected based on the well-known criteria for such selections, which are described herein and elsewhere. For example, the reverse primer can be a primer comprising or consisting of SEQ ID NO:36.

An amplification method is provided comprising a forward primer or mixture of forward primers that amplifies a Subtype B 181C and Subtype B 184V mutations, wherein the method further comprises using an oligonucleotide having the nucleotides as set forth in SEQ ID NO:32. This is an example of a probe that can be used in either of these mutation-specific PCR reactions.

A method for detecting a Subtype B 41L mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:62, 63, 64 and 65 and a reverse primer to amplify HIV-1 DNA containing a Subtype B 41L mutation. The reverse primer is routinely selected based on the well-known criteria for such selections, which are described herein and elsewhere. For example, the reverse primer can be a primer comprising or consisting of SEQ ID NO:66.

A method for detecting a Subtype B 41L mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:63, 96, 97, 64, and 65 and a reverse primer to amplify HIV-1 DNA containing a Subtype B 41L mutation. The reverse primer is routinely selected based on the well-known criteria for such selections, which are described herein and elsewhere. For example, the reverse primer can be a primer comprising or consisting of SEQ ID NO:66.

A method for detecting a Subtype B 41L mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 62, 63, 64 and 65 and a reverse primer to amplify HIV-1 DNA containing a Subtype B 41L mutation. The reverse primer is routinely selected based on the well-known criteria for such selections, which are described herein and elsewhere. For example, the reverse primer can be a primer comprising or consisting of SEQ ID NO:66.

A method for detecting a Subtype B 41L mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 63, 96, 97, 64, and 65 and a reverse primer to amplify HIV-1 DNA containing a Subtype B 41L mutation. The reverse primer is routinely selected based on the well-known criteria for such selections, which are described herein and elsewhere. For example, the reverse primer can be a primer comprising or consisting of SEQ ID NO:66.

An amplification method is provided comprising a forward primer or mixture of forward primers that amplifies a Subtype B 41L mutation, wherein the method further comprises using an oligonucleotide having the nucleotides as set forth in SEQ ID NO:67. This is an example of a probe that can be used in mutation-specific PCR reactions for this mutation.

A method for detecting a Subtype B 65R mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer comprising SEQ ID NO:10 and a reverse primer to amplify HIV-1 DNA containing a Subtype B 65R mutation. The reverse primer is routinely selected based on the well-known criteria for such selections, which are described herein and elsewhere. For example, the reverse primer can be a primer comprising or consisting of SEQ ID NO:11.

A method for detecting a Subtype B 65R mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer comprising SEQ ID NO:98 and a reverse primer to amplify HIV-1 DNA containing a Subtype B 65R mutation. The reverse primer is routinely selected based on the well-known criteria for such selections, which are described herein and elsewhere. For example, the reverse primer can be a primer comprising or consisting of SEQ ID NO:11.

A method for detecting a Subtype B 65R mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer comprising SEQ ID NO:10 and a reverse primer to amplify HIV-1 DNA containing a Subtype B 65R mutation. The reverse primer is routinely selected based on the well-known criteria for such selections, which are described herein and elsewhere. For example, the reverse primer can be a primer comprising or consisting of SEQ ID NO:11.

A method for detecting a Subtype B 65R mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer comprising SEQ ID NO:98 and a reverse primer to amplify HIV-1 DNA containing a Subtype B 65R mutation. The reverse primer is routinely selected based on the well-known criteria for such selections, which are described herein and elsewhere. For example, the reverse primer can be a primer comprising or consisting of SEQ ID NO:11.

An amplification method is provided comprising a forward primer or mixture of forward primers that amplifies a Subtype B 65R mutation, wherein the method further comprises using an oligonucleotide having the nucleotides as set forth in SEQ ID NOS:9, 68, or 99. These are examples of probes that can be used in mutation-specific PCR reactions for this mutation.

A method for detecting a Subtype AE 65R mutation in the reverse transcriptase of HIV-1 is provided, comprising (a) contacting DNA with a reverse primer and a primer selected from the group consisting of SEQ ID NOS:1 and 2 to produce a common DNA amplification product; and (b) contacting the DNA of step (a) with a primer comprising SEQ ID NO:113 and a reverse primer to amplify HIV-1 DNA containing a Subtype AE 65R mutation. The reverse primer is routinely selected based on the well-known criteria for such selections, which are described herein and elsewhere. For example, the reverse primer can be a primer comprising or consisting of SEQ ID NO:114.

A method for detecting a Subtype C 65R mutation in the reverse transcriptase of HIV-1 is provided, comprising (a) contacting DNA with a reverse primer and a primer selected from the group consisting of SEQ ID NOS:1 and 2 produce a common DNA amplification product; and (b) contacting the DNA of step (a) with a primer comprising SEQ ID NOs:117 and 118, and a reverse primer to amplify HIV-1 DNA containing a Subtype C 65R mutation. The reverse primer is routinely selected based on the well-known criteria for such selections, which are described herein and elsewhere. For example, the reverse primer can be a primer comprising or consisting of SEQ ID NO:119.

A method for detecting a Subtype C 65R mutation in the reverse transcriptase of HIV-1 is provided, comprising (a) contacting DNA with a reverse primer and a primer selected from the group consisting of SEQ ID NOS: 1 and 2 to produce a common DNA amplification product; and (b) contacting the DNA of step (a) with a primer comprising SEQ ID NOs:117, 118, and 122, and a reverse primer to amplify HIV-1 DNA containing a Subtype C 65R mutation. The reverse primer is routinely selected based on the well-known criteria for such selections, which are described herein and elsewhere. For example, the reverse primer can be a primer comprising or consisting of SEQ ID NO:119.

An amplification method is provided comprising a forward primer or mixture of forward primers that amplifies a Subtype AE 65R mutation, wherein the method further comprises using an oligonucleotide having the nucleotides as set forth in SEQ ID NOS: 115, 116, or combinations thereof. These are examples of probes that can be used in mutation-specific PCR reactions for this mutation.

An amplification method is provided comprising a forward primer or mixture of forward primers that amplifies a Subtype C 65R mutation, wherein the method further comprises using an oligonucleotide having the nucleotides as set forth in SEQ ID NOS: 120, 121, or combinations thereof. These are examples of probes that can be used in mutation-specific PCR reactions for this mutation.

A method for detecting a Subtype B 67N mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:69 and 70 and a reverse primer to amplify HIV-1 DNA containing a Subtype B 67N mutation. The reverse primer is routinely selected based on the well-known criteria for such selections, which are described herein and elsewhere. For example, the reverse primer can be a primer comprising or consisting of SEQ ID NO:8.

A method for detecting a Subtype B 67N mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:69 and 70 and a reverse primer to amplify HIV-1 DNA containing a Subtype B 67N mutation. The reverse primer is routinely selected based on the well-known criteria for such selections, which are described herein and elsewhere. For example, the reverse primer can be a primer comprising or consisting of SEQ ID NO:8.

An amplification method is provided comprising a forward primer or mixture of forward primers that amplifies a Subtype B 67N mutation, wherein the method further comprises using an oligonucleotide having the nucleotides as set forth in SEQ ID NO:68. This is an example of a probe that can be used in mutation-specific PCR reactions for this mutation.

A method for detecting a Subtype B 69T in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:12 and 13 and a reverse primer to amplify HIV-1 DNA containing a Subtype B 69T. The reverse primer is routinely selected based on the well-known criteria for such selections, which are described herein and elsewhere. For example, the reverse primer can be a primer comprising or consisting of SEQ ID NO:14.

A method for detecting a Subtype B 69T in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:12 and 71 and a reverse primer to amplify HIV-1 DNA containing a Subtype B 69T. The reverse primer is routinely selected based on the well-known criteria for such selections, which are described herein and elsewhere. For example, the reverse primer can be a primer comprising or consisting of SEQ ID NO:8.

A method for detecting a Subtype B 69T in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:12 and 13 and a reverse primer to amplify HIV-1 DNA containing a Subtype B 69T. The reverse primer is routinely selected based on the well-known criteria for such selections, which are described herein and elsewhere. For example, the reverse primer can be a primer comprising or consisting of SEQ ID NO:14.

A method for detecting a Subtype B 69T in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:12 and 71 and a reverse primer to amplify HIV-1 DNA containing a Subtype B 69T. The reverse primer is routinely selected based on the well-known criteria for such selections, which are described herein and elsewhere. For example, the reverse primer can be a primer comprising or consisting of SEQ ID NO:8.

An amplification method is provided comprising a forward primer or mixture of forward primers that amplifies a Subtype B 69T, wherein the method further comprises using an oligonucleotide having the nucleotides as set forth in SEQ ID NOS:9 or 68. These are examples probes that can be used in mutation-specific PCR reactions for this mutation.

A method for detecting a Subtype B 70R mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:16, 17, 18 and 19 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NO:20.

A method for detecting a Subtype B 70R mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NO:2 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NOS:72 and 73.

A method for detecting a Subtype B 70R mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NO:100 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NOS:72 and 73.

A method for detecting a Subtype B 70R mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:16, 17, 18 and 19 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NO:20.

A method for detecting a Subtype B 70R mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NO:2 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NOS:72 and 73.

A method for detecting a Subtype B 70R mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NO:100 and a reverse primer to amplify HIV-1 DNA containing a Subtype B 70R mutation. The reverse primer is routinely selected based on the well-known criteria for such selections, which are described herein and elsewhere. For example, the reverse primer can be a primer comprising or consisting of SEQ ID NOS:72 and 73.

An amplification method is provided comprising a forward primer or mixture of forward primers that amplifies a Subtype B 70R mutation, wherein the method further comprises using an oligonucleotide having the nucleotides as set forth in SEQ ID NO:9 or 67. This is an example of a probe that can be used in mutation-specific PCR reactions for this mutation.

A method for detecting a Subtype B 103N mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:22, 23, 24 and 25 and a reverse primer to amplify HIV-1 DNA containing a Subtype B 103N mutation. The reverse primer is routinely selected based on the well-known criteria for such selections, which are described herein and elsewhere. For example, the reverse primer can be a primer comprising or consisting of SEQ ID NO:26.

A method for detecting a Subtype B 103N mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:22, 23, 24 and 25 and a reverse primer to amplify HIV-1 DNA containing a Subtype B 103N mutation. The reverse primer is routinely selected based on the well-known criteria for such selections, which are described herein and elsewhere. For example, the reverse primer can be a primer comprising or consisting of SEQ ID NO:26.

An amplification method is provided comprising a forward primer or mixture of forward primers that amplifies a Subtype B 103N mutation, wherein the method further comprises using an oligonucleotide having the nucleotides as set forth in SEQ ID NO:9. This is an example of a probe that can be used in mutation-specific PCR reactions for this mutation.

A method for detecting a Subtype B 181C mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:28 and 29 and a reverse primer to amplify HIV-1 DNA containing a Subtype B 181C mutation. The reverse primer is routinely selected based on the well-known criteria for such selections, which are described herein and elsewhere. For example, the reverse primer can be a primer comprising or consisting of SEQ ID NO:30.

A method for detecting a Subtype B 181C mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 28 and 29 and a reverse primer to amplify HIV-1 DNA containing a Subtype B 181C mutation. The reverse primer is routinely selected based on the well-known criteria for such selections, which are described herein and elsewhere. For example, the reverse primer can be a primer comprising or consisting of SEQ ID NO:30.

An amplification method is provided comprising a forward primer or mixture of forward primers that amplifies a Subtype B 181C mutation, wherein the method further comprises using an oligonucleotide having the nucleotides as set forth in SEQ ID NO:32. This is an example of a probe that can be used in mutation-specific PCR reactions for this mutation.

A method for detecting a Subtype B 215T mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 or SEQ ID NOS:74 and 75 or SEQ ID NOS:101 and 75 to produce a DNA product; (c) contacting the DNA product of step (b) with a reverse primer and a primer selected from the group consisting of SEQ ID NOS:38 and 39 to amplify HIV-1 DNA containing a Subtype B 215 mutation. The reverse primer is routinely selected based on the well-known criteria for such selections, which are described herein and elsewhere. For example, the reverse primer can be a primer comprising or consisting of SEQ ID NO:45.

A method for detecting a Subtype B 215 mutation in the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; (c) contacting the DNA product of step (b) with a reverse primer and a primer selected from the group consisting of SEQ ID NOS:40, 41, 42, 43 and 44 to amplify HIV-1 DNA containing a Subtype B 215 mutation. The reverse primer is routinely selected based on the well-known criteria for such selections, which are described herein and elsewhere. For example, the reverse primer can be a primer comprising or consisting of SEQ ID NO:45.

A method for detecting a Subtype B 215 mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a reverse primer and a primer selected from the group consisting of SEQ ID NOS:40, 41, 42, 43 and 44 to amplify HIV-1 DNA containing a Subtype B 215 mutation. The reverse primer is routinely selected based on the well-known criteria for such selections, which are described herein and elsewhere. For example, the reverse primer can be a primer comprising or consisting of SEQ ID NO:45.

In the present methods of detecting a mutation at position Subtype B 215, any or all of the Y, F, S, C or D mutations can be detected. Thus, to detect any mutation at this position, the forward primers can be used together in the reaction mixture. To detect a specific mutation, the forward primer for that mutation would be used alone. Specific combinations of mutations at 215 can be identified by using the desired subset of the disclosed forward primers.

An amplification method is provided comprising a forward primer or mixture of forward primers that amplifies Subtype B 215 mutations, wherein the method further comprises using an oligonucleotide having the nucleotides as set forth in SEQ ID NOS:47, 76, or 77. This is an example of a probe that can be used in mutation-specific PCR reactions for this mutation.

A method for detecting the 30N mutation in the protease of HIV-1 Subtype 13 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:48 and 49 and a reverse primer to amplify HIV-1 DNA containing the 30N mutation. The reverse primer is routinely selected based on the well-known criteria for such selections, which are described herein and elsewhere. For example, the reverse primer can be a primer comprising or consisting of SEQ ID NO:50.

A method for detecting the 30N mutation in the protease of HIV-1 Subtype 13 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:48 and 49 and a reverse primer to amplify HIV-1 DNA containing the 30N mutation. The reverse primer is routinely selected based on the well-known criteria for such selections, which are described herein and elsewhere. For example, the reverse primer can be a primer comprising or consisting of SEQ ID NO:50.

An amplification method is provided comprising a forward primer or mixture of forward primers that amplifies the protease 30N mutation of HIV-1 Subtype B, wherein the method further comprises the use of an oligonucleotide having the nucleotides as set forth in SEQ ID NO:52. This is an example of a probe that can be used in mutation-specific PCR reactions for this mutation.

A method for detecting the 90M mutation in the protease of HIV-1 Subtype B is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:53, 54, and 55 and a reverse primer to amplify HIV-1 DNA containing the 90M mutation. The reverse primer is routinely selected based on the well-known criteria for such selections, which are described herein and elsewhere. For example, the reverse primer can be a primer comprising or consisting of SEQ ID NO:56.

A method for detecting the 90M mutation in the protease of HIV-1 Subtype B is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS: 55, 78, 79, and 80 and a reverse primer to amplify HIV-1 DNA containing the 90M mutation. The reverse primer is routinely selected based on the well-known criteria for such selections, which are described herein and elsewhere. For example, the reverse primer can be a primer comprising or consisting of SEQ ID NO:81.

A method for detecting the 90M mutation in the protease of HIV-1 Subtype B is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:53, 54, and 55 and a reverse primer to amplify HIV-1 DNA containing the 90M mutation. The reverse primer is routinely selected based on the well-known criteria for such selections, which are described herein and elsewhere. For example, the reverse primer can be a primer comprising or consisting of SEQ ID NO:56.

A method for detecting the 90M mutation in the protease of HIV-1 Subtype B is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:55, 78, 79, and 80 and a reverse primer to amplify HIV-1 DNA containing the 90M mutation. The reverse primer is routinely selected based on the well-known criteria for such selections, which are described herein and elsewhere. For example, the reverse primer can be a primer comprising or consisting of SEQ ID NO:81.

An amplification method is provided comprising a forward primer or mixture of forward primers that amplifies the protease 90M mutation, wherein the method further comprises the use of an oligonucleotide having the nucleotides as set forth in SEQ ID NOS:58 or 82. These are examples probes that can be used in mutation-specific PCR reactions for this mutation.

A method for detecting a Subtype C 103N mutation in the reverse transcriptase of HIV-1 is provided, comprising (a) reverse transcribing RNA extracted from HIV-1 with a primer comprising SEQ ID NO:6 to produce a reverse transcription reaction product; (b) contacting the reverse transcription product of step (a) with a primer selected from the group consisting of SEQ ID NOS:3 and 4 to produce a DNA product; and (c) contacting the DNA product of step (b) with a primer set comprising SEQ ID NOS:59, 60, and 61 and a reverse primer to amplify HIV-1 DNA containing a Subtype C 103N mutation. The reverse primer is routinely selected based on the well-known criteria for such selections, which are described herein and elsewhere. For example, the reverse primer can be a primer comprising or consisting of SEQ ID NO:26.

A method for detecting a Subtype C 103N mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 59, 60, and 61 and a reverse primer to amplify HIV-1 DNA containing a Subtype C 103N mutation. The reverse primer is routinely selected based on the well-known criteria for such selections, which are described herein and elsewhere. For example, the reverse primer can be a primer comprising or consisting of SEQ ID NO:26.

An amplification method is provided comprising a forward primer or mixture of forward primers that amplifies a Subtype C 103N mutation, wherein the method further comprises using an oligonucleotide having the nucleotides as set forth in SEQ ID NO:9. This is an example of a probe that can be used in mutation-specific PCR reactions for this mutation.

A method for detecting a Subtype C 181C mutation in the reverse transcriptase of HIV-1 is provided, comprising (a) reverse transcribing RNA extracted from HIV-1 with a primer comprising SEQ ID NO:6 to produce a reverse transcription reaction product; (b) contacting the reverse transcription product of step (a) with a primer selected from the group consisting of SEQ ID NOS:3 and 4 to produce a DNA product; and (c) contacting the DNA product of step (b) with a primer set comprising SEQ ID NOS:83 and 84 and a reverse primer to amplify HIV-1 DNA containing a Subtype C 181C mutation. The reverse primer is routinely selected based on the well-known criteria for such selections, which are described herein and elsewhere. For example, the reverse primer can be a primer comprising or consisting of SEQ ID NO:85.

A method for detecting a Subtype C 181C mutation in the reverse transcriptase of HIV-1 is provided, comprising (a) contacting DNA with a reverse primer and a primer selected from the group consisting of SEQ ID NOS:3 and 4 to amplify the DNA; and (b) contacting the amplified DNA of step (a) with a primer set comprising SEQ ID NOS:83 and 84 and a reverse primer to amplify HIV-1 DNA containing a Subtype C 181C mutation. The reverse primer is routinely selected based on the well-known criteria for such selections, which are described herein and elsewhere. For example, the reverse primer can be a primer comprising or consisting of SEQ ID NO:85.

An amplification method is provided comprising a forward primer or mixture of forward primers that amplifies a Subtype C 103N mutation, wherein the method further comprises using an oligonucleotide having the nucleotides as set forth in SEQ ID NOS:86 or 87. These are examples of probes that can be used in mutation-specific PCR reactions for this mutation.

A method for detecting a Subtype C 184V mutation in the reverse transcriptase of HIV-1 is provided, comprising (a) reverse transcribing RNA extracted from HIV-1 with a primer comprising SEQ ID NO:6 to produce a reverse transcription reaction product; (b) contacting the reverse transcription product of step (a) with a primer selected from the group consisting of SEQ ID NOS:3 and 4 to produce a DNA product; and (c) contacting the DNA product of step (b) with a primer set comprising SEQ ID NOS:88 and 89 and a reverse primer to amplify HIV-1 DNA containing a Subtype C 184V mutation. The reverse primer is routinely selected based on the well-known criteria for such selections, which are described herein and elsewhere. For example, the reverse primer can be a primer comprising or consisting of SEQ ID NO:85.

A method for detecting a Subtype C 184V mutation in the reverse transcriptase of HIV-1 is provided, comprising (a) reverse transcribing RNA extracted from HIV-1 with a primer comprising SEQ ID NO:6 to produce a reverse transcription reaction product; (b) contacting the reverse transcription product of step (a) with a primer selected from the group consisting of SEQ ID NOS:3 and 4 to produce a DNA product; and (c) contacting the DNA product of step (b) with a primer set comprising SEQ ID NOS:102, 103 and 104 and a reverse primer to amplify HIV-1 DNA containing a Subtype C 184V mutation. The reverse primer is routinely selected based on the well-known criteria for such selections, which are described herein and elsewhere. For example, the reverse primer can be a primer comprising or consisting of SEQ ID NO:85.

A method for detecting a Subtype C 184V mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 88 and 89 and a reverse primer to amplify HIV-1 DNA containing a Subtype C 184V mutation. The reverse primer is routinely selected based on the well-known criteria for such selections, which are described herein and elsewhere. For example, the reverse primer can be a primer comprising or consisting of SEQ ID NO:85.

A method for detecting a Subtype C 184V mutation in the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS: 102, 103 and 104 and a reverse primer to amplify HIV-1 DNA containing a Subtype C 184V mutation. The reverse primer is routinely selected based on the well-known criteria for such selections, which are described herein and elsewhere. For example, the reverse primer can be a primer comprising or consisting of SEQ ID NO:85.

An amplification method is provided comprising a forward primer or mixture of forward primers that amplifies a Subtype C 184V mutation, wherein the method further comprises using an oligonucleotide having the nucleotides as set forth in SEQ ID NOS:86 or 87. These are examples of probes that can be used in mutation-specific PCR reactions for this mutation.

A method for detecting a 138K mutation in the integrase of HIV-1 is provided, comprising (a) contacting DNA with a reverse primer and a forward primer selected from the group consisting of SEQ ID NOS:126 and 129 to produce a common DNA amplification product; and (b) contacting the DNA of step (a) with a mutation specific forward primer comprising SEQ ID NOS: 133 and a reverse primer to amplify HIV-1 DNA containing a integrase 138K mutation. The reverse primer is routinely selected based on the well-known criteria for such selections, which are described herein and elsewhere. For example, the reverse primer can be a primer comprising or consisting of SEQ ID NO:130.

An amplification method is provided comprising a forward primer or mixture of forward primers that amplifies an integrase 138K mutation, wherein the method further comprises oligonucleotides having the nucleotides as set forth in SEQ ID NOS:131, 132 or combinations thereof. The oligonucleotides of SEQ ID NO: 131 and 132 are optionally used in combination optionally at a concentration percentage of 20% and 80% respectively. These are examples of probes that can be used in mutation-specific PCR reactions for this mutation.

A method for detecting a 140S mutation in the integrase of HIV-1 is provided, comprising (a) contacting DNA with a reverse primer and forward primer selected from the group consisting of SEQ ID NOS:126 and 129 to produce a common DNA amplification product; and (b) contacting the DNA of step (a) with a mutation specific forward primer comprising SEQ ID NO: 134 and a reverse primer to amplify HIV-1 DNA containing a integrase 140S mutation. The reverse primer is routinely selected based on the well-known criteria for such selections, which are described herein and elsewhere. For example, the reverse primer can be a primer comprising or consisting of SEQ ID NO:130.

An amplification method is provided comprising a forward primer or mixture of forward primers that amplifies an integrase 140S mutation, wherein the method further comprises using oligonucleotides having the nucleotides as set forth in SEQ ID NOS:131, 132 or combinations thereof. The oligonucleotides of SEQ ID NO: 131 and 132 are optionally used in combination at a concentration percentage of 20% and 80% respectively. These are examples of probes that can be used in mutation-specific PCR reactions for this mutation.

A method for detecting a 155H mutation in the integrase of HIV-1 is provided, comprising (a) contacting DNA with a forward primer and a reverse primer selected from the group consisting of SEQ ID NOS:124 and 129 to produce a common DNA amplification product; and (b) contacting the DNA of step (a) with a mutation specific reverse primer comprising SEQ ID NO: 137 and a forward primer to amplify HIV-1 DNA containing a integrase 155H mutation. The forward primer is routinely selected based on the well-known criteria for such selections, which are described herein and elsewhere. For example, the reverse primer can be a primer comprising or consisting of SEQ ID NO:126.

An amplification method is provided comprising a forward primer or mixture of forward primers that amplifies an integrase 155H mutation, wherein the method further comprises using oligonucleotides having the nucleotides as set forth in SEQ ID NOS:140, 141 or combinations thereof. The oligonucleotides of SEQ ID NO: 140 and 141 are optionally used in combination at a concentration percentage of 80% and 20% respectively. These are examples of probes that can be used in mutation-specific PCR reactions for this mutation.

A method for detecting a 148R mutation in the integrase of HIV-1 is provided, comprising (a) contacting DNA with a forward primer and a reverse primer selected from the group consisting of SEQ ID NOS:124 and 125 to produce a common DNA amplification product; and (b) contacting the DNA of step (a) with a mutation specific reverse primer comprising SEQ ID NOS: 138 and a forward primer to amplify HIV-1 DNA containing a integrase 148R mutation. The forward primer is routinely selected based on the well-known criteria for such selections, which are described herein and elsewhere. For example, the reverse primer can be a primer comprising or consisting of SEQ ID NO:126.

An amplification method is provided comprising a forward primer or mixture of forward primers that amplifies an integrase 148R mutation, wherein the method further comprises using oligonucleotides having the nucleotides as set forth in SEQ ID NOS:140, 141 or combinations thereof. The oligonucleotides of SEQ ID NO: 140 and 141 are optionally used in combination at a concentration percentage of 80% and 20% respectively. These are examples of probes that can be used in mutation-specific PCR reactions for this mutation.

A method for detecting a 148H mutation in the integrase of HIV-1 is provided, comprising (a) contacting DNA with a forward primer and a reverse primer selected from the group consisting of SEQ ID NOS:124 and 125 to produce a common DNA amplification product; and (b) contacting the DNA of step (a) with a mutation specific reverse primer comprising SEQ ID NOS: 139 and a forward primer to amplify HIV-1 DNA containing a integrase 148H mutation. The forward primer is routinely selected based on the well-known criteria for such selections, which are described herein and elsewhere. For example, the reverse primer can be a primer comprising or consisting of SEQ ID NO:126.

An amplification method is provided comprising a forward primer or mixture of forward primers that amplifies an integrase 148H mutation, wherein the method further comprises using oligonucleotides having the nucleotides as set forth in SEQ ID NOS:140, 141 or combinations thereof. The oligonucleotides of SEQ ID NO: 140 and 141 are optionally used in combination at a concentration percentage of 80% and 20% respectively. These are examples of probes that can be used in mutation-specific PCR reactions for this mutation.

A method for amplifying the reverse transcriptase of HIV-1 is provided, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer comprising SEQ ID NO:7 and a reverse primer to amplify a region encoding the reverse transcriptase of HIV-1. The reverse primer is routinely selected based on the well-known criteria for such selections, which are described herein and elsewhere. For example, the reverse primer can be a primer comprising or consisting of SEQ ID NO:8. This can be a common amplification method of the invention. The total copy reaction can be used to provide the baseline for the mutation-specific real time PCR reactions disclosed herein. Alternatively, matched wildtype primers can be used as a control, as is known to one skilled in the art.

A method for amplifying the reverse transcriptase of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer comprising SEQ ID NO:7 and a reverse primer to amplify a region encoding the reverse transcriptase of HIV-1. The reverse primer is routinely selected based on the well-known criteria for such selections, which are described herein and elsewhere. For example, the reverse primer can be a primer comprising or consisting of SEQ ID NO:8.

The amplification methods disclosed herein can utilize reverse primers other than those exemplified. The exemplified reverse primers were found to work well. However, the requirements of the reverse primer in the present method are typical of reverse primers designed and used routinely, and other reverse primers can be routinely made and used. It is expected that the reverse primer will be within about 40 to 250 bases from the forward primer. It is also expected that the reverse primer will be positioned in a stable location lacking variability to a degree that would impede binding. The reverse primer is most likely to be located in the RT gene or the protease gene, but the exact location is routinely variable based on the usual criteria for reverse primer positioning.

Methods disclosed herein can further include detection, in the same mixture, of a specified RT mutation, a specified protease mutation, and/or a specified integrase mutation. The methods described herein are interchangeable and combinable depending on the desire of the user to detect one or a plurality of mutations in one or more HIV-1 sequences. For example, provided is a method for detecting a 184V mutation in the reverse transcriptase of HIV-1 and a 90M mutation in the protease of HIV-1, comprising (a) reverse transcribing RNA extracted from HIV-1 with a primer comprising SEQ ID NO:3 to produce a reverse transcription reaction product; (b) contacting the reverse transcription product of step (a) with a primer selected from the group consisting of SEQ ID NOS:1 and 2 to produce a DNA product; and (c) contacting the DNA product of step (b) with a primer set comprising SEQ ID NOS:33, 34, 35, 55, 78, 79, and 80 and a reverse primer to amplify HIV-1 DNA containing a 184V and a 90M mutation. The reverse primer is routinely selected based on the well-known criteria for such selections, which are described herein and elsewhere. For example, the reverse primer can be a primer comprising or consisting of SEQ ID NOS:36 and 81.

A method for detecting a 184V mutation in the reverse transcriptase of HIV-1 and a 90M mutation in the protease of HIV-1 is provided, comprising (a) contacting DNA with a reverse primer and a primer selected from the group consisting of SEQ ID NOS:1 and 2 to amplify the DNA; and (b) contacting the amplified DNA of step (a) with a primer set comprising SEQ ID NOS:33, 34, 35, 55, 78, 79, and 80 and a reverse primer to amplify HIV-1 DNA containing a 184V and a 90M mutation. The reverse primer is routinely selected based on the well-known criteria for such selections, which are described herein and elsewhere. For example, the reverse primer can be a primer comprising or consisting of SEQ ID NOS:36 and 81.

A variety of technologies related to real-time (or kinetic) PCR have been adapted to perform point mutation and SNP detection. Mutation detection using real-time amplification relies on the ability to detect amplified segments of nucleic acid as they are during the amplification reaction. Three basic real-time detection methodologies exist: (i) increased fluorescence of double strand DNA specific dye binding, (ii) decreased quenching of fluorescence during amplification, and (iii) increased fluorescence energy transfer during amplification (Wittwer, C. et al. Biotechniques 22:130-138, 1997). All of these techniques are non-gel based and each strategy is disclosed.

A variety of dyes are known to exhibit increased fluorescence in response to binding double stranded DNA. Production of wild type or mutation containing PCR products are continuously monitored by the increased fluorescence of dyes such as ethidium bromide or Syber Green as they bind to the accumulating PCR product. Note that dye binding is not selective for the sequence of the PCR product, and high non-specific background can give rise to false signals with this technique.

A second detection technology for real-time PCR, known generally as exonuclease primers (e.g., TaqMan® probes), utilizes the 5' exonuclease activity of thermostable polymerases such as Taq to cleave dual-labeled probes present in the amplification reaction (Wittwer, C. et al. Biotechniques 22:130-138, 1997; Holland, P et al PNAS 88:7276-7280, 1991, incorporated herein by reference). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of the polymerase during amplification, the quenching is greatly reduced leading to increased fluorescent signal.

An additional form of real-time PCR also capitalizes on the intramolecular quenching of a fluorescent molecule by use of a tethered quenching moiety. The molecular beacon technology utilizes hairpin-shaped molecules with an internally-quenched fluorophore whose fluorescence is restored by binding to a DNA target of interest (Kramer, R. et al. Nat. Biotechnol. 14:303-308, 1996, incorporated herein by reference). Increased binding of the molecular beacon probe to the accumulating PCR product can be used to specifically detect SNPs present in genomic DNA.

A final, general fluorescent detection strategy used for detection of point mutations and SNP in real time utilizes synthetic DNA segments known as hybridization probes in conjunction with a process known as fluorescence resonance energy transfer (FRET) (Wittwer, C. et al. Biotechniques 22:130-138, 1997; Bernard, P. et al. Am. J. Pathol. 153: 1055-1061, 1998, incorporated herein by reference). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154: 367, 1987 which is herein incorporated by reference for material at least related to hybridization of nucleic acids, which are incorporated herein in their entireties). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

This example describes the development and application of real-time PCR-based point mutation assays for the 103N and 184V mutations in the reverse transcriptase (RT) of HIV-1. The assay measures the differential amplifications of total copy and mutation-specific reactions that target codons of interest. In evaluating mutation-containing plasmids diluted in backgrounds of wild type plasmid, the assays were able to achieve a mutation detection limit of 0.04% and 0.2% 103N and 184V, respectively. To evaluate the performance of these assays with clinical specimens, 77 known wild-type samples were first analyzed. None of the wild-type samples was positive for the 184V mutation, while one sample (1.3%) scored positive for 103N. Conversely, in plasma samples known to have viruses carrying the 103N mutation and/or the 184V mutation, 103N was detected in 54 of 55 positive specimens (98%), and 184V in 65 of 67 (97%). To determine whether any mutation-containing samples were undetected by conventional sequence analysis, the present assays were applied to a test population of HIV-1-positive treatment-naïve persons documented to have RT mutations other than 103N and 184V. The 103N assay detected 4 positive samples (2.4%) in 165 plasma samples previously found absent of 103N (clones are currently being screened for the presence of low-level mutants). Likewise, in 173 samples previously determined to be negative for the 184V mutation, three samples scored positive (1.1%) for 184V by this assay. Two were later verified to have the mutation (at frequencies of 1.4% and 5.5%) by sequence analysis of clones. The data demonstrate that currently used sequence analysis is failing to detect resistant HIV-1 present as minority species in clinical specimens. The data also demonstrate that these real-time PCR assays for the detection of the 103N and 184V mutations are sensitive and specific. Given the low cost, high-throughput capability, and greater sensitivity than conventional testing, these assays will be useful for detecting drug resistance-associated mutations and could aid in the clinical management of HIV-1 infection.

Clinical Samples

Wild type HIV-1 subtype B samples were obtained from the plasma of 23 treatment-naïve persons (2) with no detectable resistance mutations, and from 54 sera collected in the early 1980's, prior to the development of antiretroviral drugs. 67 specimens confirmed by sequence analysis to have virus carrying the mutation comprised mutation-positive samples. The test population encompassed a second group of 173 treatment-naïve patients (partially referenced in 2), all with RT mutations other than 103N or 184V. Approximately 17% of the treatment-naïve specimens were from persons documented to be recently infected. Results obtained from evaluation of the wild type and mutation-confirmed samples were used to define the assay cutoffs.

Reverse Transcriptase-PCR

HIV-1 genomic RNA was extracted (Qiagen UltraSens RNA kit) from patient plasma or serum. Primary amplifications of HIV-1 template were generated by reverse transcriptase-PCR using primers that demarcated the first half of the RT sequence, or when desired, the forward primer was shifted upstream to also include the entire protease region. The minimum copy numbers from which these reactions could successfully amplify were 5 and 10 RNA copies, respectively.

Real-Time PCR

Baseline measurements for viral copies in test samples were determined using HIV-1 RT total copy primers with a total copy probe (FIG. 1A). Preliminary analysis for detecting the presence of the mutation was performed using primer mixtures to compensate for polymorphic variability in the primer binding sites. The 103N-specific mixture incorporated four different primers, and the 184V-specific reaction used three primers. The primers can be mixed at optimal ratios to equilibrate the differences in primer affinities. Examples of such ratios are provided below. It is recognized that the optimization of primer ratios is routine given the teaching of the primers and primer mixtures themselves. One of skill can envision alternative ratios.

The mutation-specific primers were designed to maximize specificity for annealing to the mutated nucleotide(s), thus having a reduced affinity for wild type sequences (3,4). The probes for each reaction were 5' labeled with FAM and quenched with QSY-7. The choice of fluorophore and quencher can be routinely varied. Common fluorophores include HEX, ROX, Texas Red, TAMRA, JOE, Cy3, Cy5, SYBR and VIC. There are others that often overlap the above spectra and can be used. The Bio-Rad fluorophore table contains a more complete listing of fluorophores that can be used for this method.

Degradation of the fluorescent probes during chain elongation removes the fluorophore from the proximity of the quencher and generates the fluorescent signals, reported as relative fluorescent units (RFU), that increase with each amplification cycle (FIG. 1B). The cycle number where the fluorescence emission exceeds the software-derived threshold is called the threshold cycle (CT) and is the unit of measure when comparing the differences in amplification levels ($\Delta$CT) of the total copy and mutation-specific reactions.

All reactions were performed using an iCycler real-time PCR system (Bio-Rad) and AmpliTaq Gold polymerase (Applied Biosystems). Any hot-start polymerase will work in this method. The differences between these are in their ability to extend from mismatched primers. Assay cutoffs (limits) are established for each polymerase. Other usable polymerases include, but are not limited to, AmpliTaq Platinum (Applied Biosystems) and iTaq (Bio-Rad). PCR annealing was at 50° C. for 15 seconds and extension at 60° C. for 30 seconds (See detailed PCT protocol below). Samples that were just above the cutoff (<2 CT) were again analyzed using individual primers for the mutation in order to increase the sensitivity of the test.

Assay Sensitivity

Assay detection limits were tested against dilutions of mutation-containing plasmid clones and from PCR products from both lab-adapted HIV-1 and patient-derived mutant virus spiked into a background of wild type virus template. The amounts of mutant input comprised 100%-0.001% of the total virus population.

Protocol for HIV Real-Time PCR Point Mutation Assays

I. Sample Preparation

Extract viral RNA from 100-1000 μL plasma or proviral DNA from ~7.5×10$^5$ cells (Qiagen Ultrasensitive Viral-Amp or Promega Wizard Genomic DNA kits, respectively)

II. For RNA Template

Primary (general) RT-PCR—

Use 5 μL extracted RNA per RT-PCR as follows:

(RT Step)—

Per reaction, add 5 μL RNA to a total of 40:1 of reagents prepared as follows:

| | | |
|---|---|---|
| DEPC water | 11 μL | |
| 10x buffer II | 4 μL | |
| MgCl$_2$ | 8 μL | (final conc. 5 mM) |
| dNTPs | 6 μL | (final conc. 1.5 mM each) |
| Reverse primer$^a$ | 4 μL | (final conc. 400 nM) |
| RNase inhibitor* | 1 μL | (20 U final) |
| MuLV RT* | 1 μL | (50 U final) |
| + 5 μL | | sample RNA |
| 40 μL | total | |

*Heat the RNA in aliquotted mastermix for 2 minutes at 94° C. then immediately place on ice prior to adding the RNase inhibitor and RT.

| RT reaction: |
|---|
| 39° C. for 1 hour, |
| 94° C. for 5 minutes, |
| 4° C. hold |

(PCR Step)—

Add the entire RT reaction to 60:1 PCR mix prepared per reaction as follows:

| | | |
|---|---|---|
| sterile water | 48 μL | |
| 10x buffer | 8 μL | |
| Forward primer$^a$ | 3 μL | (final conc. 120 nM) |
| AmpliTaq LD | 1 μL | (5 U final) |
| | 60 μL | mix |
| | + 40 μL | RT reaction |
| | 100 μL | total PCR |

PCR controls (in duplicate): 1) water=blank,
2) uninfected human DNA=(−),
3) plasmid @ 1000 copies/rxn spiked in human DNA= (+), or a 10$^5$→10$^2$/10 μL plasmid copy number series for quantitation (also see IV.).[†]

[†] The plasmid standards can be prepared and aliquotted as 40-cycle reactants of which 2 μL are used for the copy standards in each secondary reaction plate.

III. For DNA Template

Primary (General) PCR—

Per reaction, add 10:1 DNA (a higher concentration of template increases chances of encountering resistant proviruses) to a total of 100:1 of reagents prepared as follows:

| | | |
|---|---|---|
| Sterile water | 67 μL | |
| 10x buffer | 10 μL | |
| dNTPs | 6 μL | (final conc. 600:M each) |
| Forward primer<sup>a</sup> | 3 μL | (final conc. 120 nM) |
| Reverse primer<sup>a</sup> | 3 μL | (final conc. 120 nM) |
| AmpliTaq (Hi-Fi) | 1 μL | (5 U final) |
| | + 10 μL | sample DNA |
| | 100 μL | total PCR |

The 100 μL primary PCR reaction may be diluted (1:10-1:20) prior to the real-time PCR reaction to ensure the secondary reaction is not overloaded with template and to provide sufficient template for future studies.

1° PCR conditions:

| | |
|---|---|
| 95° C. for 4 minutes ▶ | |
| 95° C. for 45 seconds, | |
| 50° C. for 30 seconds, | |
| 72° C. for 2 minutes | x 40 cycles ▶ |
| 72° C. for 5 minutes ▶ | |
| 4° C. hold | |

IV. Mutation-Specific (Secondary) Real-Time PCR

Principle—A sequence-specific probe, labeled with a fluorophore and a quencher, anneals to a region flanked by locus-specific primers. PCR extension from the primers degrades the intervening probe releasing the quencher from the proximity of the fluorophore, thus increasing the level of detectable fluorescence. The amplification cycle at which the level of product (i.e., amount of degraded probe) is measurable above background, is the threshold cycle (TC). This value directly correlates with the amount of starting template and is the unit of measure when making comparisons between amplification levels.

Procedure—

Use 2 μL of each primary reaction in duplicate reactions of both a total copy and mutation-specific hot-start real-time PCR. Prepare for each of the secondary reactions by one or both of the following reaction parameters:

| | |
|---|---|
| sterile water | 30.5 μL |
| 10x buffer | 5 μL |
| Forward primer(s)<sup>b,c,d</sup> | 4 μL (final conc. 320 nM) |
| Reverse primer | 4 μL (final conc. 320 nM) |
| dNTPs | 2 μL (final conc. 400:M) |
| fluoro-probe | 2 μL (final conc. 160 nM) |
| AmpliTaq Gold (Life/ABI) | 0.5 μL (2.5 U final) |
| | + 2 μL primary reaction |
| | 50 μL total PCR reaction |
| sterile water | 14.25 μL |
| 10x buffer I | 2.5 μL |
| Forward primer<sup>a/b</sup> | 2 μL (final conc. 320 nM) |
| Reverse primer<sup>a/b</sup> | 2 μL (final conc. 320 nM) |
| dNTPs | 1 μL (final conc. 400 μM) |
| fluoro-probe | 1 μL (final conc. 160 nM) |
| AmpliTaq Gold | 0.25 μL (2.5 U final) |
| | + 2 μL primary reaction (RT-PCR product) |
| | 25 μL total PCR reaction |

2° Real-time PCR conditions:

| | |
|---|---|
| 95° C. for 11 minutes (includes normalization time) ▶ | |
| 95° C. for 30 seconds, | |
| 50° C. for 15 seconds, | |
| 59° C. for 30 seconds | x 45 cycles ▶ |
| 4° C. hold | |

The mutation-specific tests (c) can be qualitative, by comparing to the common (total copy) primers (b) using only the 1000 copy positive control, or quantitative, by using the wild type and mutation-inclusive plasmid copy number dilution series. The quantitation can be performed without or in conjunction with a separate mutation-independent (mi) test (d), for quantitation by comparing the CT of the mutation reaction to the CT of the primer complementary to the shared overlapping sequence (i.e., same locus) (for examples of mi primers, see the primer list below).

All mutation-specific PCRs are evaluated relative to the concomitant total copy (or wild type) reaction, the difference being ΔCT. Mutation-specific reactions with a ΔCT below the experimentally derived cutoff are scored positive.

An advantage of the present invention is in detection sensitivity of the various subtypes of HIV from various countries of the world. For example, the sets disclosed in the primer set below are particularly sensitive to detection of HIV subtypes across the spectrum of HIV.

ReTi-HIV Assay Oligonucleotide List:

<sup>a</sup> Primers for the RT-PCR reaction:

```
Subtype B
RTPF1 (includes protease)
                                        (SEQ ID NO: 1)
5'-CCT CAG ATC ACT CTT TGG CAA CG RTPF2 (only RT)
                                        (SEQ ID NO: 2)
5'-AAA GTT AAA CAA TGG CCA TTG ACA G RTPREV
                                        (SEQ ID NO: 3)
5'-ATC CCT GCA TAA ATC TGA CTT GC Subtype C
RTPF1C (includes protease)
                                        (SEQ ID NO: 4)
5'-CCT CAA ATC ACT CTT TGG CAG CG RTPF2C (RT only)
                                        (SEQ ID NO: 5)
5'-AGG TTA AAC AAT GGC CAT TGA CAG AAG RTP-RC
                                        (SEQ ID NO: 6)
5'-CTG GGT AAA TCT GAC TTG CCC A
```

Primers below are for the listed mutations. All forward primers for each mutation can be mixed for general surveillance testing or the primers can be used individually or mixed and matched for detecting/monitoring distinct polymorphisms associated with that mutation. The primer proportions exemplified for these mixtures are routinely adjustable using the optimization methods routinely practiced in this field. IUPAC codes: M=A or C; R=A or G; W=A or T; S=C or G; Y=C or T; K=G or T Notes: FAM=6-carboxyfluorescein, however, any fluorophore may be used; the " " marks are where the quencher is placed <sup>#</sup> 67 and 69 REV are the same as the comREV primer <sup>§</sup> Test performed in reverse orientation where the reverse primers detect the mutation <sup>&</sup></sup> Test for the wildtype codon (absence of mutation)

<sup>†</sup> Same as the 41L probe

<sup>£</sup> Same as the RT-PCR primer RTPF2

| Codons | Label | Oligonucleotide sequence[§] |
|---|---|---|
| [b]Common[@] (copy number) probe[#] | ComFWD ComREV | 5'-CTT CTG GGA AGT TCA ATT AGG AAT ACC (SEQ ID NO: 7) 5'-CCT GGT GTC TCA TTG TTT ATA CTA GGT (SEQ ID NO: 8) 5'-*FAM*-TGG ATG TGG GIG A"T"G CAT ATT TYT CAR TTG CCT TA (SEQ ID NO: 9) |

[c]Mutation
Subtype B
Reverse transcriptase
41L Set 1

| | | |
|---|---|---|
| 41L F1 | | 5'-AAA AGC ATT ART RGA AAT YTG TRC AGG AC (SEQ ID NO: 62) |
| 41L F2 | | 5'-AAT AAA AGC ATT ART RGA AAT YTG TRC AGC AT (SEQ ID NO: 63) |
| 41L F3 | | 5'-TAA AAG CAT TAR TRG AAA TYT GTR CAK GTC (SEQ ID NO: 64) |
| 41L F4 | | 5'-AAG CAT TAR TRG AAA TYT GTR CAK GGC (SEQ ID NO: 65) |
| 41L REV | | 5'-CCT AAT TGA ACT TCC CAG AAG TC (SEQ ID NO: 66) |
| 41L probe | | 5'-FAM-TTG GGC CTG AAA A"T"C CAT ACA ATA CTC CAG TAT TT (SEQ ID NO: 67) |

41L Set 2

| | | |
|---|---|---|
| 41L F2 | | 5'-AAT AAA AGC ATT ART RGA AAT YTG TRC AGC AT (SEQ ID NO: 63) |
| 41L F5 | | 5'-AAT WAA AGC ATT ART RGA AAT YTG TRC WGC AT (SEQ ID NO: 96) |
| 41L F6 | | 5'-AAA AGC ATT ART RGA AAT YTG TRC AGG AC (SEQ ID NO: 97) |
| 41L F3 | | 5'-TAA AAG CAT TAR TRG AAA TYT GTR CAK GTC (SEQ ID NO: 64) |
| 41L F4 | | 5'-AAG CAT TAR TRG AAA TYT GTR CAK GGC (SEQ ID NO: 65) |
| 41L REV | | 5'-CCT AAT TGA ACT TCC CAG AAG TC (SEQ ID NO: 66) |
| 41L probe | | 5'-FAM-TTG GGC CTG AAA A"T"C CAT ACA ATA CTC CAG TAT TT (SEQ ID NO: 67) |

65R Set 1

| | | |
|---|---|---|
| 65R F1 | | 5'-CAT AYA ATA CYC CAR TAT TTG YCA TAA AAA G (SEQ ID NO: 10) |
| 65R REV | | 5'-CCT GGT GTC TCA TTG TTT ATA CTA GGT (SEQ ID NO: 11) |
| 65R probe | | 5'-*FAM*-TGG ATG TGG GTG A"T"G CAT ATT TYT CAR TTC CCT TA (SEQ ID NO: 9) |
| 65-69 probe | | 5'-FAM-TAG TAG ATT "T" CAG AGA ACT TAA TAA GAG AAC TCA AGA CT (SEQ ID NO: 68) |

65R Set 2

| | | |
|---|---|---|
| 65R F2 | | 5'-ACA ATA CTC CAR TAT TTG CCA TAA RCA G (SEQ ID NO: 98) |
| 65R REV | | 5'-CCT GGT GTC TCA TTG TTT ATA CTA GGT (SEQ ID NO: 11) |
| 65-69 probe2 | | 5'-FAM-TCA GAG AAC "T" TAA TAA RAG AAC TCA AGA CTT CTG GGA (SEQ ID NO: 99) |

67N

| | | |
|---|---|---|
| 67N F2 | | 5'-AAT ACT CCA RTA TTT GYC ATA ARG AAR GCA A (SEQ ID NO: 69) |
| 67N F3 | | 5'-ATA CTC CAR TAT TTG YCA TAA AGA ARG CGA (SEQ ID NO: 70) |
| 67 REV[#] | | 5'-CCT GGT GTC TCA TTG TTT ATA CTA GGT (SEQ ID NO: 8) |
| 65-69 probe | | 5'-FAM-TAG TAG ATT "T" CAG AGA ACT TAA TAA GAG AAC TCA AGA CT (SEQ ID NO: 68) |

69T Set 1

| | | |
|---|---|---|
| 69T F1[‡] | | 5'-RTA TTT GCC ATA AAG AAR AAR RAY AAT AC (SEQ ID NO: 12) |
| 69T F2[‡] | | 5'-RTA TTT GCC ATA AAG AAR AAR RAY AAC AC (SEQ ID NO: 13) |
| 69T REV | | 5'-GTA TGG TAA ATG CAG TAT ACT TCC T (SEQ ID NO: 14) |
| [d]69Tmi | | 5'-CCA RTA TTT GCC ATA AAG AAR AAR RAY AGT (SEQ ID NO: 15) |
| 69T probe | | 5'-*FAM*-TGG ATG TGG GTG A"T"G CAT ATT TYT CAR TTC CCT TA (SEQ ID NO: 9) |

69T Set 2

| | | |
|---|---|---|
| 69T F1[&] | | 5'-RTA TTT GCC ATA AAG AAR AAR RAY AAT AC (SEQ ID NO: 12) |
| 69T F2 | | 5'-RTA TTT GCY ATA AAG AAR AAR GAY AGC AC (SEQ ID NO: 71) |
| 69T REV[#] | | 5'-CCT GGT GTC TCA TTG TTT ATA CTA GGT (SEQ ID NO: 8) |
| [d]69Tmi | | 5'-CCA RTA TTT GCC ATA AAG AAR AAR RAY AGT (SEQ ID NO: 15) |
| 65-69 probe | | 5'-FAM-TAG TAG ATT "T" CAG AGA ACT TAA TAA GAG AAC TCA AGA CT (SEQ ID NO: 68) |

70R Set 1

| | | |
|---|---|---|
| 70R F1 | | 5'-TRT TTG CCA TAA AGA AAA AAR AYA GTA MCA G (SEQ ID NO: 16) |
| 70R F2 | | 5'-TTG CCA TAA AGA AAA AAR ACA GTG ACA G (SEQ ID NO: 17) |
| 70R F3 | | 5'-TTG CCA TAA AGA AAA AAR ACA GYR ACA G (SEQ ID NO: 18) |
| 70R F4 | | 5'-GCC ATA AAG AAA AAA RAC RGT RAC GG (SEQ ID NO: 19) |
| 70R REV | | 5'-GTA TGG TAA ATG CAG TAT ACT TCC T (SEQ ID NO: 20) |
| [d]70Rmi | | 5'-AGT ATT GCC ATA AAG GAA AAA ARA CAG TAM TA (SEQ ID NO: 21) |
| 70R probe | | 5'-*FAM*-TGG ATG TGG GTG A"T"G CAT ATT TYT CAR TTC CCT TA (SEQ ID NO: 9) |

-continued

```
70R Set 2
70 F1ᴱ          5'-AAA GTT AAA CAA TGG CCA TTG ACA G (SEQ ID NO: 2)
70R REV1ˢ       5'-GTT CTC TRA AAT CTA YTA WTT TTC TCC CTC (SEQ ID NO: 72)
70R REV2        5'-TTC TCT RAA ATC TAY TAW TTT TCT CCC CC (SEQ ID NO: 73)
ᵈ70mi           5'-AGT ATT TGC CAT AAA GAA AAA ARA CAG TAM TA (SEQ ID NO: 21)
70R probe†      5'-FAM-TTG GGC CTG AAA A"T"C CAT ACA ATA CTC CAG TAT TT (SEQ ID NO: 67)

70R Set3
70 F2ᴱ          5'-AGA RAT TTG TAC AGA RAT GGA AAA GGA AG (SEQ ID NO: 100)
70R REV1ˢ       5'-GTT CTC TRA AAT CTA YTA WTT TTC TCC CTC (SEQ ID NO: 72)
70R REV2        5'-TTC TCT RAA ATC TAY TAW TTT TCT CCC CC (SEQ ID NO: 73)
70R probe†      5'-FAM-TTG GGC CTG AAA A"T"C CAT ACA ATA CTC CAG TAT TT (SEQ ID NO: 67)

103N
103N F1         5'-TCC HGC AGG GTT AAA RAA GGA C (SEQ ID NO: 22)
103N F2         5'-TCC CKC WGG GTT AAR AAG GGA C (SEQ ID NO: 23)
103N F3         5'-CAT CCH GCA GGR TTA AAA AAG GGC (SEQ ID NO: 24)
103N F4         5'-CAT CCC GCA GGG TTA AAA VAG GAT (SEQ ID NO: 25)
103N REV        5'-GTA TGG TAA ATG CAG TAT ACT TCC T (SEQ ID NO: 26)
ᵈ103Nmi         5'-CAT CCH GCA GGR CTA AAA AAG AA (SEQ ID NO: 27)
103N probe      5'-FAM-TGG ATG TGG GTG A"T"G CAT ATT TYT CAR TTC CCT TA (SEQ ID NO: 9)

181C
181C F1         5'-AAA ACA AAA YCC AGA MAT GRT TGG CTG (SEQ ID NO: 28)
181C F2         5'-GAA AAC AAA AYC CAR AMA TRG TTG GHT G (SEQ ID NO: 29)
181C REV        5'-CAG GAT GGA GTT CAT AAC CCA T (SEQ ID NO: 30)
ᵈ181Cmi         5'-TTY AGA AAA CAA AAY CCA GAM ATG RTT ATM T (SEQ ID NO: 31)
181C probe      5'-FAM-TAG GAT CTG ACT TAG AAA "T"AG GRC AGC ATA GAR C (SEQ ID NO: 32)

184V
184V F1         5'-AAA TCC ARA MMT ART TAT MTR TCA GCA CG (SEQ ID NO: 33)
184V F2         5'-AAA ICC AGA MAT ART TAT CTR TCA GCA CG (SEQ ID NO: 34)
184V F3         5'-AAA YCC ARA MAT ART TAT YCA GCA TG (SEQ ID NO: 35)
184V REV        5'-CAG GAT GGA GTT CAT AAC CCA T (SEQ ID NO: 36)
ᵈ184Vmi         5'-AAR CAA AAY CCA RAM ATA RTT ATC TRT CAA TAY (SEQ ID NO: 37)
184V probe      5'-FAM-TAG GAT CTG ACT TAG AAA "T"AG GRC AGC ATA GAR C (SEQ ID NO: 32)

215 Y,F,S,C,D
215Y F1         5'-ASA RCA TCT GTK GAR RTG GGG RYT CTA (SEQ ID NO: 40)
215F F1         5'-ASA RCA TCT GTK GAR RTG GGG RYT CTT (SEQ ID NO: 41)
215S F1         5'-ARC ATC TGT KGA RGT GGG GRY TCT C (SEQ ID NO: 42)
215C F1         5'-ARC ATC TGT KGA RGT GGG GRY TCT G (SEQ ID NO: 43)
215D F1         5'-SAR CAT CTG TKG ARR TGG GGR YTC GA (SEQ ID NO: 44)
215REV          5'-CTT CTG TAT GTC ATT GAC AGT CC (SEQ ID NO: 45)
ᵈ215mi          5'-SAA CAT CTG TTG ARG TGG GGR YTT (SEQ ID NO: 46)
probe           5'-FAM-TGG ACA GTA CAG CC"T" ATA RTG CTG CCA GA (SEQ ID NO: 47)

215T Set 1
215T F1‡        5'-ACA TCT GTK GAR GTG GGG RYT CAC (SEQ ID NO: 38)
215T F2‡        5'-ASA AYA TCT GTT RAR GTG GGG RTT CAC (SEQ ID NO: 39)
215 REV         5'-CTT CTG TAT GTC ATT GAC ACT CC (SEQ ID NO: 45)
ᵈ215mi          5'-SAA CAT CTG TTG ARG TGG GGR YTT (SEQ ID NO: 46)
probe           5'-FAM-TGG ACA GTA CAG CC"T" ATA RTG CTG CCA GA (SEQ ID NO: 47)

215T Set 2
215T F1&        5'-AAC ATC TGT KGA RGT GGG GRY TCA C (SEQ ID NO: 74)
215T F2         5'-AAC ATY TGT TAA RGT GGG GRY TCA C (SEQ ID NO: 75)
215 REV         5'-CTT CTG TAT GTC ATT GAC AGT CC (SEQ ID NO: 45)
ᵈ215mi          5'-SAA CAT CTG TTG ARG TGG GGR YTT (SEQ ID NO: 46)
215 probe1      5'-FAM-TAT GAA CTC CA"T"C CTG ATA AAT GGA CAG TAC ARC (SEQ ID NO: 76)
215 probe2      5'-FAM-TAT GAG CTC CA"T"C CTG ATA AAT GGA CAG TRC (SEQ ID NO: 77)

215T Set 3
215T F3&        5'-CAA CAT YTG TTA ARG TGG GGR GAT AC (SEQ ID NO: 101)
215T F2         5'-AAC ATY TGT TAA RGT GGG GRY TCA C (SEQ ID NO: 75)
215 REV         5'-CTT CTG TAT GTC ATT GAC AGT CC (SEQ ID NO: 45)
ᵈ215mi          5'-SAA CAT CTG TTG ARG TGG GGR YTT (SEQ ID NO: 46)
215 probe1      5'-FAM-TAT GAA CTC CA"T"C CTG ATA AAT GGA CAG TAC ARC (SEQ ID NO: 76)
215 probe2      5'-FAM-TAT GAG CTC CA"T"C CTG ATA AAT GGA CAG TRC (SEQ ID NO: 77)

Protease
30N
30N F1          5'-GCT YTA TTA GAY ACA GGR GCA GGT A (SEQ ID NO: 48)
30N F2          5'-GCT CTA TTM GAY ACA GGA GCW GGT A (SEQ ID NO: 49)
30N REV         5'-TGG TAC AGT TTC AAT AGG ACT AAT GGG (SEQ ID NO: 50)
```

-continued

```
ᵈ30Nmi          5'-CTY TAT TMG AYA CAG GRG CAG GTA (SEQ ID NO: 51)
30N probe       5'-FAM-TAA RAC AGT ATG ATC AGR TAC CCA "T"AG AAA TCT GTG GAC-3'
                (SEQ ID NO: 52)

90M Set 1
90M F1          5'-CTG YCA ACR TAA TTG GAA GAA ATC CGA (SEQ ID NO: 53)
90M F2          5'-CTR CCA ACA TAA TTG GAA GAA AYC CGA (SEQ ID NO: 54)
90M F3          5'-CTR YCA ACR TAA TTG GAA GAA ATC CAA (SEQ ID NO: 55)
90 REV          5'-CTT CTG TCA ATG GCC ATT GTT AAA C (SEQ ID NO: 56)
ᵈ90Mmi          5'-CCT GYC AAC RTA ATT GGA AGA AAY CT (SEQ ID NO: 57)
90M probe       5'-FAM-TGT ACC AGT AAA AT"T" AAA GCC AGG AAT GGA TGG (SEQ ID NO: 58)

90M Set 2
90M F1          5'-TGY CAA CRT AAT TGG RAG RAA TCG GA (SEQ ID NO: 78)
90M F2          5'-CTR YCA ACR TAA TTG GAA GRA ATK GGA (SEQ ID NO: 79)
90M F3          5'-CTR YCA ACR TAA TTG GAA GAA ATC CAA (SEQ ID NO: 55)
90M F4          5'-RYC AAC RTA ATT GGR AGA GAY CGG A (SEQ ID NO: 80)
90M REV         5'-AAT GCT TTT ATT TTT TCT TCT GTC AAT GGC (SEQ ID NO: 81)
ᵈ90Mmi          5'-CCT GYC AAC RTA ATT GGA AGA AAY CT (SEQ ID NO: 57)
90M probe       5'-FAM-TAA ATTC TTC CCA "T" TAG TCC TAT TGA AAC TGT ACC AGT AAA
                (SEQ ID NO: 82)

Subtype AE
Reverse Transcriptase
65R Set (Subtype AE)
HIV-AE_K65R.1F  5'-ATAYAATACTCCARTATTTTGCTATAAACAG (SEQ ID NO: 113)
HIV-B ComRev    5'-TGG TGT CTC ATT GTT TRT ACT AGG TA (SEQ ID NO: 114
AE CoM 3.1Probe 5'-FAM-TCAGTAACAG"T"ACTAGATGTGGGAGATGCATAT (SEQ ID NO: 115)
AE Com 3.2P     5'-FAM-TCAGTAACAG"T"ACTGGATGTGGGGGATGCATAT (SEQ ID NO: 116)

Subtype C
Reverse transcriptase
65R Set 4
65R.6F          5'-CAATACTCCAGTATTTGTCATACCAAG (SEQ ID NO: 117)
HIV-C 65R.5.1F  5'-AACACTCCARTATTTGCYATACCAAG (SEQ ID NO: 118)
HIV-C 65.1REV   5'-TYTTTAACCCTGMTGGGTGTGGTAT (SEQ ID NO: 119)
HIV-C 65.1P     5'-FAM-TCAGGGARC"T"CAATAAAAGAACTCAAGACTTYTGGGA (SEQ ID NO: 120)
HIV-C 65.2P     5'-FAM-TCAGGGAAC"T"YAAYAAAAGAACTCAAGACTTYTGGGA (SEQ ID NO: 121)

65R Set 5
HIV-C 65R.5.1F  5'-AACACTCCARTATTTGCYATACCAAG (SEQ ID NO: 118)
HIV-C 6F        5'-CAA TAC TCC AGT ATT TGT CAT ACC AAG-3' (SEQ ID NO: 117)
HIV-C 6.1F      5'-YAA YAC TCC AGT ATT TGY CAT ACC AAG-3' (SEQ ID NO: 122)
HIV-C 65.1REV   5'-TYTTTAACCCTGMTGGGTGTGGTAT (SEQ ID NO: 119)
HIV-C 65.1P     5'-FAM-TCAGGGARC"T"'CAATAAAAGAACTCAAGACTTYTGGGA (SEQ ID NO: 120)
HIV-C 65.2P     5'-FAM-TCAGGGAAC"T"YAAYAAAAGAACTCAAGACTTYTGGGA (SEQ ID NO: 121)

103N
103N F1         5'-CCC AGT AGG RTT AAA RAA GGA C (SEQ ID NO: 59)
103N F2         5'-CCC AKC RGG GTT RAA AGA GGA C (SEQ ID NO: 60)
103N F3         5'-CCC AGC AGG RTT AAA AVA GGA T (SEQ ID NO: 61)
103N REV        5'-GTA TGG TAA ATG CAG TAT ACT TCC T (SEQ ID NO: 26)
103N probe      5'-FAM-TGG ATG TGG GTG A"T"G CAT ATT TYT CAR TTC CCT TA (SEQ ID NO: 9)

181C
181C F1         5'-GRA CAM AAA ATC CAG AAA TAG TYG CCT G (SEQ ID NO: 83)
181C F2         5'-ACA MRA AAT CCA GAA ATA GTY GCT TG (SEQ ID NO: 84)
181/184 REV     5'-CAG GAT GGA GTT CAT AAC CCA T (SEQ ID NO: 85)
181/184 probe1  5'-FAM-TAG GAT CTG ATT "T" AGA AAT AGG GCA ACA TAG RAC (SEQ ID NO: 86)
181/184 probe2  5'-FAM-TAG GAT CTG ATT "T" AGA AAT AAA GCA ACA TAG RAC (SEQ ID NO: 87)

184V Set 1
184V F1         5'-AAA AYC AGA MAT AR TYA TCT RYC AGC ATG (SEQ ID NO: 88)
184V F2         5'-MAA AAY CCA RAM ATA RTY ATM TRT CAG CAC G (SEQ ID NO: 89)
181/184 REV     5'-CAG GAT GGA GTT CAT AAC CCA T (SEQ ID NO: 85)
181/184 probe1  5'-FAM-TAG GAT CTG ATT "T" AGA AAT AGG GCA ACA TAG RAC (SEQ ID NO: 86)
181/184 probe2  5'-FAM-TAG GAT CTG ATT T" AGA AAT AAA GCA ACA TAG RAC (SEQ ID NO: 87)

184V Set 2
184V F3         5'-AAA AYC AGR AAT AR TYA TCT RTC AGC ATG (SEQ ID NO: 102)
184V F4         5'-AAY CCA GAM ATA RTY ATC TRT CAG CAC G (SEQ ID NO: 103)
184V F5         5'-AAA AYC AGA RAT AR TYA TYT RTC AGC ATG (SEQ ID NO: 104)
181/184 REV     5'-CAG GAT GGA OTT CAT AAC CCA T (SEQ ID NO: 85)
181/184 probe1  5'-FAM-TAG GAT CTG ATT "T" AGA AAT AGG GCA ACA TAG RAC (SEQ ID NO: 86)
181/184 probe2  5'-FAM-TAG GAT CTG ATT "T" AGA AAT AAA GCA ACA TAG RAC (SEQ ID NO: 87)
```

```
Integrase (primers and probes)
HIV-IN GEN.3F, GTG ATA AAT GTC ARY TAA AAG GRG AAG C (SEQ ID NO: 124) For RT-PCR HIV-IN GEN.3R, CTT TCC AAA STG GRT CTC TGC TG: (SEQ ID NO: 125) For RT-PCR HIV-IN GEN.4F, CAT GGA CAA GTA GAC TGT AGY CCA (SEQ ID NO: 126): forward primer
for common reaction and 148 and 155 mutations.

HIV-IN SEQ.3R, GTC CCT GTA ATA AAC YCG AAA ATT TTG (SEQ ID NO: 127): sequencing

HIV-IN GEN.4R, CTY TRG TYT GTA TGT CTG TTG CTA TYA TG (SEQ ID NO: 128): for nested PCR HIV-IN COM.1BR, CAG CYT GMT CTC TTA CYT GTC CTA (SEQ ID NO: 129): used in
common reaction with GEN.4F HIV-IN 138.1R, CTA YTA TTC TTT CYC CTG CAC TGT A (SEQ ID NO: 130): Reverse for 138
and 140 mutations HIV-B-IN 138.2P, TCA AGC TGA ACA TC"T" YAA RAC AGC AGT ACA RAT GGC (SEQ ID NO: 131):

HIV-13-IN 138.1P, TCA GGC TGA ACA TC"T" YAA RAC AGC AGT ACA RAT GGC (SEQ ID
NO: 132): 138 probes used for 138 and 140 mutations

HIV-B IN 138K.1F, GTG GGC RGG RAT CAA RCT GA (SEQ ID NO: 133)

HIV-B IN 140S.1F, GGC RGG RAT CAA GCA GRA ATC TA (SEQ ID NO: 134)

HIV-B-IN SEQ.3F, GTA GCC AGT GGA TAY ATA GAA GCA G (SEQ ID NO: 135): sequencing

HIV-IN SEQ.3R, GTC CCT GTA ATA AAC YCG AAA ATT TTG (SEQ ID NO: 136): sequencing

HIV-B-IN 155H.1R, ACC TGT CCT ATA ATT TTC TTT AAT TCY TTC TG (SEQ ID NO: 137)

HIV-B-IN 148R.1R, CTT TAT TCA TAG ATT CTA CTA CYC GTC (SEQ ID NO: 138)

HIV-B-IN 148H.2R, CTT TAA TTC TTT ATT CAT AGA TTC TAC TAC YCG A (SEQ ID NO: 139)

HIV-B IN COM.4.3P, TCT AAA AAT "T"AG CAG GAA GAT GGC CAG TRA MAA CAA TAC
ATA C (SEQ ID NO: 140)

HIV-B IN COM.4.4P, TTT TAA AAC "T"AG CAG GAA GAT GGC CAG TRA MAA CAA TAC
ATA C (SEQ ID NO: 141)
COM probes are used for common reaction and 148 and 155 mutation tests.
```

It is appreciated that nucleotides marked within quotation marks (e.g. "T") are optionally bound to a quencher molecule. Probes are optionally labeled at the 5' nucleotide with a fluorophore that is matched to a quencher molecule.

Simian Immunodeficiency virus (SIV) has strong clinical, pathological, virological and immunological analogies with HIV infection of humans. Infection of macaques with SW provides a valuable model for exploring crucial issues related to both the pathogenesis and prevention of HIV infection. The model offers a unique setting for mutation detection testing, preclinical evaluation of drugs, vaccines and gene-therapies against HIV, and can identify many virus and host determinants of lentiviral disease. As such, the present invention can be utilized in conjunction with SIV nucleotide sequences. Provided below are exemplary SIV sequences for use with the present invention. The SIVmac 65R mutation-specific reaction can be compared against the total copy (common) reaction in the same way as described previously for HIV oligonucleotides.

```
Macaque SIV Reverse Transcriptase
Accession number: AY588945, M33262, AY599201, AY597209, M19499
Exemplary Sequence
                                                                            (SEQ ID NO: 105)
    1       CCCATAGCTA AAGTAGAGCC TGTAAAAGTC GCCTTAAAGC CAGGAAAGGA TGGACCAAAA
            TTGAAGCAGT GGCCATTATC 81       AAAAGAAAAG ATAGTTGCAT TAAGAGAAAT CTGTGAAAAG ATGGAAAAGG ATGGTCAGTT
            GGAGGAAGCT CCCCCGACCA 161       ATCCATACAA CACCCCCACA TTTGCTATAA AGAAAAAGGA TAAGAACAAA TGGAGAATGC
            TGATAGATTT TAGGGAACTA 241       AATAGGGTCA CTCAGGACTT TACGGAAGTC CAATTAGGAA TACCACACCC TGCAGGACTA
            GCAAAAAGGA AAAGAATTAC 321       AGTACTGGAT ATAGGTGATG CATATTTCTC CATACCTCTA GATGAAGAAT TTAGGCAGTA
            CACTGCCTTT ACTTTACCAT
```

-continued

| Macaque SIV Reverse Transcriptase |
|---|

| | |
|---|---|
| 401 | CAGTAAATAA TGCAGAGCCA GGAAAACGAT ACATTTATAA GGTTCTGCCT CAGGGATGGA AGGGGTCACC AGCCATCTTC |
| 481 | CAATACACTA TGAGACATGT GCTAGAACCC TTCAGGAAGG CAAATCCAGA TGTGACCTTA GTCCAGTATA TGGATGACAT |
| 561 | CTTAATAGCT AGTGACAGGA CAGACCTGGA ACATGACAGG GTAGTTTTAC AGTCAAAGGA ACTCTTGAAT AGCATAGGGT |
| 641 | TTTCTACCCC AGAAGAGAAA TTCCAAAAAG ATCCCCCATT TCAATGGATG GGTACGAAT TGTGGCCAAC AAAATGGAAG |
| 721 | TTGCAAAAGA TAGAGTTGCC ACAAAGAGAG ACCTGGACAG TGAATGATAT ACAGAAGTTA GTAGGAGTAT TAAATTGGGC |
| 801 | AGCTCAAATT TATCCAGGTA TAAGAACAAA ACATCTCTGT AGGTTAATTA GAGGAAAAAT GACTCTAACA GAGGAAGTTC |
| 881 | AGTGGACTGA GATGGCAGAA GCAGAATATG AGGAAAATAA AATAATTCTC AGTCAGGAAC AAGAAGGATG TTATTACCAA |
| 961 | GAAGGCAAGC CATTAGAAGC CACGGTAATA AAGAGTCAGG ACAATCAGTG GTCTTATAAA ATTCACCAAG AAGACAAAAT |
| 1041 | ACTGAAAGTA GGAAAATTTG CAAAGATAAA GAATACACAT ACCAATGGAG TGAGACTATT AGCACATGTA ATACAGAAAA |
| 1121 | TAGGAAAGGA AGCAATAGTG ATCTGGGGAC AGGTCCCAAA ATTCCACTTA CCAGTTGAGA AGGATGTATG GAACAGTGG |
| 1201 | TGGACAGACT ATTGGCAGGT AACCTGGATA CCGGAATGGG ATTTTATCTC AACACCACCG CTAGTAAGAT TAGTCTTCAA |
| 1281 | TCTAGTGAAG GACCCTATAG AGGGAGAAGA AACCTATTAT ACAGATGGAT CATGTAATAA ACAGTCAAAA GAAGGGAAAG |
| 1361 | CAGGATATAT CACAGATAGG GGCAAAGACA AAGTAAAAGT GTTAGAACAG ACTACTAATC AACAAGCAGA ATTGGAAGCA |
| 1441 | TTTCTCATGG CATTGACAGA CTCAGGGCCA AAGGCAAATA TTATAGTAGA TTCACAATAT GTTATGGGAA TAATAACAGG |
| 1521 | ATGCCCTACA GAATCAGAGA GCAGGCTAGT TAATCAAATA ATAGAAGAAA TGATTAAAAA GTCAGAAATT TATGTAGCAT |
| 1601 | GGGTACCAGC ACACAAAGGT ATAGGAGGAA ACCAAGAAAT AGACCACCTA GTTAGTCAAG GGATTAGACA AGTTCTCTTC |
| 1681 | TTGGAAAAGA TAGAGCCAGC ACAAGAAGAA CATGATAAAT ACCATAGTAA TGTAAAAGAA TTGGTATTCA AATTTGGATT |
| 1761 | ACCCAGAATA GTGGCCAGAC AGATAGTAGA CACCTGTGAT AAATGTCATC AGAAAGGAGA GGCTATACAT GGGCAGGCAA |
| 1841 | ATTCAGATCT AGGGACTTGG CAAATGGATT GTACCCATCT AGAGGGAAAA ATAATCATAG TTGCAGTACA TGTAGCTAGT |
| 1921 | GGATTCATAG AAGCAGAGGT AATTCCACAA GAGACAGGAA GACAGACAGC ACTATTTCTG TTAAAATTGG CAGGCAGATG |
| 2001 | GCCTATTACA CATCTACACA CAGATAATGG TGCTAACTTT GCTTCGCAAG AAGTAAAGAT GGTTGCATGG TGGGCAGGGA |
| 2081 | TAGAGCACAC CTTTGGGGTA CCATACAATC CACAGAGTCA GGGAGTAGTG GAAGCAATGA ATCACCACCT GAAAAATCAA |
| 2161 | ATAGATAGAA TCAGGGAACA AGCAAATTCA GTAGAAACCA TAGTATTAAT GGCAGTTCAT TGCATGAATT TTAAAAGAAG |
| 2241 | GGGAGGAATA GGGGATATGA CTCCAGCAGA AAGATTAATT AACATGATCA CTACAGAACA AGAGATACAA TTTCAACAAT |
| 2321 | CAAAAAACTC AAAATTTAAA AATTTTCGGG TCTATTACAG AGAAGGCAGA GATCAACTGT GGAAGGGACC CGGTGAGCTA |

-continued

| Macaque SIV Reverse Transcriptase |
|---|

```
2401       TTGTGGAAAG GGGAAGGAGC AGTCATCTTA AAGGTAGGGA CAGACATTAA GGTAGTACCC
           AGAAGAAAGG CTAAAATTAT

2481       CAAAGATTAT GGAGGAGGAA AAGAGGTGGA TAGCAGTTCC CACATGGAGG ATACCGGAGA
           GGCTAGAGAG GTGGCATAGC

2561       CTCATAAAAT ATCTGAAATA TAAAACTAAA GATCTACAAA AGGTTTGCTA TGTGCCCCAT
           TTTAAGGTCG GATGGGCATG

2641       GTGGACCTGC AGCAGAGTAA TCTTCCCACT ACAGGAAGGA AGCCATTTAG AAGTACAAGG
           GTATTGGCAT TTGACACCAG

2721       AAAAAGGGTG GCTCAGTACT TATGCAGTGA GGATAACCTG GTACTCAAAG AACTTTTGGA
           CAGATGTAAC ACCAAACTAT

2901       GCAGACATTT TACTGCATAG CACTTNTTTC CCTTGCTTTA CAGCGGGAGA AGTGAGAAGG
           GCCATCAGGG GAGAACAACT

2881       GCTGTCTTGC TGCAGGTTCC CGAGAGCTCA TAAGTACCAG GTACCAAGCC TACAGTACTT
           AGCACTGAAA GTAG
```
Genome Location: 1954 . . . 4907
Additional Similar Nucleotide Examples: Accession Numbers: U65787
Protein: Accession Number: AAV65312

SIVmac
RT-PCR reaction:
RTP F1      5'-CAA AAG AAA AGA TAG TTG CAT TAA GAG AAA T (SEQ ID NO: 106)

RTP REV     5'-GCC ACA ATT CGT ACC CCA TCC A (SEQ ID NO: 107)

Reverse transcriptase
Total copy  com F1     5'-CAT ACA ACA CCC CCA CAT TTG CTA TA
                       (SEQ ID NO: 108)
            com REV    5'-AGT CCT GCA GGG TGT GGT ATT C
                       (SEQ ID NO: 109)

65R         65R F1     5'-ACT CCC ACA TTT GCY ATA GCG AG
                       (SEQ ID NO: 110)
            com REV    5'-AGT CCT GCA GGG TGT GGT ATT C
                       (SEQ ID NO: 111)
            probe      5'-FAM-TAG ATT TTA GGG AAC "T" AAA TAG GGT CAC
                       TCA GGA C (SEQ ID NO: 112)

Oligonucleotide Mixture Proportions

The following is a list of mutation specific primers with an example of the ratios/proportions of these primers that can be used to specifically and sensitively detect the respective mutations.

| | Subtype B Reverse transcriptase | | |
|---|---|---|---|
| 41L | 41L F2 | (35%) | (SEQ ID NO: 63) |
| | 41L F5 | (10%) | (SEQ ID NO: 96) |
| | 41L F6 | (32%) | (SEQ ID NO: 97) |
| | 41L F3 | (13%) | (SEQ ID NO: 64) |
| | 41L F4 | (10%) | (SEQ ID NO: 65) |
| 67N | 67N F2 | (60%) | (SEQ ID NO: 69) |
| | 67N F3 | (40%) | (SEQ ID NO: 70) |
| 69T Set 1 | 69T F1‡ | (60%) | (SEQ ID NO: 12) |
| | 69T F2‡ | (40%) | (SEQ ID NO: 13) |
| 69T Set 2 | 69T F1‡ | (60%) | (SEQ ID NO: 12) |
| | 69T F2‡ | (40%) | (SEQ ID NO: 71) |
| 70R Set 1 | 70F1 | (40%) | (SEQ ID NO: 16) |
| | 70F2 | (12%) | (SEQ ID NO: 17) |
| | 70F3 | (10%) | (SEQ ID NO: 18) |
| | 70F4 | (38%) | (SEQ ID NO: 19) |
| 70R Set 3 | 70R REV1 | (70%) | (SEQ ID NO: 72) |
| | 70R REV2 | (30%) | (SEQ ID NO: 73) |
| 103N | 103F1 | (40%) | (SEQ ID NO: 22) |
| | 103F2 | (12%) | (SEQ ID NO: 23) |
| | 103F3 | (10%) | (SEQ ID NO: 24) |
| | 103F4 | (38%) | (SEQ ID NO: 25) |
| 181C | 181F1 | (76%) | (SEQ ID NO: 28) |
| | 181F2 | (34%) | (SEQ ID NO: 29) |
| 184V | 184F1 | (50%) | (SEQ ID NO: 33) |
| | 184F2 | (15%) | (SEQ ID NO: 34) |
| | 184F3 | (35%) | (SEQ ID NO: 35) |
| 215T Set 1 | 215T F1 | (70%) | (SEQ ID NO: 38) |
| | 215T F2 | (30%) | (SEQ ID NO: 39) |
| 215T Set 3 | 215T F3‡ | (70%) | (SEQ ID NO: 101) |
| | 215T F2‡ | (30%) | (SEQ ID NO: 75) |
| | Protease | | |
| 30N | 30N F1 | (70%) | (SEQ ID NO: 48) |
| | 30N F2 | (30%) | (SEQ ID NO: 49) |
| 90M | 90M F1 | (36%) | (SEQ ID NO: 78) |
| | 90M F2 | (33%) | (SEQ ID NO: 79) |
| | 90M F3 | (16%) | (SEQ ID NO: 55) |
| | 90M F4 | (15%) | (SEQ ID NO: 80) |
| | Subtype C Reverse transcriptase | | |
| 65R | 65F1 | (80%) | (SEQ ID NO: 117) |
| | 65F2 | (20%) | (SEQ ID NO: 118) |
| 65R | HIV-C 65R.5.1F | (20%) | (SEQ ID NO: 118) |
| | 65R.6F | (60%) | (SEQ ID NO: 117) |
| | HIV-C 6.1F | (20%) | (SEQ ID NO: 122) |
| 103N | 103CF1 | (47%) | (SEQ ID NO: 59) |
| | 103CF2 | (33%) | (SEQ ID NO: 60) |
| | 103CF3 | (20%) | (SEQ ID NO: 61) |

-continued

| | | | |
|---|---|---|---|
| 181C | 181C F1 | (72.5%) | (SEQ ID NO: 83) |
| | 181C F2 | (27.5%) | (SEQ ID NO: 84) |
| 184V | 184V F3 | (35%) | (SEQ ID NO: 102) |
| | 184V F4 | (40%) | (SEQ ID NO: 103) |
| | 184V F5 | (25%) | (SEQ ID NO: 104) |

Subtype AE
Reverse Transcriptase

| | | | |
|---|---|---|---|
| 65R | HIV-AE_K65R.1F | (100%) | (SEQ ID NO: 113) |

Integrase (Subtype B and others)

| | | | |
|---|---|---|---|
| 138K | HIV-B-IN 138K.1F | (100%) | (SEQ ID NO: 133) |
| 140S | HIV-B IN 140S.1F | (100%) | (SEQ ID NO: 134) |
| 155H | HIV-B-IN 155H.1R | (100%) | (SEQ ID NO: 137) |
| 148R | HIV-B-IN 148R.1R | (100%) | (SEQ ID NO: 138) |
| 148H | HIV-B-IN 148H.2R | (100%) | (SEQ ID NO: 139) |

The following is a list of probes with an example of the ratios/proportions of these probes that can be used to specifically and sensitively detect the respective mutations.

Subtype AE
Reverse Transcriptase

| | | | |
|---|---|---|---|
| 65R | AE Com 3.1P | (80%) | (SEQ ID NO: 115) |
| | AE Com 3.2P | (20%) | (SEQ ID NO: 116) |

Subtype C
Reverse Transcriptase

| | | | |
|---|---|---|---|
| 65R | HIV-C 65.1P | (80%) | (SEQ ID NO: 120) |
| | HIV-C 65.2P | (20%) | (SEQ ID NO: 121) |

Integrase (HIV-1 Subtype B and others)

| | | | |
|---|---|---|---|
| 138K | HIV-B-IN 138.1P | (80%) | (SEQ ID NO: 132) |
| | HIV-B-IN 138.2P | (20%) | (SEQ ID NO: 131) |
| 140S | HIV-B-IN 138.1P | (80%) | (SEQ ID NO: 132) |
| | HIV-B-IN 138.2P | (20%) | (SEQ ID NO: 131) |
| 155H | HIV-B IN COM.4.3P | (80%) | (SEQ ID NO: 140) |
| | HIV-B IN COM.4.4P | (20%) | (SEQ ID NO: 141) |
| 148R | HIV-B IN COM.4.3P | (80%) | (SEQ ID NO: 140) |
| | HIV-B IN COM.4.4P | (20%) | (SEQ ID NO: 141) |
| 148H | HIV-B IN COM.4.3P | (80%) | (SEQ ID NO: 140) |
| | HIV-B IN COM.4.4P | (20%) | (SEQ ID NO: 141) |

103N and 184V Assay Sensitivity with Virus Mixtures

Figure 2:
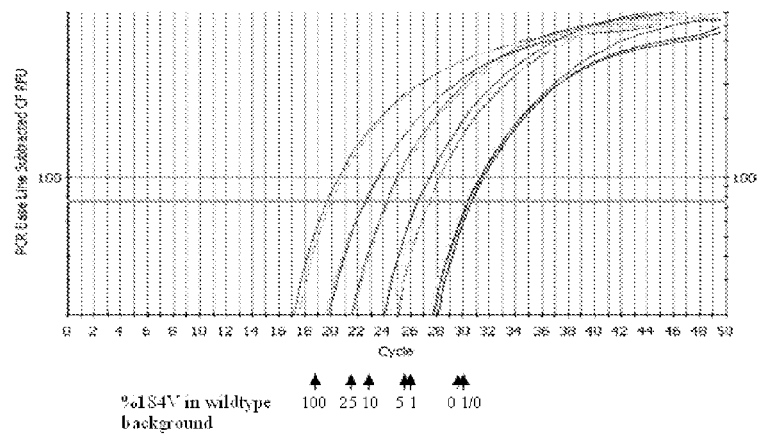
FIG. 2A shows the sensitivity of the assay for 184V.
FIG. 2B shows the lower limit for 184V detection in clinical specimens.
Figure 2:
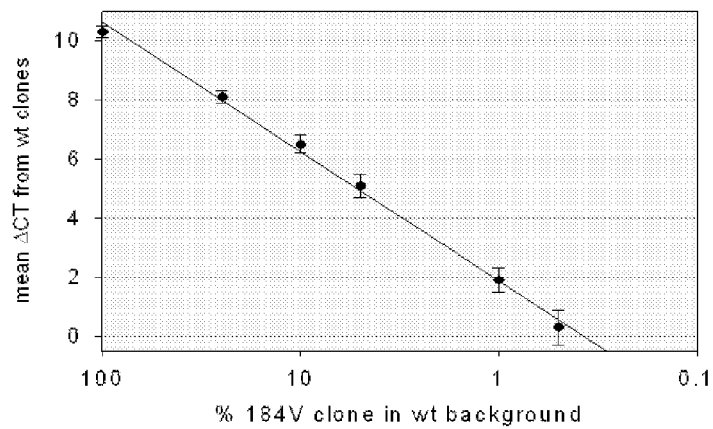

When tested against plasmid clones the mixed-primer assay for 103N was able to distinguish as little as 0.04% 103N in within a wild type background. The assay for 184V yielded discernable CTs for 184V plasmids when comprising as little as 0.2% of the population (FIG. 2A).

103N and 181C Assay Performance on Clinical Samples

Figure 3:
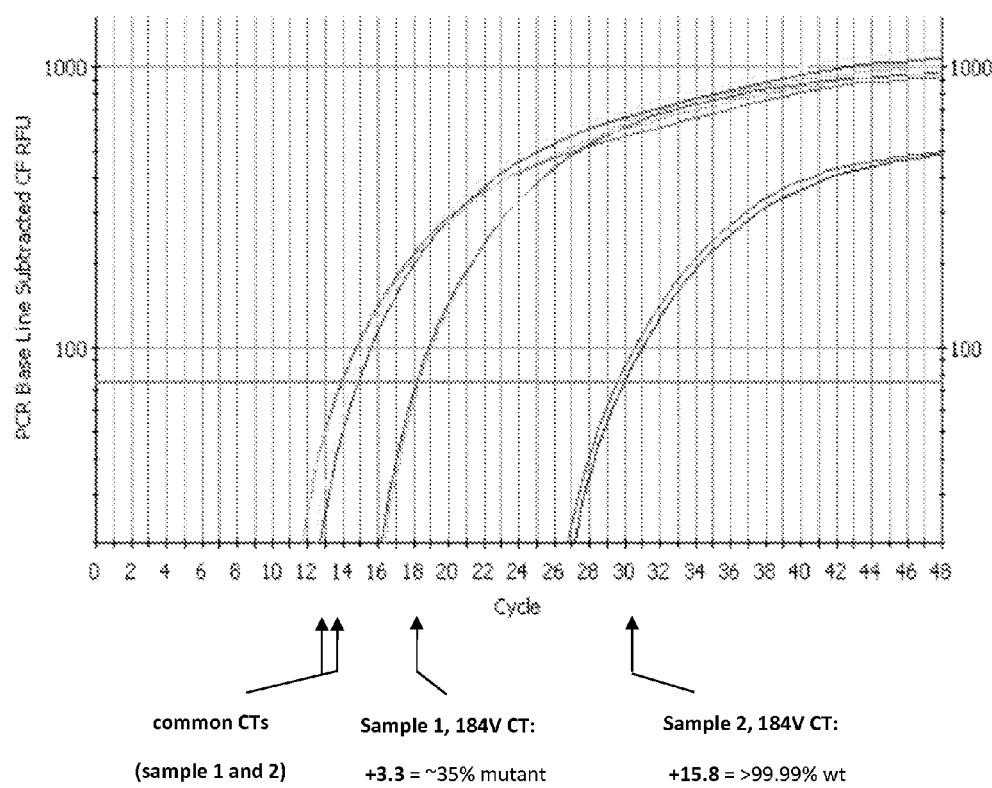
FIG. 3 shows the performance of the 184V assay on clinical specimens.
Figure 4:
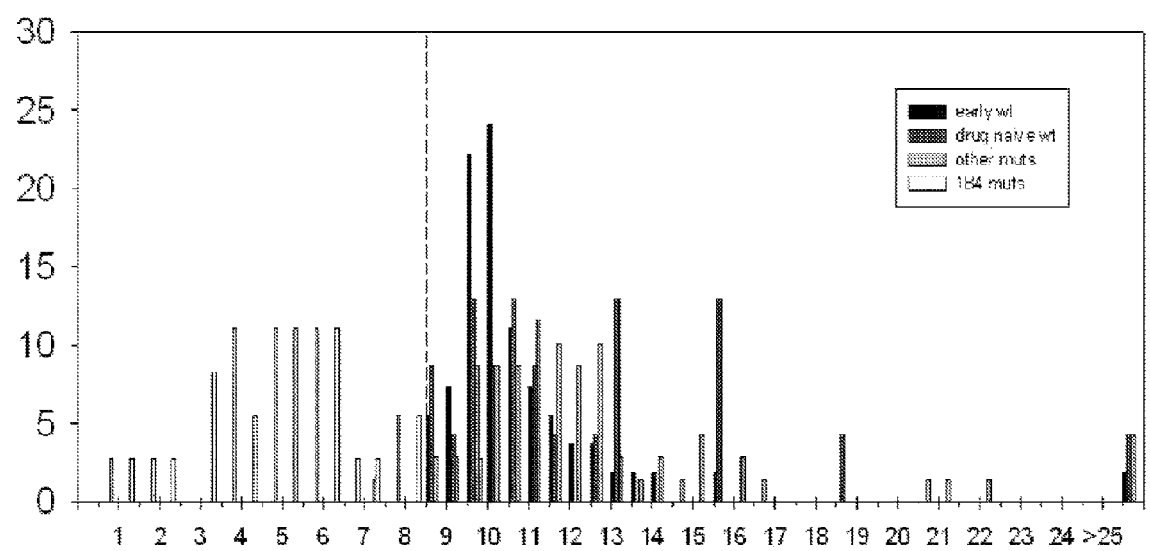
FIG. 4 shows the ΔCT frequency distribution for clinical samples.

To determine the overall assay performance on clinical specimens and establish the assay cutoff values, the data for the known patient-derived wild types and the 103N and 184V mutants were collated. An example of the performance of the 184V assay on a clinical specimen that carried the mutation and on a sample that had only wild type virus is shown in FIG. 3. The resulting distribution of collated ΔCTs revealed the best placement for the 103N cutoff to be a ΔCT of 12 and the 184V cutoff to be at a ΔCT of 8.5. That is, a ΔCT below these values is scored positive for the respective mutation, while a ΔCT above is scored as having only wild type (FIG. 4). As a group, the ΔCTs of the specimens documented to have mutations were significantly different from the ΔCTs of the wild type samples and samples possessing other mutations (P<0.001)(Table I). The 184V assay did not detect this mutation in any of the 77 documented wild type samples. However, with the 103N assay, 1 wild type sample scored positive (ΔCT of 10.6) for the mutation. The 103N discordant result might be signifying a very low level (<5%) naturally occurring polymorphism. The assay for the 103N mutation was able to detect the mutation in all 23 samples documented to have the mutation. The 184V assay was unable to detect the mutation in one (ΔCT of 9.8) of the 36 specimens known to have the mutation, yielding an assay sensitivity of 97.2%. This outlier was obtained from a treatment-experienced person having a mixed virus population with five polymorphisms in the primer binding site.

Using the 12.0 ΔCT cutoff for the 103N assay, none of 69 specimens documented to have mutations other than 103N scored positive. With the 8.5 ΔCT cutoff for 184V, one specimen previously determined to be negative for 184V scored positive (ΔCT of 7.1), giving the assay an overall specificity of 98.6%. This discordant sample was from a chronically infected, treatment-naïve person infected with virus carrying 41L and 215D RT mutations.

TABLE I

ΔCT Measures for Each Group of Clinical Samples

| | Mean ΔCT | Median ΔCT |
|---|---|---|
| 103N: | | |
| Early wildtype | 17.0 | 16.7 |
| Naive wildtype | 18.8 | 17.1 |
| Other mutants | 19.5 | 18.6 |
| 103N mutants | 5.8 | 5.5 |
| 184V: | | |
| Early wildtype | 10.9 | 10.2 |
| Naive wildtype | 12.5 | 11.1 |
| Other mutants | 12.8 | 11.7 |
| 184V mutants | 5.0 | 5.1 |

Performance of the 70R, 90M and 67N Assays on Transmitted Drug-Resistant Viruses The subtype B 70R assay cutoff=9.0 cycles, 90M assay cutoff=10.0 cycles, and 67N assay cutoff=9.0 cycles.

To reduce both the chance of false-positive results and the detection of naturally-occurring resistance-associated polymorphisms, assay cutoffs of 0.2-0.5% mutant virus were used for screening purposes. The sensitivities and specificities of the assays on genotyped clinical samples carrying the mutations of interest were found to range between 95-99%. Real-time PCR screening of the 147 transmitted HIV-1 carrying resistance-related mutations detected additional mutations that expanded the spectrum of drugs to which the viruses were resistant. The added mutants increased the prevalence of 90M from 8% to 10% (+25%), of 184V from 10% to 12% (+20%), of 70R from 9% to 14% (+56%), and of 67N from 7% to 12% (+71%).

HIV-1 Subtype C 103N and 181C Findings from a Study Examining the Emergence of Resistance in Women Receiving Intrapartum Single-Dose Nevirapine The subtype C HIV-1 103N assay cutoff=11.0 cycles, and the 181C assay cutoff=9.0 cycles.

Figure 5:
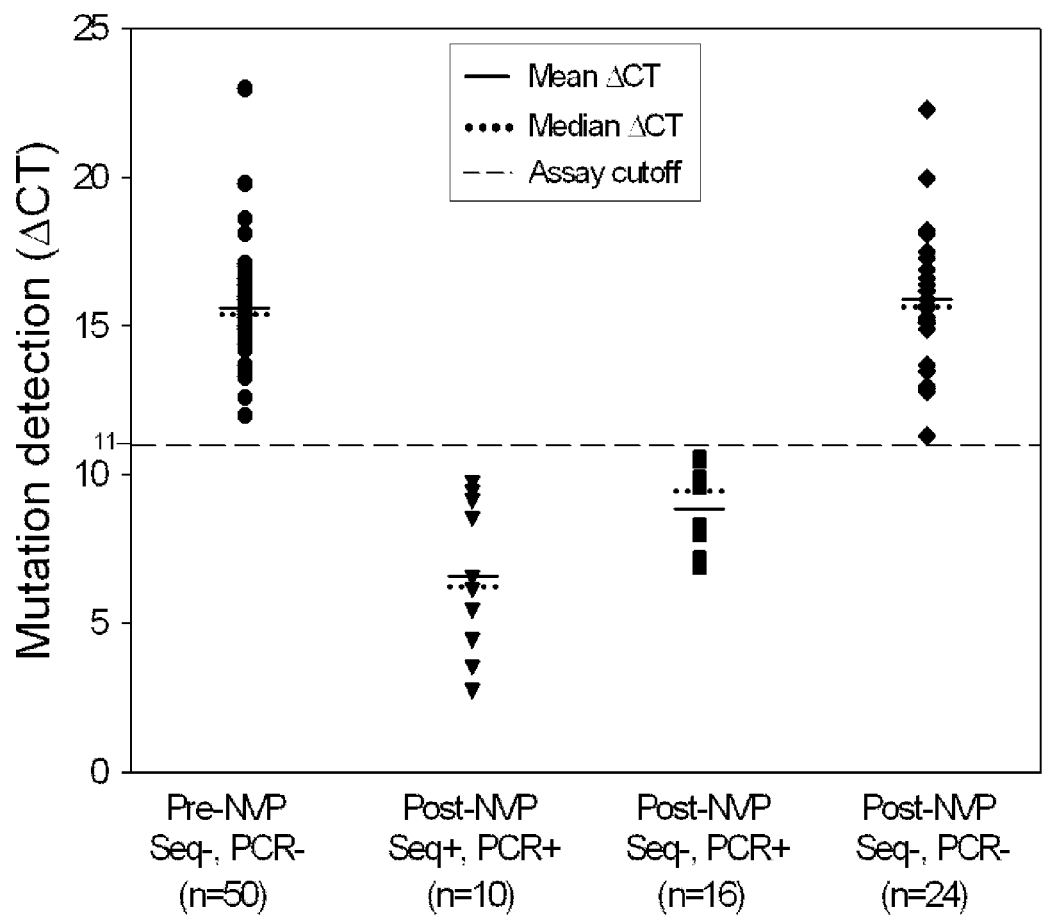
FIG. 5 shows the ΔCT values for real-time PCR analysis of the 103N mutation in pre-NVP and post-NVP plasma samples.

The 103N real-time assay confirmed the absence of detectable 103N in all 50 pre-NVP baseline samples (ΔCT range of 12.0-23.0 cycles, mean ΔCT=15.9 cycles) (FIG. 5). The assay successfully detected 103N in all 10 post-NVP positive control specimens (ΔCT range of 2.8-9.8 cycles, mean ΔCT=6.6 cycles). Of the 40 post-NVP specimens that had no detectable NVP-related mutations by sequencing, the real-time PCR assay found 16 (40%) were positive for 103N (ΔCT range of 6.9-10.6 cycles, mean ΔCT=8.9 cycles) (FIG. 3, table 1). The ΔCT values for the new-found 103N-positive specimens were significantly lower than the pre-NVP specimens (ΔΔCT) (paired FIG. 5 shows the real-time PCR analysis of the 103N mutation in pre-NVP and post-NVP plasma samples. Seq+/−, sequence analysis positive/negative for 103N; PCR+/−, real-time PCR positive/negative for 103N. A ΔCT value at or above the cutoff indicates 103N is not detected, a value below indicates the presence of 103N. T-test, p<0.0001, range=−(3.2-8.3) cycles, mean ΔΔCT=−6.0 cycles). In contrast, no significant difference was seen between the pre-NVP specimens and the negative post-NVP specimens (p=0.61). The resistant variants were identified in samples collected throughout the entire 36-week postpartum period.

The present real-time PCR primer-mix point mutation assay for the HIV-1 103N and 184V RT mutation were able to detect as little as 0.04% and 0.2% mutant virus, respectively, in HIV-1 plasmid dilutions. The primer designs were robust and worked well with the very high sequence variability in the clinical specimens examined. The ΔCTs of the mutation-positive specimens formed a distinct cluster from the wild type samples and samples with other mutations. These assays have shown acceptable performance on 282 samples of plasma-derived HIV-1, providing a sensitivity of 97.2-100% and a specificity of 98.6%.

The benefits of real-time PCR-based testing include the following: 1) The real-time reaction requires a one-step setup, decreasing the potential for user error; 2) High throughput: reactions performed in 96-well plate allowing up to 40 patient samples per plate with results in <3 hrs; 3) The use of primer mixtures can decrease the frequency of "no calls" often seen with other point mutation assays as a result of adjacent polymorphic mismatches; 4) This amplification-based technology is much more sensitive than conventional sequencing, and can be useful as both a primary screening tool and for post treatment evaluation; 5) This technology is currently used in public health lab settings and may be transferred to locations where current genotyping is cost-prohibitive; and 6) Real-time PCR is a powerful tool that can garner simultaneous virologic measures (e.g., virus load and resistance load).

Example 2: Screening for HIV-1 Subtype C Reverse Transcriptase Mutation 65R

Screening for HIV-1 subtype C RT mutation 65R is performed essentially as described by Johnson J A. et al. (2007) PLoS ONE 2(7): e638. doi:10.1371/journal.pone.0000638. HIV-1 genomic RNA is extracted (Qiagen UltraSens RNA kit) from 200 µL plasma or serum and reconstituted in 50 µL of buffer provided with the kit. To ensure sufficient template for repeat testing, virus sequences are first amplified from 5 µL HIV-1 RNA by reverse transcriptase-polymerase chain reaction (RT-PCR) using the reverse primer of SEQ ID NO: 6, and forward primer of SEQ ID NO: 5. PCR amplification conditions are 40 cycles of 95° C. for 45 seconds, 50° C. for 30 seconds, and 72° C. for 2 minutes.

Real-time PCR-based mutation-specific assays for the 65R mutation in HIV-1 subtype C. Mutation testing is performed in 96-well plates using 2 µL of 1:20 dilutions of the RT-PCR products, except that samples with viral loads below 5000 copies/mL are not diluted. The principle of the real-time PCR assay is to compare the differential amplifications of a mutation-specific PCR and a PCR that amplifies all viruses in the sample (total virus copy reaction) (FIG. 1). The HIV-1 total copy primers, forward SEQ ID NO: 7 and reverse SEQ ID NO: 8 that produce a product spanning n.t. 258-420 in reverse transcriptase and are used with the common probes, SEQ ID NO: 9. The cycle number at which the fluorescence emission exceeds the background fluorescence threshold is the threshold cycle (CT) and is the unit of measure for comparing the differences in amplification signals (ΔCT) between the total copy and mutation-specific reactions (FIG. 1B). All samples were tested in duplicate with the means of the total copy and mutation-specific CTs used for the determination of the ΔCT.

The mutation-specific primers of SEQ ID NOs: 118, 117 and 122 are designed to preferentially anneal with the targeted mutation nucleotide(s), thus having reduced affinity for wildtype sequences. To accommodate the various polymorphisms in large populations, degenerate nucleotides are placed at complementary positions in the primers. Specificity is enhanced by creating designed mismatches at nucleotide(s) −2 to −4 positions from the primer 3'-end. Furthermore, to cover the spectrum of polymorphisms present, mixtures of multiple degenerate primers are often required. Mutation-specific primer mixtures are experimentally evaluated and the ratios that best balance differences in primer avidities and minimize cross-interference in primer annealing are selected. Each change is re-evaluated against wildtype and mutant samples. The mutation specific forward primers are used in combination with a percent total primer concentration of each primer being SEQ ID NO: 118 (20%), SEQ ID NO: 117 (60%), and SEQ ID NO: 122 (20%).

Real-time PCRs are initiated with a hot-start incubation at 94° C. for 11 minutes before proceeding to 45 cycles of melting at 94° C. for 30 seconds, annealing at 50° C. for 15 seconds and extension at 60° C. for 30 seconds. All reactions are performed in a total volume of 25 or 50 µL/well in 96-well PCR plates using iCycler real-time PCR thermocyclers with optical units (Bio-Rad) and AmpliTaq Gold polymerase (2.5 U/reaction; Applied Biosystems). Final reagent concentrations are 320 nM for the forward and reverse primers, 160 nM probe(s), and 400 µM dNTPs. Low viral load samples that generate total copy CTs which appear after 26 cycles sometimes yielded false-positive results. To avoid this complication, all samples with CTs above 26 cycles are further amplified by nested PCR prior to real-time PCR testing. To adequately subtract background fluorescence, high virus load samples that produce total copy CTs appearing less than 10 cycles are diluted 1:100-1000 in RNase/DNase-free reagent-grade water and retested. We find that 1:20 dilutions of RT-PCR products from all but the samples with virus loads below 5000 copies/ml provided adequate template for real-time PCR testing.

Figure 6:
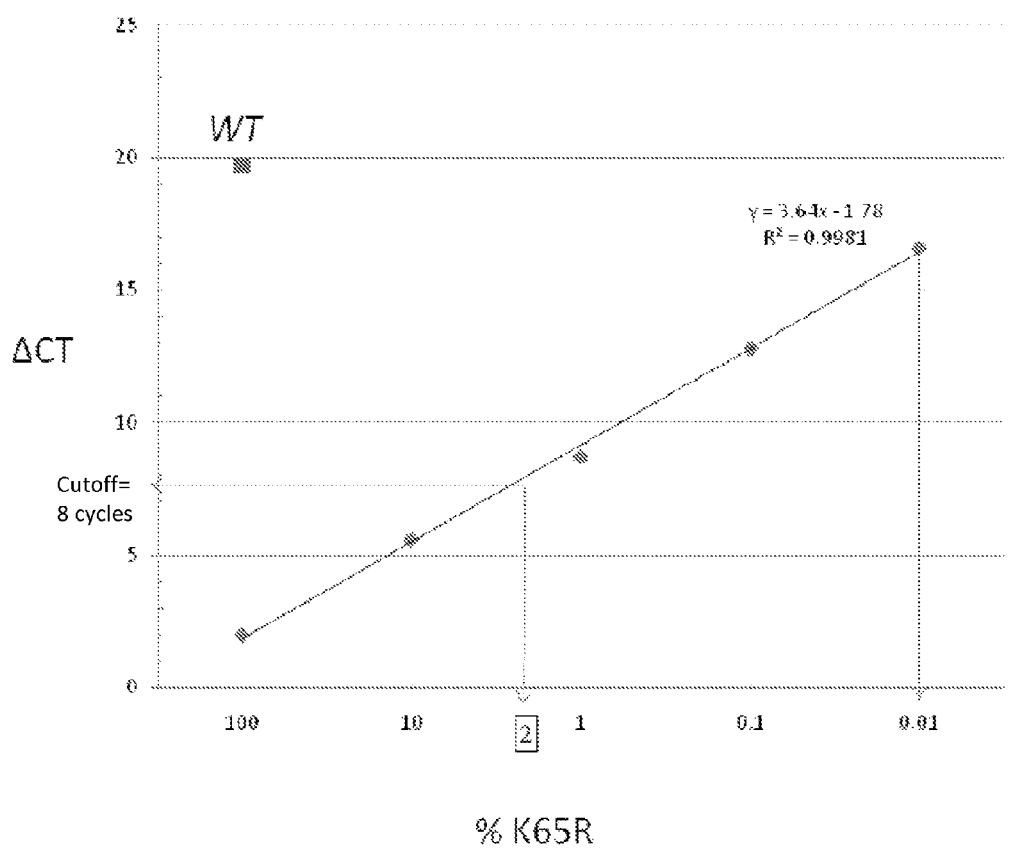
FIG. 6 shows the clinical and absolute detection limits of a method of detection of the HIV-1 subtype C 65R mutation.

Relative limits of detection are compared in a simple laboratory setting using serial dilutions of cloned mutant template in a background of wildtype template. The ΔCT that is equivalent to a 0.5 log greater reactivity than the wildtype mean ΔCT on the dilution curve is used to compare assay sensitivities (FIG. 6). This approach yields a clinical detection limit of 2% and an absolute detection limits of 0.01%.

Example 3: Screening for HIV-1 Integrase Mutations

Figure 7:
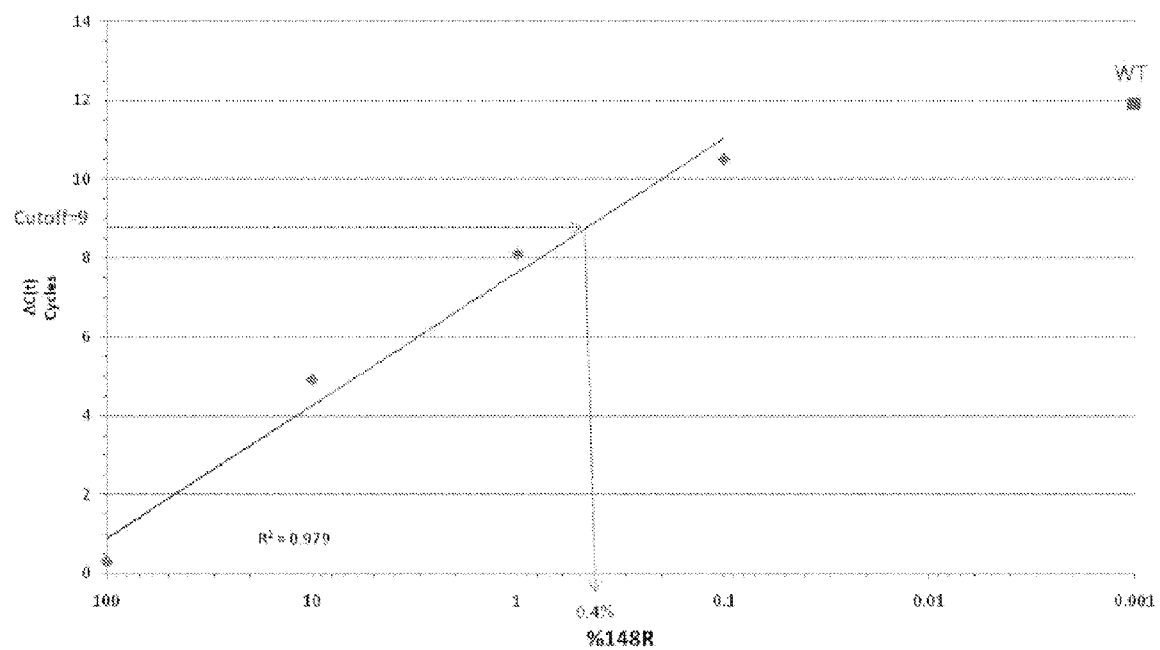
FIG. 7 shows the absolute detection limit of a method of detection of the HIV-1 integrase 148R mutation.

The methods of Example 2 are repeated using primers and probes for the specific detection of the HIV-1 integrase 148R mutation. Reverse transcription is performed using primers of SEQ ID NOs: 124 and 125. The DNA produced is then used in combination reaction amplifying two regions: 1) a common amplicon is produced using common primers SEQ ID NO: 26 and SEQ ID NO: 129; and 2) a mutation specific amplification reaction for the 148R mutation using mutation specific reverse primer SEQ ID NO: 138 and forward primer SEQ ID NO: 126. The probes for the common amplicon and the 148R reaction are SEQ ID NOs: 140 (80%) and 141 (20%). The absolute limits of detection obtained using these primers and probes is 0.4% (FIG. 7).

Similar reactions for the 140S, 15511, and 148R mutations in integrase are performed using the primer and probe sets identified herein with similar results.

Additional examples can be found in the publications of Li et al, *J. Infect. Dis.*, 2011, 203(6):798-802, and Johnson J A. et al. (2007) PLoS ONE 2(7): e638. doi:10.1371/journal.pone.0000638.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

REFERENCES

1. J. Mellors, et al. Abstract from the 11$^{th}$ CROI, San Francisco, Calif. (Feb. 9-11, 2004).
2. H. S. Weinstock, I. et al., J Infect Dis. 2004 Jun. 15; 189(12):2174-80.
3. Hance A J, et al., *J Viral* 2001 July; 75(14):6410-7.
4. S Palmer, et al. Abstract from the Third HIV DRP Symposium: Antiviral Drug Resistance, Chantilly, Va. (Dec. 8-11, 2002).

Patents and publications mentioned in the specification are indicative of the levels of those skilled in the art to which the invention pertains. These patents and publications are incorporated herein by reference to the same extent as if each individual application or publication was specifically and individually incorporated herein by reference The foregoing description is illustrative of particular embodiments of the invention, but is not meant to be a limitation upon the practice thereof. The following claims, including all equivalents thereof, are intended to define the scope of the invention.

The invention claimed is:

1. A method for detecting the presence or absence of the 65R mutation in the reverse transcriptase of HIV-1, comprising:
   (a) reverse transcribing RNA extracted from HIV-1 to produce a DNA product;
   (b) contacting the DNA product of step (a) with a reverse primer and a forward primer comprising a sequence selected from the group consisting of SEQ ID NO: 113, 118 and 122, or a combination thereof under conditions suitable for a polymerase chain reaction; and
   (c) detecting the presence or absence of the 65R mutation by detecting the presence or absence an amplification product produced by step (b).

2. An oligonucleotide having a sequence selected from the group consisting of SEQ ID NO: 113; SEQ ID NO: 118; SEQ ID NO: 122; SEQ ID NO: 133; SEQ ID NO: 134; SEQ ID NO: 137; SEQ ID NO: 138; and SEQ ID NO: 139.

3. The method of claim 1 wherein said HIV-1 is HIV-1 subtype C and said forward primer comprises SEQ ID NO: 118.

4. The method of claim 1 wherein the step of detecting is by hybridizing a probe or a combination of probes to said amplification product.

5. The method of claim 1 wherein the combination of said forward primers comprises 20% concentration of a primer comprising SEQ ID NO: 118.

6. A mixture of oligonucleotides comprising a reverse primer and forward primers having sequences of SEQ ID NO: 118 and SEQ ID NO: 122.

* * * * *